United States Patent
Subramanian et al.

(10) Patent No.: US 12,005,124 B2
(45) Date of Patent: *Jun. 11, 2024

(54) MUSCLE TARGETING COMPLEXES AND USES THEREOF FOR TREATING DYSTROPHINOPATHIES

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,894

(22) Filed: Oct. 24, 2023

(65) Prior Publication Data

US 2024/0066139 A1 Feb. 29, 2024

Related U.S. Application Data

(63) Continuation of application No. 18/181,623, filed on Mar. 10, 2023, now Pat. No. 11,833,217, which is a
(Continued)

(51) Int. Cl.
*A61K 47/54* (2017.01)
*A61K 39/00* (2006.01)
(Continued)

(52) U.S. Cl.
CPC .......... *A61K 47/6807* (2017.08); *A61K 47/10* (2013.01); *A61K 47/549* (2017.08);
(Continued)

(58) Field of Classification Search
None
See application file for complete search history.

(56) References Cited

U.S. PATENT DOCUMENTS 2,631,173 A 3/1953 Hillyer et al.
6,214,345 B1 4/2001 Firestone et al.
(Continued)

FOREIGN PATENT DOCUMENTS

CN 102459597 A 11/2010
CN 103443125 A 12/2013
(Continued)

OTHER PUBLICATIONS

Dommerholt "Readily Accessible Bicyclononynes for Bioorthogonal Labeling and Three-Dimensional Imaging of Living Cells" angew chem int 49:9422-9425 (Year: 2010).*

(Continued)

*Primary Examiner* — Aurora M Fontainhas
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload promotes the expression or activity of a functional dystrophin protein. In some embodiments, the molecular payload is an oligonucleotide, such as an antisense oligonucleotide, e.g., an oligonucleotide that causes exon skipping in a mRNA expressed from a mutant DMD allele.

30 Claims, 5 Drawing Sheets

Specification includes a Sequence Listing.

Related U.S. Application Data continuation of application No. 17/930,522, filed on Sep. 8, 2022, now Pat. No. 11,633,496, which is a continuation of application No. 17/751,875, filed on May 24, 2022, now Pat. No. 11,497,815, which is a continuation of application No. 17/580,844, filed on Jan. 21, 2022, now Pat. No. 11,369,689, which is a continuation of application No. 17/501,066, filed on Oct. 14, 2021, now Pat. No. 11,248,056, which is a continuation of application No. 17/205,151, filed on Mar. 18, 2021, now Pat. No. 11,168,141, which is a continuation of application No. 17/265,024, filed as application No. PCT/US2019/044949 on Aug. 2, 2019, now abandoned.

(60) Provisional application No. 62/855,766, filed on May 31, 2019, provisional application No. 62/714,031, filed on Aug. 2, 2018.

(51) Int. Cl.
*A61K 47/10* (2017.01)
*A61K 47/68* (2017.01)
*A61P 1/00* (2006.01)
*A61P 21/00* (2006.01)
*C07K 16/28* (2006.01)
*C12N 15/113* (2010.01)

(52) U.S. Cl.
CPC .......... *A61K 47/6849* (2017.08); *A61P 21/00* (2018.01); *C07K 16/2881* (2013.01); *C12N 15/113* (2013.01); *C12N 15/1137* (2013.01); *A61K 2039/505* (2013.01); *C07K 2317/24* (2013.01); *C07K 2317/33* (2013.01); *C07K 2317/55* (2013.01); *C07K 2317/77* (2013.01); *C07K 2317/92* (2013.01); *C12N 2310/11* (2013.01); *C12N 2310/14* (2013.01); *C12N 2310/315* (2013.01); *C12N 2310/3233* (2013.01); *C12N 2310/3513* (2013.01); *C12N 2320/32* (2013.01)

(56) References Cited

U.S. PATENT DOCUMENTS

| | | |
|---|---|---|
| 7,064,142 B2 | 6/2006 | Sato et al. |
| 7,265,131 B2 | 9/2007 | Johnson et al. |
| 7,534,879 B2 | 5/2009 | van Deutekom et al. |
| 7,575,886 B2 | 8/2009 | Venkataraman et al. |
| 7,960,541 B2 | 6/2011 | Wilton et al. |
| 7,973,015 B2 | 7/2011 | Den Dunnen et al. |
| 8,084,601 B2 | 12/2011 | Graham et al. |
| 8,232,384 B2 | 7/2012 | Wilton et al. |
| 8,324,371 B2 | 12/2012 | Graham et al. |
| 8,361,979 B2 | 1/2013 | van Ommen et al. |
| 8,455,636 B2 | 6/2013 | Fletcher et al. |
| 8,486,907 B2 | 7/2013 | Wilton et al. |
| 8,524,880 B2 | 9/2013 | Mcclorey et al. |
| 8,759,507 B2 | 6/2014 | van Deutekom et al. |
| 8,802,437 B2 | 8/2014 | Tremblay et al. |
| 8,859,629 B2 | 10/2014 | van Delft et al. |
| 8,865,883 B2 | 10/2014 | Kole et al. |
| 8,952,147 B2 | 2/2015 | Bouchard et al. |
| 9,018,368 B2 | 4/2015 | Wilton et al. |
| 9,024,007 B2 | 5/2015 | Wilton et al. |
| 9,078,911 B2 | 7/2015 | Lu et al. |
| 9,079,934 B2 | 7/2015 | Takeda et al. |
| 9,222,940 B2 | 12/2015 | van Delft et al. |
| 9,228,187 B2 | 1/2016 | Meloni et al. |
| 9,243,245 B2 | 1/2016 | De Kimpe et al. |
| 9,260,371 B2 | 2/2016 | Bertozzi et al. |
| 9,416,361 B2 | 8/2016 | Iversen et al. |
| 9,422,555 B2 | 8/2016 | Wilton et al. |
| 9,447,415 B2 | 9/2016 | Wilton et al. |
| 9,504,758 B2 | 11/2016 | van Delft et al. |
| 9,506,058 B2 | 11/2016 | Kaye |
| 9,512,424 B2 | 12/2016 | Wantanabe et al. |
| 9,550,834 B2 | 1/2017 | Shirai et al. |
| 9,610,362 B2 | 4/2017 | Armstrong |
| 9,657,049 B2 | 5/2017 | Koizumi et al. |
| 9,657,050 B2 | 5/2017 | Koizumi et al. |
| 9,708,361 B2 | 7/2017 | Takeda et al. |
| 9,708,406 B2 | 7/2017 | Zhang et al. |
| 9,758,783 B2 | 9/2017 | Meloni et al. |
| 9,840,706 B2 | 12/2017 | Tetsuya et al. |
| 9,970,010 B2 | 5/2018 | Graham et al. |
| 9,988,629 B2 | 6/2018 | Takeda et al. |
| 9,994,851 B2 | 6/2018 | Wilton et al. |
| 10,100,304 B2 | 10/2018 | van Deutkom et al. |
| 10,131,682 B2 | 11/2018 | Zhao |
| 10,144,931 B2 | 12/2018 | Enya et al. |
| 10,190,116 B2 | 1/2019 | van Deutekom et al. |
| 10,238,753 B2 | 3/2019 | Armstrong |
| 10,239,807 B2 | 3/2019 | van Delft et al. |
| 10,266,502 B2 | 4/2019 | van Delft et al. |
| 10,287,586 B2 | 5/2019 | Wilson et al. |
| 10,337,003 B2 | 7/2019 | Kaye |
| 10,364,431 B2 | 7/2019 | Kaye |
| 10,385,092 B2 | 8/2019 | Watanabe et al. |
| 10,407,461 B2 | 9/2019 | Watanabe et al. |
| 10,434,111 B2 | 10/2019 | Bertozzi et al. |
| 10,450,568 B2 | 10/2019 | Butler et al. |
| 10,487,106 B2 | 11/2019 | Watanabe et al. |
| RE47,751 E | 12/2019 | Wilton et al. |
| RE47,769 E | 12/2019 | Wilton et al. |
| 10,533,171 B2 | 1/2020 | van Deutekom et al. |
| 10,533,174 B2 | 1/2020 | Iversen et al. |
| 10,550,188 B2 | 2/2020 | Geall et al. |
| 10,704,060 B2 | 7/2020 | Gersbach et al. |
| 10,752,898 B2 | 8/2020 | Pietri et al. |
| 10,781,451 B2 | 9/2020 | Wilton et al. |
| 10,876,114 B2 | 12/2020 | van Deutekom et al. |
| RE48,468 E | 3/2021 | De Kimpe et al. |
| 11,111,309 B2 | 9/2021 | Subramanian et al. |
| 11,168,141 B2 | 11/2021 | Subramanian et al. |
| 11,230,605 B2 | 1/2022 | Launay et al. |
| 11,248,056 B1 | 2/2022 | Subramanian et al. |
| 11,286,305 B2 | 3/2022 | Subramanian et al. |
| 11,369,689 B2 | 6/2022 | Subramanian et al. |
| 11,390,682 B2 | 7/2022 | Subramanian et al. |
| 11,497,815 B2 | 11/2022 | Subramanian et al. |
| 11,518,816 B2 | 12/2022 | Subramanian et al. |
| 11,633,496 B2 | 4/2023 | Subramanian et al. |
| 11,633,498 B2 | 4/2023 | Subramanian et al. |
| 11,638,761 B2 | 5/2023 | Subramanian et al. |
| 11,648,318 B2 | 5/2023 | Subramanian et al. |
| 11,672,872 B2 | 6/2023 | Subramanian et al. |
| 11,679,161 B2 | 6/2023 | Subramanian et al. |
| 11,759,525 B1 | 9/2023 | Subramanian et al. |
| 11,771,776 B2 | 10/2023 | Subramanian et al. |
| 11,787,869 B2 | 10/2023 | Subramanian et al. |
| 11,795,233 B2 | 10/2023 | Subramanian et al. |
| 11,795,234 B2 | 10/2023 | Subramanian et al. |
| 11,833,217 B2 | 12/2023 | Subramanian et al. |
| 11,839,660 B2 | 12/2023 | Subramanian et al. |
| 11,844,843 B2 | 12/2023 | Subramanian et al. |
| 2004/0063654 A1 | 4/2004 | Davis et al. |
| 2004/0191243 A1 | 9/2004 | Chen et al. |
| 2005/0084906 A1 | 4/2005 | Goetsch et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2007/0050146 A1 | 3/2007 | Bentwich et al. |
| 2008/0025913 A1 | 1/2008 | Bowdish et al. |
| 2008/0177045 A1 | 7/2008 | Lee et al. |
| 2009/0269755 A1 | 10/2009 | Aartsma-Rus et al. |
| 2010/0130591 A1 | 5/2010 | Sazani et al. |
| 2010/0168212 A1 | 7/2010 | Popplewell et al. |
| 2011/0256157 A1 | 10/2011 | Howard et al. |
| 2011/0263682 A1 | 10/2011 | De Kimpe et al. |
| 2012/0077860 A1 | 3/2012 | Garcia et al. |
| 2012/0122801 A1 | 5/2012 | Platenburg |

(56) References Cited

U.S. PATENT DOCUMENTS

| | | |
|---|---|---|
| 2012/0201809 A1 | 8/2012 | Bhat et al. |
| 2012/0270925 A1 | 10/2012 | Wilton et al. |
| 2013/0028891 A1 | 1/2013 | Penichet et al. |
| 2013/0041017 A1 | 2/2013 | Kaplan et al. |
| 2013/0066063 A1 | 3/2013 | Berry et al. |
| 2013/0072541 A1 | 3/2013 | Garcia et al. |
| 2013/0137763 A1 | 5/2013 | van Delft et al. |
| 2013/0177579 A1 | 7/2013 | Lin et al. |
| 2014/0105916 A1 | 4/2014 | Brasel et al. |
| 2014/0193436 A1 | 7/2014 | Prudent |
| 2014/0323552 A1 | 10/2014 | Burghes et al. |
| 2014/0363455 A1 | 12/2014 | Stull et al. |
| 2015/0064181 A1 | 3/2015 | Armstrong |
| 2015/0191725 A1 | 7/2015 | van Deutekom et al. |
| 2015/0196670 A1 | 7/2015 | Dickson et al. |
| 2015/0247141 A1* | 9/2015 | Uhlmann ............ C12N 15/111 435/375 |
| 2015/0258210 A1 | 9/2015 | van Delft et al. |
| 2015/0266954 A1 | 9/2015 | Davies et al. |
| 2016/0015828 A1 | 1/2016 | Torgov et al. |
| 2016/0053262 A1* | 2/2016 | Platenburg ............ A61P 21/00 435/375 |
| 2016/0107999 A1 | 4/2016 | Debets et al. |
| 2016/0175460 A1 | 6/2016 | Arathoon et al. |
| 2016/0235861 A1 | 8/2016 | van Delft et al. |
| 2016/0237157 A1 | 8/2016 | Dennis et al. |
| 2016/0250347 A1 | 9/2016 | van Delft et al. |
| 2016/0272973 A1 | 9/2016 | Shehadeh |
| 2016/0304864 A1 | 10/2016 | De Kimpe et al. |
| 2016/0355599 A1* | 12/2016 | Sagert ............ A61P 35/00 |
| 2017/0002012 A1 | 1/2017 | van Delft et al. |
| 2017/0008858 A1 | 1/2017 | van Delft et al. |
| 2017/0072068 A1 | 3/2017 | Verkade et al. |
| 2017/0130256 A1 | 5/2017 | van Berkel et al. |
| 2017/0226554 A1 | 8/2017 | Wasiel et al. |
| 2017/0281795 A1 | 10/2017 | Geall et al. |
| 2017/0283799 A1 | 10/2017 | Kaye et al. |
| 2017/0348416 A1 | 12/2017 | Hasler et al. |
| 2018/0002433 A1 | 1/2018 | Zhang et al. |
| 2018/0028554 A1 | 2/2018 | De Visser et al. |
| 2018/0134797 A1 | 5/2018 | Zhang et al. |
| 2018/0142245 A1 | 5/2018 | Watanabe et al. |
| 2018/0171333 A1 | 6/2018 | Meloni et al. |
| 2018/0179538 A1 | 6/2018 | Takeda et al. |
| 2018/0265859 A1 | 9/2018 | Tremblay et al. |
| 2018/0369400 A1 | 12/2018 | Levin et al. |
| 2019/0000986 A1 | 1/2019 | Levin et al. |
| 2019/0008986 A1 | 1/2019 | Butler et al. |
| 2019/0038765 A1 | 2/2019 | van Berkel et al. |
| 2019/0092833 A1 | 3/2019 | Lin et al. |
| 2019/0092870 A1 | 3/2019 | Launay et al. |
| 2019/0112604 A1 | 4/2019 | De Kimpe et al. |
| 2019/0119383 A1 | 4/2019 | Bruenker et al. |
| 2019/0119679 A1 | 4/2019 | De Kimpe et al. |
| 2019/0127733 A1 | 5/2019 | Butler et al. |
| 2019/0153083 A1 | 5/2019 | Juste et al. |
| 2019/0177723 A1 | 6/2019 | Dickson et al. |
| 2019/0177725 A1 | 6/2019 | De Kimpe et al. |
| 2019/0209604 A1 | 7/2019 | Zhang et al. |
| 2019/0240346 A1 | 8/2019 | Sugo et al. |
| 2019/0249173 A1 | 8/2019 | Vargeese et al. |
| 2019/0270994 A1 | 9/2019 | Wilton et al. |
| 2019/0284556 A1 | 9/2019 | Sazani et al. |
| 2019/0323010 A1 | 10/2019 | Wilton et al. |
| 2019/0330626 A1 | 10/2019 | Rigo et al. |
| 2019/0336615 A1 | 11/2019 | Thompson et al. |
| 2019/0338311 A1 | 11/2019 | Amoasii et al. |
| 2019/0359982 A1 | 11/2019 | Kaye et al. |
| 2019/0364862 A1 | 12/2019 | Amoasii et al. |
| 2019/0390197 A1 | 12/2019 | Butler et al. |
| 2020/0040337 A1 | 2/2020 | Kaye et al. |
| 2020/0046742 A1 | 2/2020 | Bertozzi et al. |
| 2020/0046854 A1 | 2/2020 | Zhang et al. |
| 2020/0048174 A1 | 2/2020 | van Delft et al. |
| 2020/0123267 A1 | 4/2020 | Zhang et al. |
| 2020/0155702 A1 | 5/2020 | Bacica et al. |
| 2020/0239886 A1 | 7/2020 | De Kimpe et al. |
| 2020/0282074 A1 | 9/2020 | Levin et al. |
| 2020/0325237 A1 | 10/2020 | Darimont et al. |
| 2021/0038739 A1 | 2/2021 | Takahashi et al. |
| 2021/0130486 A1 | 5/2021 | Darimont et al. |
| 2021/0147576 A1 | 5/2021 | Laurent et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |
| 2023/0088865 A1 | 3/2023 | Subramanian et al. |
| 2023/0103793 A1 | 4/2023 | Subramanian et al. |
| 2023/0111147 A1 | 4/2023 | Subramanian et al. |
| 2023/0111212 A1 | 4/2023 | Subramanian et al. |
| 2023/0113823 A1 | 4/2023 | Subramanian et al. |
| 2023/0117883 A1 | 4/2023 | Subramanian et al. |
| 2023/0118799 A1 | 4/2023 | Subramanian et al. |
| 2023/0144436 A1 | 5/2023 | Subramanian et al. |
| 2023/0203180 A1 | 6/2023 | Subramanian et al. |
| 2023/0203181 A1 | 6/2023 | Subramanian et al. |
| 2023/0226212 A1 | 7/2023 | Subramanian et al. |
| 2023/0227569 A1 | 7/2023 | Subramanian et al. |
| 2023/0256112 A1 | 8/2023 | Subramanian et al. |
| 2023/0256113 A1 | 8/2023 | Subramanian et al. |
| 2023/0270873 A1 | 8/2023 | Subramanian et al. |
| 2023/0272065 A1 | 8/2023 | Subramanian et al. |
| 2023/0285582 A1 | 9/2023 | Subramanian et al. |
| 2023/0285586 A1 | 9/2023 | Subramanian et al. |
| 2023/0287108 A1 | 9/2023 | Subramanian et al. |
| 2023/0321264 A1 | 10/2023 | Subramanian et al. |
| 2023/0330247 A1 | 10/2023 | Hildebrand et al. |
| 2023/0330562 A1 | 10/2023 | Weeden et al. |
| 2023/0346966 A1 | 11/2023 | Subramanian et al. |
| 2023/0346967 A1 | 11/2023 | Subramanian et al. |
| 2024/0016950 A1 | 1/2024 | Weeden et al. |
| 2024/0016952 A1 | 1/2024 | Subramanian et al. |

FOREIGN PATENT DOCUMENTS

| | | |
|---|---|---|
| CN | 103732259 A | 4/2014 |
| EP | 1479771 A2 | 11/2004 |
| EP | 1619249 A1 | 1/2006 |
| EP | 2203173 B1 | 7/2010 |
| EP | 2284264 A1 | 2/2011 |
| EP | 2426203 A2 | 3/2012 |
| EP | 2614827 A2 | 7/2013 |
| EP | 2801618 A1 | 11/2014 |
| EP | 2623609 B1 | 1/2017 |
| EP | 3238737 A1 | 11/2017 |
| EP | 2922818 B1 | 9/2018 |
| EP | 3473270 A1 | 4/2019 |
| EP | 3560958 A1 | 10/2019 |
| IL | 54795 A | 10/1980 |

(56) References Cited

FOREIGN PATENT DOCUMENTS

| | | |
|---|---|---|
| JP | 2002-253259 A | 9/2002 |
| WO | WO 1989/007970 A1 | 9/1989 |
| WO | WO 1991/004753 A1 | 4/1991 |
| WO | WO 2006/000057 A1 | 1/2006 |
| WO | WO 2006/022688 A1 | 3/2006 |
| WO | WO 2007/135105 A1 | 11/2007 |
| WO | WO 2009/054725 A2 | 4/2009 |
| WO | WO 2009/144481 A2 | 12/2009 |
| WO | WO 2010/048586 A1 | 4/2010 |
| WO | WO 2010/050801 A1 | 5/2010 |
| WO | WO 2010/129861 A1 | 11/2010 |
| WO | WO 2011/057350 A1 | 5/2011 |
| WO | WO 2011/078797 A2 | 6/2011 |
| WO | WO 2011/136645 A1 | 12/2011 |
| WO | WO 2011/150408 A2 | 12/2011 |
| WO | WO 2011/154427 A1 | 12/2011 |
| WO | WO 2012/029986 A1 | 3/2012 |
| WO | WO 2012/075037 A1 | 6/2012 |
| WO | WO 2012/087962 A2 | 6/2012 |
| WO | WO 2013/026832 A1 | 2/2013 |
| WO | WO 2013/085550 A2 | 6/2013 |
| WO | WO 2013/100190 A1 | 7/2013 |
| WO | WO 2013/138662 A1 | 9/2013 |
| WO | WO 2013/162363 A1 | 10/2013 |
| WO | WO 2014/007620 A2 | 1/2014 |
| WO | WO 2014/065661 A1 | 5/2014 |
| WO | WO 2014/144978 A2 | 9/2014 |
| WO | WO 2014/153240 A2 | 9/2014 |
| WO | WO 2015/042581 A1 | 3/2015 |
| WO | WO 2015/179741 A1 | 11/2015 |
| WO | WO 2016/081643 A1 | 5/2016 |
| WO | WO 2016/081670 A2 | 5/2016 |
| WO | WO 2016/187425 A1 | 11/2016 |
| WO | WO 2016/205641 A2 | 12/2016 |
| WO | WO 2017/047707 A1 | 3/2017 |
| WO | WO 2017/100467 A2 | 6/2017 |
| WO | WO 2017/106643 A1 | 6/2017 |
| WO | WO 2017/143156 A1 | 8/2017 |
| WO | WO 2017/173408 A1 | 10/2017 |
| WO | WO 2017/192679 A1 | 11/2017 |
| WO | WO 2017/205191 A1 | 11/2017 |
| WO | WO 2017/205513 A1 | 11/2017 |
| WO | WO 2017/221883 A1 | 12/2017 |
| WO | WO 2018/007475 A1 | 1/2018 |
| WO | WO 2018/014042 A1 | 1/2018 |
| WO | WO 2018/017754 A1 | 1/2018 |
| WO | WO 2018/091544 A1 | 5/2018 |
| WO | WO 2018/098480 A1 | 5/2018 |
| WO | WO 2018/100010 A1 | 6/2018 |
| WO | WO 2018/107003 A1 | 6/2018 |
| WO | WO 2018/129296 A1 | 7/2018 |
| WO | WO2018129384 * | 7/2018 |
| WO | WO 2018/226861 A1 | 12/2018 |
| WO | WO 2019/014772 A1 | 1/2019 |
| WO | WO 2019/059973 A1 | 3/2019 |
| WO | WO 2019/060775 A1 | 3/2019 |
| WO | WO 2019/067975 A1 | 4/2019 |
| WO | WO 2019/071028 A1 | 4/2019 |
| WO | WO 2019/092507 A1 | 5/2019 |
| WO | WO 2019/113393 A1 | 6/2019 |
| WO | WO 2019/136180 A2 | 7/2019 |
| WO | WO 2019/136216 A1 | 7/2019 |
| WO | WO 2019/151539 A1 | 8/2019 |
| WO | WO 2019/152609 A1 | 8/2019 |
| WO | WO 2019/157224 A1 | 8/2019 |
| WO | WO 2019/200185 A1 | 10/2019 |
| WO | WO 2019/215175 A1 | 11/2019 |
| WO | WO 2019/215333 A1 | 11/2019 |
| WO | WO 2019/229658 A1 | 12/2019 |
| WO | WO 2019/241385 A2 | 12/2019 |
| WO | WO 2019/246480 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |
| WO | WO 2020/028857 A1 | 2/2020 |
| WO | WO 2020/028861 A1 | 2/2020 |
| WO | WO 2020/028864 A1 | 2/2020 |
| WO | WO 2020/084488 A1 | 4/2020 |
| WO | WO 2020/094670 A1 | 5/2020 |
| WO | WO 2020/132584 A1 | 6/2020 |
| WO | WO 2020/219820 A1 | 10/2020 |
| WO | WO 2020/247738 A1 | 12/2020 |
| WO | WO 2020/247782 A1 | 12/2020 |
| WO | WO 2020/247818 A1 | 12/2020 |
| WO | WO 2021/003573 A1 | 1/2021 |
| WO | WO 2021/068761 A1 | 4/2021 |
| WO | WO 2021/076856 A1 | 4/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |
| WO | WO 2022/026152 A1 | 2/2022 |
| WO | WO 2022/051665 A1 | 3/2022 |
| WO | WO 2022/056266 A2 | 3/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |
| WO | WO 2023/044398 A1 | 3/2023 |
| WO | WO 2023/077120 A1 | 5/2023 |
| WO | WO 2023/086864 A1 | 5/2023 |
| WO | WO 2023/201318 A1 | 10/2023 |
| WO | WO 2023/201324 A1 | 10/2023 |
| WO | WO 2023/201332 A1 | 10/2023 |
| WO | WO 2024/011135 A1 | 1/2024 |
| WO | WO 2024/011150 A1 | 1/2024 |

OTHER PUBLICATIONS

CDER "206488Orig1s000" accessed from accessdata.fda.gov on May 21, 2021 (Year: 2016).*

[No Author Listed] GenBank: AF095738.1. Mus musculus dystrophin gene, exons 22-25 and partial CDs. 2016. Retrieved from the internet Oct. 30, 2019: https://www.ncbi.nlm.nih.gov/nucleotide/AF095738.1?report=genbank&log$=nuclalign&blast_rank=3&RID=VKBMZ9WW014, 5 pages.

[No Author Listed] GenBank: CAE7739414. Unnamed protein product, partial [Symbiodinium pilosum]. Feb. 18, 2021. Retrieved from the internet Oct. 12, 2022: https://www.ncbi.nlm.nih.gov/protein/CAE7739414.1.1?report=genbank&log$=prottop&blast_rank=1&RID=MDW2CW3T013, 1 page.

[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.

(56) References Cited

OTHER PUBLICATIONS

[No Author Listed] GenBank: PKK91089. Hypothetical protein CVV64_04785 [Candidatus Wallbacteria bacterium HGW-Wallbacteria-1]. Oct. 13, 2017. Retrieved from the internet Oct. 12, 2022: https://www.ncbi.nlm.nih.gov/protein/PKK91089.1?report=genbank &log$=prottop&blast_rank=2&RID=MDW2CW3T013, 2 pages.
[No Author Listed] UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.
[No Author Listed] Wikipedia, Dystrophin, Mar. 9, 2018. Retrieved from the internet Nov. 5, 2019: https://en.wikipedia.org/w/index.php?title=Dystrophin&oldid=829543258, 10 pages.
[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.
[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.
[No Author Listed] Exondys (eteplirsen): EPAR—Refusal public assessment report and Annex: Scientific conclusions and grounds for refusal. European Medicines Agency. Sep. 20, 2018. 140 pages.
[No Author Listed], Building the world's leading muscle disease company. Dyne Company Overview. Jun. 2021. 42 pages.
[No Author Listed], Clinical trial summary NCT000159250 (Version 4, dated Oct. 11, 2007). 9 pages.
[No Author Listed], Highlights of prescribing information EXONDYS 51. FDA. <accessdata.fda.gov> Sep. 2016. Retrieved May 22, 2021. 11 pages.
[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.
[No Author Listed], Morpholino History, Production, and Properties. Gene Tools. Retrieved from https://gene-tools.com/history_production_and_properties. Accessed Jan. 9, 2023. 5 pages.
[No Author Listed], NCBI "NM_004006.2(DMD)". Published Oct. 30, 2020. Accessed from ncbi.nlm.nih.gov on May 21, 2021. 2 pages.
[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kDa (Year: 2021). 3 pages.
Aartsma-Rus et al., Antisense-induced multiexon skipping for Duchenne muscular dystrophy makes more sense. Am J Hum Genet. Jan. 2004;74(1):83-92. Epub Dec. 16, 2003.
Aartsma-Rus et al., Antisense-mediated exon skipping: a versatile tool with therapeutic and research applications. RNA. Oct. 2007;13(10):1609-24. doi: 10.1261/rna.653607. Epub Aug. 7, 2007.
Aartsma-Rus et al., Antisense-mediated modulation of splicing: therapeutic implications for Duchenne muscular dystrophy. RNA Biol. Jul.-Aug. 2010;7(4):453-61. doi: 10.4161/rna.7.4.12264. Epub Jul. 1, 2010.
Aartsma-Rus et al., Guidelines for antisense oligonucleotide design and insight into splice-modulating mechanisms. Mol Ther. Mar. 2009;17(3):548-53. doi: 10.1038/mt.2008.205. Epub Sep. 23, 2008.
Aartsma-Rus et al., Less is more: therapeutic exon skipping for Duchenne muscular dystrophy. Lancet Neurol. Oct. 2009;8(10):873-5. doi: 10.1016/S1474-4422(09)70229-7. Epub Aug. 25, 2009.
Aartsma-Rus et al., Progress in therapeutic antisense applications for neuromuscular disorders. Eur J Hum Genet. Feb. 2010;18(2):146-53. Epub Oct. 7, 2009.
Aartsma-Rus et al., Targeted exon skipping as a potential gene correction therapy for Duchenne muscular dystrophy. Neuromuscul Disord. Oct. 2002;12 Suppl 1:S71-7. doi: 10.1016/s0960-8966(02)00086-x.
Adams et al., Antisense oligonucleotide induced exon skipping and the dystrophin gene transcript: cocktails and chemistries. BMC Mol Biol. Jul. 2, 2007;8:57.
Agard et al., A Comparative Study of Bioorthogonal Reactions with Azides. ACS Chem. Biol. 2006;1(10):644-8. Epub Oct. 20, 2006.
Agard et al., A Strain-Promoted [3+2] Azide-Alkyne Cycloaddition for Covalent Modification of Biomolecules in Living Systems. J. Am. Chem. Soc. Nov. 2004;126(46):15046-7.
Alter et al., Systemic delivery of morpholino oligonucleotide restores dystrophin expression bodywide and improves dystrophic pathology. Nat Med. Feb. 2006;12(2):175-7. doi: 10.1038/nm1345. Epub Jan. 29, 2006.
Anciaux et al., Transition-metal-catalyzed reactions of diazo compounds. 1. Cyclopropanation of double bonds. The Journal of Organic Chemistry. Feb. 1980;45(4):695-702.
Antony-Mayer et al., Bicyclo[6.1.0]nonynes. Chemische Berichte. Nov. 1988;121(11):2013-8.
Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.
Arechavala-Gomeza et al., Comparative analysis of antisense oligonucleotide sequences for targeted skipping of exon 51 during dystrophin pre-mRNA splicing in human muscle. Hum Gene Ther. Sep. 2007;18(9):798-810. doi: 10.1089/hum.2006.061.
Arnett et al., Therapy for neuromuscular disorders. Curr Opin Genet Dev. Jun. 2009;19(3):290-7. doi: 10.1016/j.gde.2009.03.005. Epub May 4, 2009.
Ast et al., Estergruppenhaltige Polyalkenylene durch Olefin-Metathese. Die Makromolekulare Chemie. May 1976;177(5):1349-55.
Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.
Baskin et al., Copper-free click chemistry for dynamic in vivo imaging. PNAS. Oct. 2007;104(43):16793-7.
Beskrovnaya, FORCE™ platform delivers exon skipping PMO, leads to durable increases in dystrophin protein in mdx mice and is well tolerated NHPs. Presented at Muscle Study Group Annual Scientific Meeting. Oct. 1, 2021. 29 pages.
Bien-Ly et al., Transferrin receptor (TfR) trafficking determines brain uptake of TfR antibody affinity variants. J Exp Med. Feb. 10, 2014;211(2):233-44. Epub Jan. 27, 2014.
Black, 9.13.4.1.1.3.2 Variation 2: C-Alkylation (and Arylation) by Carbenes and Free Radicals. Science of Synthesis. 2001;9:514.
Bushby et al., MSG/ENMC for DMD Trial Study Group. 145th ENMC International Workshop: planning for an International Trial of Steroid Dosage Regimes in DMD (For DMD), Oct. 22-24, 2006, Naarden, The Netherlands. Neuromuscul Disord. May 2007;17(5):423-8. doi: 10.1016/j.nmd.2007.01.006. Epub Apr. 11, 2007.
Bushby et al., Report on the 124th ENMC International Workshop. Treatment of Duchenne muscular dystrophy; defining the gold standards of management in the use of corticosteroids. Apr. 2-4, 2004, Naarden, The Netherlands. Neuromuscul Disord. Sep. 2004;14(8-9):526-34.
Bushby et al., The multidisciplinary management of Duchenne muscular dystrophy. Curr Paed. 2005; 15: 292-300.
Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.
Campbell et al., Deflazacort for the treatment of Duchenne Dystrophy: a systematic review. BMC Neurol. Sep. 8, 2003;3:7. doi: 10.1186/1471-2377-3-7. Epub Sep. 8, 2003.
Candelaria et al., Antibodies Targeting the Transferrin Receptor 1 (TfR1) as Direct Anti-cancer Agents. Front Immunol. Mar. 17, 2021;12:607692.
Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.
Cenik et al., Argonaute proteins. Curr Biol. Jun. 21, 2011;21(12):R446-9.

(56) References Cited

OTHER PUBLICATIONS

Chen et al., In-depth structural characterization of Kadcyla® (ado-trastuzumab emtansine) and its biosimilar candidate. MAbs. Oct. 2016;8(7):1210-1223. doi: 10.1080/19420862.2016.1204502. Epub Jul. 5, 2016.

Chothia et al., Canonical structures for the hypervariable regions of immunoglobulins. J Mol Biol. Aug. 20, 1987;196(4):901-17. doi: 10.1016/0022-2836(87)90412-8.

Cirak et al., Exon skipping and dystrophin restoration in patients with Duchenne muscular dystrophy after systemic phosphorodiamidate morpholino oligomer treatment: an open-label, phase 2, dose-escalation study. Lancet. Aug. 13, 2011;378(9791):595-605. doi: 10.1016/S0140-6736(11)60756-3. Epub Jul. 23, 2011.

Clark et al., Increased brain uptake of targeted nanoparticles by adding an acid-cleavable linkage between transferrin and the nanoparticle core. PNAS. Oct. 2015;112(40):12486-91.

Codelli et al., Second-Generation Difluorinated Cyclooctynes for Copper-Free Click Chemistry. J. Am. Chem. Soc. 2008;130(34):11486-11493. Epub Aug. 5, 2008.

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

Danis et al., Potential therapeutic application of antisense oligonucleotides in the treatment of ocular diseases. Expert Opin Pharmacother. Feb. 2001;2(2):277-91.

Darimont et al., A novel antibody-oligonucleotide conjugate (AOC) platform enables efficient regulation of muscle targets in mice. Abstract. 8-05. J. Cach Sarcopen Musc. 2017; 8: 1065-66.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Desjardins et al., Building a FORCETM platform-based DMD franchise for the treatment of individuals with mutations amenable to exon skipping. Neuromusc Dis. Oct. 2022; 32: S101-2. Abstract.

Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.

Desjardins et al., ForceTM platform achieves robust exon skipping, restores dystrophin at the sarcolemma and halts progression of fibrosis in the severe D2-mdx model of DMD. Abstract. Mar. 2023. 1 page.

Desjardins et al., ForceTM platform achieves robust exon skipping, restores dystrophin at the sarcolemma and halts progression of fibrosis in the severe D2-mdx model of DMD. Poster. Presented at The Muscular Dystrophy Association Clinical and Scientific Conference. Mar. 19-22, 2023. 1 page.

Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.

Echigoya et al., Effects of systemic multiexon skipping with peptide-conjugated morpholinos in the heart of a dog model of Duchenne muscular dystrophy. Proc Natl Acad Sci U S A. Apr. 18, 2017;114(16):4213-4218. doi: 10.1073/pnas.1613203114. Epub Apr. 3, 2017.

Echigoya et al., Exons 45-55 Skipping Using Mutation-Tailored Cocktails of Antisense Morpholinos in the DMD Gene. Mol Ther. Nov. 6, 2019;27(11):2005-2017. doi: 10.1016/j.ymthe.2019.07.012. Epub Jul. 26, 2019.

Echigoya et al., Quantitative Antisense Screening and Optimization for Exon 51 Skipping in Duchenne Muscular Dystrophy. Mol Ther. Nov. 1, 2017;25(11):2561-2572. doi: 10.1016/j.ymthe.2017.07.014. Epub Jul. 28, 2017.

Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.

Elangkovan et al., Gene Therapy for Duchenne Muscular Dystrophy. J Neuromuscul Dis. 2021;8(s2):S303-S316.

Fletcher et al., Morpholino oligomer-mediated exon skipping averts the onset of dystrophic pathology in the mdx mouse. Mol Ther. Sep. 2007;15(9):1587-92. doi: 10.1038/sj.mt.6300245. Epub Jun. 19, 2007.

Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Gebski et al., Morpholino antisense oligonucleotide induced dystrophin exon 23 skipping in mdx mouse muscle. Hum Mol Genet. Aug. 1, 2003;12(15):1801-11.

Girones et al. Comparison of the kinetics of cycling of the transferrin receptor in the presence or absence of bound diferric transferrin. Biochem J. Nov. 15, 1989;264(1):35-46.

Goemans et al., Systemic administration of PRO051 in Duchenne's muscular dystrophy. N Engl J Med. Apr. 21, 2011;364(16):1513-22. doi: 10.1056/NEJMoa1011367. Epub Mar. 23, 2011. Erratum in: N Engl J Med. Oct. 6, 2011;365(14):1361.

Gong et al., Simple Method To Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Griggs et al., Prednisone in Duchenne dystrophy. A randomized, controlled trial defining the time course and dose response. Clinical Investigation of Duchenne Dystrophy Group. Arch Neurol. Apr. 1991;48(4):383-8. doi: 10.1001/archneur.1991.00530160047012.

Guirguis et al., Disease-drug interaction: Reduced response to propranolol despite increased concentration in the rat with inflammation. J Pharm Sci. May 2003;92(5):1077-84. Abstract.

Haack et al., Toxic rise of clozapine plasma concentrations in relation to inflammation. Eur Neuropsychopharmacol. Oct. 2003;13(5):381-5.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.

Henry et al., Chemically modified oligonucleotides exhibit decreased immune stimulation in mice. J Pharmacol Exp Ther. Feb. 2000;292(2):468-79.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

(56) References Cited

OTHER PUBLICATIONS

Jeara Wiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.

Jirka et al., Cyclic Peptides to Improve Delivery and Exon Skipping of Antisense Oligonucleotides in a Mouse Model for Duchenne Muscular Dystrophy. Mol Ther. Jan. 3, 2018;26(1):132-147. doi: 10.1016/j.ymthe.2017.10.004. Epub Oct. 12, 2017.

Juliano, The delivery of therapeutic oligonucleotides. Nucleic Acids Res. Aug. 19, 2016;44(14):6518-48. doi: 10.1093/nar/gkw236. Epub Apr. 15, 2016.

Khan, Corticosteroid therapy in Duchenne muscular dystrophy. J Neurol Sci. Dec. 1, 1993;120(1):8-14.

Kinali et al., Local restoration of dystrophin expression with the morpholino oligomer AVI-4658 in Duchenne muscular dystrophy: a single-blind, placebo-controlled, dose-escalation, proof-of-concept study. Lancet Neurol. Oct. 2009;8(10):918-28. doi: 10.1016/S1474-4422(09)70211-X. Epub Aug. 25, 2009. Erratum in: Lancet Neurol. Dec. 2009;8(12):1083.

Kline et al., Methods to Make Homogenous Antibody Drug Conjugates. Pharm Res. Nov. 2015;32(11):3480-93. Epub Dec. 16, 2014.

Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Lawrence et al., Crystal structure of the ectodomain of human transferrin receptor. Science. Oct. 22, 1999;286(5440):779-82. doi: 10.1126/science.286.5440.779.

Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Levin, Targeting Therapeutic Oligonucleotides. N Engl J Med. Jan. 5, 2017;376(1):86-88. doi: 10.1056/NEJMcibr1613559.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Lu et al., Functional amounts of dystrophin produced by skipping the mutated exon in the mdx dystrophic mouse. Nat Med. Aug. 2003;9(8):1009-14. Epub Jul. 6, 2003.

Lu et al., Systemic delivery of antisense oligoribonucleotide restores dystrophin expression in body-wide skeletal muscles. Proc Natl Acad Sci U S A. Jan. 4, 2005;102(1):198-203. doi: 10.1073/pnas.0406700102. Epub Dec. 17, 2004.

Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.

Mann et al., Antisense-induced exon skipping and synthesis of dystrophin in the mdx mouse. Proc Natl Acad Sci U S A. Jan. 2, 2001;98(1):42-7.

Manzur et al., Update on the management of Duchenne muscular dystrophy. Arch Dis Child. Nov. 2008;93(11):986-90. doi: 10.1136/adc.2007.118141. Epub Jul. 30, 2008.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mojsov et al., A Quantitative Evaluation of Methods for Coupling Asparagine. The Journal of Organic Chemistry. Feb. 1980;45(4):555-60.

Naylor et al., Deliver, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.

Naylor et al., Deliver, a randomized, double-blind, placebo controlled, multiple ascending dose study of DYNE-251 in boys with DMD amenable to Exon 51 skipping. Abstract. Mar. 2023. 1 page.

Nguyen et al., Antisense oligonucleotides for the treatment of cardiomyopathy in Duchenne muscular dystrophy. Am J Transl Res. Mar. 15, 2019;11(3):1202-1218.

Novak et al., Myoblasts and macrophages are required for therapeutic morpholino antisense oligonucleotide delivery to dystrophic muscle. Nat Commun. Oct. 16, 2017;8(1):941. doi: 10.1038/s41467-017-00924-7. Erratum in: Nat Commun. Jan. 15, 2018;9(1):208. Erratum in: Nat Commun. Mar. 23, 2018;9(1):1256.

Nowak et al., Duchenne muscular dystrophy and dystrophin: pathogenesis and opportunities for treatment. EMBO Rep. Sep. 2004;5(9):872-6.

Padlan et al., A possible procedure for reducing the immunogenicity of antibody variable domains while preserving their ligand-binding properties. Molecular Immunology. Apr.-May 1991;28(4-5):489-98.

Panowski et al., Site-specific antibody drug conjugates for cancer therapy. MAbs. Jan.-Feb. 2014;6(1):34-45.

Picariello et al., Dyne-101 achieves durable knockdown of toxic human nuclear DMPK RNA and correction of splicing in the hTfR1/DMSXL mouse model of DM1. Presented at The Muscular Dystrophy Association Clinical and Scientific Conference. Mar. 13-16, 2022. 1 page.

Pradeepkumar, Chemically modified oligonucleotides: synthesis, physicochemical and biochemical properties of their duplexes with DNA and RNA. Comprehensive Summaries of Uppsala Dissertations from the Faculty of Science and Technology. 2004; 973: 56 pages.

Pradhan et al., Prednisolone in Duchenne muscular dystrophy with imminent loss of ambulation. J Neurol. Oct. 2006;253(10):1309-16. doi: 10.1007/s00415-006-0212-1. Epub Jun. 19, 2006.

Qian et al., Targeted drug delivery via the transferrin receptor-mediated endocytosis pathway. Pharmacol Rev. Dec. 2002;54(4):561-87. doi: 10.1124/pr.54.4.561.

Rando et al., Rescue of dystrophin expression in mdx mouse muscle by RNA/DNA oligonucleotides. Proc Natl Acad Sci U S A. May 9, 2000;97(10):5363-8. doi: 10.1073/pnas.97.10.5363.

Roberts et al., Advances in oligonucleotide drug delivery. Nat Rev Drug Discov. Oct. 2020;19(10):673-694. doi: 10.1038/s41573-020-0075-7. Epub Aug. 11, 2020.

Roberts et al., The Halogenation of Ethylenes. J. Am. Chem. Soc. May 1937;59(5):947-8.

Sahenk et al., The muscular dystrophies: distinct pathogenic mechanisms invite novel therapeutic approaches. Curr Rheumatol Rep. Jun. 2011;13(3):199-207.

Saito et al., Antisense PMO found in dystrophic dog model was effective in cells from exon 7-deleted DMD patient. PLoS One. Aug. 18, 2010;5(8):e12239.

Samoylova et al., Elucidation of muscle-binding peptides by phage display screening. Muscle Nerve. Apr. 1999;22(4):460-6.

Sazani et al., Safety pharmacology and genotoxicity evaluation of AVI-4658. Int J Toxicol. Mar.-Apr. 2010;29(2):143-56. doi: 10.1177/1091581809359206. Epub Jan. 28, 2010.

Schneider et al., Structural features of the cell surface receptor for transferrin that is recognized by the monoclonal antibody OKT9. J Biol Chem. Jul. 25, 1982;257(14):8516-22.

(56) References Cited

OTHER PUBLICATIONS

Schnyder et al., Targeting of skeletal muscle in vitro using biotinylated immunoliposomes. Biochem J. Jan. 1, 2004;377(Pt 1):61-7. doi: 10.1042/BJ20031034.
Setten et al., The current state and future directions of RNAi-based therapeutics. Nat Rev Drug Discov. Jun. 2019;18(6):421-446. doi: 10.1038/s41573-019-0017-4.
Shen et al., Chemistry, mechanism and clinical status of antisense oligonucleotides and duplex RNAs. Nucleic Acids Res. Feb. 28, 2018;46(4):1584-1600.
Shimizu-Motohashi et al., Exon skipping for Duchenne muscular dystrophy: a systematic review and meta-analysis. Orphanet J Rare Dis. Jun. 15, 2018;13(1):93.
Singh et al., Catalytic Enantioselective Cyclopropanation of Olefins Using Carbenoid Chemistry. Synthesis. Feb. 1997;137-49.
Sklar et al., Methylprednisolone increases dystrophin levels by inhibiting myotube death during myogenesis of normal human muscle in vitro. J Neurol Sci. Jan. 1991;101(1):73-81. doi: 10.1016/0022-510x(91)90019-4.
Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.
Subramanian et al., Abstract 1074. Targeted delivery of oligonucleotide therapeutics to muscle demonstrates potential to treat duchenne muscular dystrophy. Abstract. Mol Ther. 28 (4S1): 465. (2020) 1 page.
Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.
Summerton et al . . . Morpholino antisense oligomers: design, preparation, and properties. Antisense Nucleic Acid Drug Dev. Jun. 1997;7(3):187-95.
Swayze et al., The medicinal chemistry of oligonucleotides. In: Antisense Drug Technology, Second Edition. 2007. Crooke, Ed. Chapter 6: 143-182.
Trollet et al., Gene therapy for muscular dystrophy: current progress and future prospects. Expert Opin Biol Ther. Jul. 2009;9(7):849-66.
Tron et al., Click chemistry reactions in medicinal chemistry: applications of the 1,3-dipolar cycloaddition between azides and alkynes. Med Res Rev. Mar. 2008;28(2):278-308.
Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.
Van Den Bergen et al., Forty-Five Years of Duchenne Muscular Dystrophy in The Netherlands. J Neuromuscul Dis. 2014;1(1):99-109.
Van Deutekom et al., Local dystrophin restoration with antisense oligonucleotide PRO051. N Engl J Med. Dec. 27, 2007;357(26):2677-86. doi: 10.1056/NEJMoa073108.
Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.
Wagner et al., Transferrin-polycation conjugates as carriers for DNA uptake into cells. Proc Natl Acad Sci U S A. May 1990;87(9):3410-4. doi: 10.1073/pnas.87.9.3410.
Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.
Walles et al., ADME and Safety Aspects of Non-cleavable Linkers in Drug Discovery and Development. Curr Top Med Chem. 2017;17(32):3463-3475. doi: 10.2174/1568026618666180118153502.
Wilton et al., Antisense oligonucleotide-induced exon skipping across the human dystrophin gene transcript. Mol Ther. Jul. 2007;15(7):1288-96. doi: 10.1038/sj.mt.6300095. Epub Feb. 6, 2007.
Wilton et al., Antisense oligonucleotides, exon skipping and the dystrophin gene transcript. Acta Myol. Dec. 2005;24(3):222-9.
Wilton et al., Exon skipping and Duchenne muscular dystrophy: hope, hype and how feasible? Neurol India. Jul.-Sep. 2008;56(3):254-62. doi: 10.4103/0028-3886.43443.
Wolf et al., Achieve trial, a randomized, placebo-controlled, multiple ascending dose study of Dyne-101 in individuals with myotonic dystrophy Type 1 (DM1). Abstract. Mar. 2023. 1 page.
Wolf et al., Achieve trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.
Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.
Yao et al., Targeted Delivery of ASOs Demonstrates Potential to Treat Duchenne Muscular Dystrophy. Poster. Presented at ASGCT; May 12, 2020. 1 page.
Ye et al., Generation and functional characterization of the anti-transferrin receptor single-chain antibody-GAL4 (TfRscFv-GAL4) fusion protein. BMC Biotechnol. Nov. 28, 2012;12:91.
Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.
Zanotti et al., Abstract 17. Repeat dosing with DYNE-101 is Well Tolerated and Leads to a Sustained Reduction of DMPK RNA expression in key muscles for DM1 pathology in hTfR1/DMSXL mice and NHPs. Abstract. Mol Ther. Apr. 2022; 30(4S1): 9.
Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.
Zanotti et al., Abstract 82. The ForceTM platform delivers oligonucleotides to the brain in a DM1 mouse model and in NHPs. Mol Ther. Apr. 2023; 31(4S1): 44.
Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.
Zanotti et al., DYNE-101 achieves durable knockdown of toxic human nuclear DMPK RNA and correction of splicing in the hTfR1/DMSXL mouse model of DM1. Abstract. Mar. 2022. 1 page.
Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.
Zanotti, Repeat dosing with DYNE-101 is Well Tolerated and Leads to a Sustained Reduction of DMPK RNA expression in key muscles for DM1 pathology in hTfR1/DMSXL mice and NHPs. Presented at American Society of Gene & Cell Therapy Conference. May 16, 2022. 15 pages.
Zanotti, The ForceTM platform delivers oligonucleotides to the brain in a DM1 mouse model and in NHPs. Presented at American Society of Gene & Cell Therapy Conference. May 17, 2023. 16 pages.

* cited by examiner

SEQUENCE LISTING

```
Sequence total quantity: 296
SEQ ID NO: 1              moltype = AA  length = 760
FEATURE                   Location/Qualifiers
source                    1..760
                          mol_type = protein
                          organism = Homo sapiens
SEQUENCE: 1
MMDQARSAFS NLFGGEPLSY TRFSLARQVD GDNSHVEMKL AVDEEENADN NTKANVTKPK   60
```

```
RCSGSICYGT IAVIVFFLIG FMIGYLGYCK GVEPKTECER LAGTESPVRE EPGEDFPAAR    120
RLYWDDLKRK LSEKLDSTDF TGTIKLLNEN SYVPREAGSQ KDENLALYVE NQFREFKLSK    180
VWRDQHFVKI QVKDSAQNSV IIVDKNGRLV YLVENPGGYV AYSKAATVTG KLVHANFGTK    240
KDFEDLYTPV NGSIVIVRAG KITFAEKVAN AESLNAIGVL IYMDQTKFPI VNAELSFFGH    300
AHLGTGDPYT PGFPSFNHTQ FPPSRSSGLP NIPVQTISRA AAEKLFGNME GDCPSDWKTD    360
STCRMVTSES KNVKLTVSNV LKEIKILNIF GVIKGFVEPD HYVVVGAQRD AWGPGAAKSG    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QNVHPVTGQ FLYQDSNWAS KVEKLTLDNA     540
APPFLAYSGI PAVSFCFCED TDYPYLGTTM DTYKELIERI PELNKVARAA AEVAGQFVIK    600
LTHDVELNLD YERYNSQLLS FVRDLNQYRA DIKEMGLSLQ WLYSARGDFF RATSRLTTDF    660
GNAEKTDRFV MKKLNDRVMR VEYHFLSPYV SPKESPFRHV FWGSGSHTLP ALLENLKLRK    720
QNNGAFNETL FRNQLALATW TIQGAANALS GDVWDIDNEF                         760

SEQ ID NO: 2              moltype = AA   length = 760
FEATURE                   Location/Qualifiers
source                    1..760
                          mol_type = protein
                          organism = Macaca mulatta
SEQUENCE: 2
MMDQARSAFS NLFGGEPLSY TRFSLARQVD GDNSHVEMKL GVDEEENTDN NTKPNGTKPK     60
RCGGNICYGT IAVIIFFLIG FMIGYLGYCK GVEPKTECER LAGTESPARE EPEEDFPAAP    120
RLYWDDLKRK LSEKLDTTDF TSTIKLLNEN LYVPREAGSQ KDENLALYIE NQFREFKLSK    180
VWRDQHFVKI QVKDSAQNSV IIVDKNGGLV YLVENPGGYV AYSKAATVTG KLVHANFGTK    240
KDFEDLDSPV NGSIVIVRAG KITFAEKVAN AESLNAIGVL IYMDQTKFPI VKADLSFFGH    300
AHLGTGDPYT PGFPSFNHTQ FPPSQSSGLP NIPVQTISRA AAEKLFGNME GDCPSDWKTD    360
STCKMVTSEN KSVKLTVSNV LKETKILNIF GVIKGFVEPD HYVVVGAQRD AWGPGAAKSS    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QDVKHPVTGR SLYQDSNWAS KVEKLTLDNA    540
APPFLAYSGI PAVSFCFCED TDYPYLGTTM DTYKELVERI PELNKVARAA AEVAGQFVIK    600
LTHDTELNLD YERYNSQLLL FLRDLNQYRA DVKEMGLSLQ WLYSARGDFF RATSRLTTDF    660
RNAEKRDKFV MKKLNDRVMR VEYYFLSPYV SPKESPFRHV FWGSGSHTLS ALLESLKLRR    720
QNNSAFNETL FRNQLALATW TIQGAANALS GDVWDIDNEF                         760

SEQ ID NO: 3              moltype = AA   length = 760
FEATURE                   Location/Qualifiers
source                    1..760
                          mol_type = protein
                          organism = Macaca fascicularis
SEQUENCE: 3
MMDQARSAFS NLFGGEPLSY TRFSLARQVD GDNSHVEMKL GVDEEENTDN NTKANGTKPK     60
RCGGNICYGT IAVIIFFLIG FMIGYLGYCK GVEPKTECER LAGTESPARE EPEEDFPAAP    120
RLYWDDLKRK LSEKLDTTDF TSTIKLLNEN LYVPREAGSQ KDENLALYIE NQFREFKLSK    180
VWRDQHFVKI QVKDSAQNSV IIVDKNGGLV YLVENPGGYV AYSKAATVTG KLVHANFGTK    240
KDFEDLDSPV NGSIVIVRAG KITFAEKVAN AESLNAIGVL IYMDQTKFPI VKADLSFFGH    300
AHLGTGDPYT PGFPSFNHTQ FPPSQSSGLP NIPVQTISRA AAEKLFGNME GDCPSDWKTD    360
STCKMVTSEN KSVKLTVSNV LKETKILNIF GVIKGFVEPD HYVVVGAQRD AWGPGAAKSS    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QDVKHPVTGR SLYQDSNWAS KVEKLTLDNA    540
APPFLAYSGI PAVSFCFCED TDYPYLGTTM DTYKELVERI PELNKVARAA AEVAGQFVIK    600
LTHDTELNLD YERYNSQLLL FLRDLNQYRA DVKEMGLSLQ WLYSARGDFF RATSRLTTDF    660
RNAEKRDKFV MKKLNDRVMR VEYYFLSPYV SPKESPFRHV FWGSGSHTLS ALLESLKLRR    720
QNNSAFNETL FRNQLALATW TIQGAANALS GDVWDIDNEF                         760

SEQ ID NO: 4              moltype = AA   length = 763
FEATURE                   Location/Qualifiers
source                    1..763
                          mol_type = protein
                          organism = Mus musculus
SEQUENCE: 4
MMDQARSAFS NLFGGEPLSY TRFSLARQVD GDNSHVEMKL AADEEENADN NMKASVRKPK     60
RFNGRLCFAA IALVIFFLIG FMSGYLGYCK RVEQKEECVK LAETEETDKS ETMETEDVPT    120
SSRLYWADLK TLLSEKLNSI EFADTIKQLS QNTYTPREAG SQKDESLAYY IENQFHEFKF    180
SKVWRDEHYV KIQVKSSIGQ NMVTIVQSNG NLDPVESPEG YVAFSKPTEV SGKLVHANFG    240
TKKDFEELSY SVNGSLVIVR AGEITFAEKV ANAQSFNAIG VLIYMDKNKF PVVEADLALF    300
GHAHLGTGDP YTGFPSFNH TQFPPSQSSG LPNIPVQTIS RAAAEKLFGK MEGSCPARWN     360
IDSSCKLELS QNQNVKLIVK NVLKERRILN IFGVIKGYEE PDRYVVVGAQ RDALGAGVAA    420
KSSVGTGLLL KLAQVFSDMI SKDGFRPSRS IIFASWTAGD FGAVGATEWL EGYLSSLHLK    480
APTYINLDKV VLGTSNFKVS ASPLLYTLMG KIMQDVKHPV DGKSLYRDSN WISKVEKLSF    540
DNAAYPFLAY SGIPAVSFCF CEDADYPYLG TRLDTYEALT QKVPQLNQMV RTAAEVAGQL    600
IIKLTHDVEL NLDYEMYNSK LLSFMKDLNQ FKTDIRDMGL SLQWLYSARG DYFRATSRLT    660
TDFHNAEKTN RFVMREINDR IMKVEYHFLS PYVSPRESPF RHIFWGSGSH TLSALVENLK    720
LRQKNITAFN ETLFRNQLAL ATWTIQGVAN ALSGDIWNID NEF                      763

SEQ ID NO: 5              moltype = AA   length = 197
FEATURE                   Location/Qualifiers
REGION                    1..197
                          note = Synthetic polypeptide
source                    1..197
                          mol_type = protein
```

```
                        organism = synthetic construct
SEQUENCE: 5
FVKIQVKDSA QNSVIIVDKN GRLVYLVENP GGYVAYSKAA TVTGKLVHAN FGTKKDFEDL    60
YTPVNGSIVI VRAGKITFAE KVANAESLNA IGVLIYMDQT KFPIVNAELS FFGHAHLGTG   120
DPYTPGFPSF NHTQFPPSRS SGLPNIPVQT ISRAAAEKLF GNMEGDCPSD WKTDSTCRMV   180
TSESKNVKLT VSNVLKE                                                  197

SEQ ID NO: 6            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 6
ASSLNIA                                                                7

SEQ ID NO: 7            moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 7
SKTFNTHPQS TP                                                         12

SEQ ID NO: 8            moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 8
TARGEHKEEE LI                                                         12

SEQ ID NO: 9            moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 9
CQAQGQLVC                                                              9

SEQ ID NO: 10           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 10
CSERSMNFC                                                              9

SEQ ID NO: 11           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 11
CPKTRRVPC                                                              9

SEQ ID NO: 12           moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 12
WLSEAGPVVT VRALRGTGSW                                                 20

SEQ ID NO: 13           moltype = AA  length = 9
FEATURE                 Location/Qualifiers
```

```
REGION                   1..9
                         note = Synthetic polypeptide
source                   1..9
                         mol_type = protein
                         organism = synthetic construct
SEQUENCE: 13
CMQHSMRVC                                                                  9

SEQ ID NO: 14            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 14
DDTRHWG                                                                    7

SEQ ID NO: 15            moltype = RNA  length = 19
FEATURE                  Location/Qualifiers
misc_feature             1..19
                         note = Nucleic acid
source                   1..19
                         mol_type = other RNA
                         organism = synthetic construct
SEQUENCE: 15
cttcctggat ggcttcaat                                                       19

SEQ ID NO: 16            moltype = RNA  length = 19
FEATURE                  Location/Qualifiers
misc_feature             1..19
                         note = Nucleic acid
source                   1..19
                         mol_type = other RNA
                         organism = synthetic construct
SEQUENCE: 16
gtacattaag atggacttc                                                       19

SEQ ID NO: 17            moltype = RNA  length = 30
FEATURE                  Location/Qualifiers
misc_feature             1..30
                         note = Nucleic acid
source                   1..30
                         mol_type = other RNA
                         organism = synthetic construct
SEQUENCE: 17
tatctggata ggtggtatca agatctgtaa                                           30

SEQ ID NO: 18            moltype = RNA  length = 25
FEATURE                  Location/Qualifiers
misc_feature             1..25
                         note = Nucleic acid
source                   1..25
                         mol_type = other RNA
                         organism = synthetic construct
SEQUENCE: 18
atgtaactga aaatgttctt cttta                                                25

SEQ ID NO: 19            moltype = RNA  length = 30
FEATURE                  Location/Qualifiers
misc_feature             1..30
                         note = Nucleic acid
source                   1..30
                         mol_type = other RNA
                         organism = synthetic construct
SEQUENCE: 19
tggataggtg gtatcaacat ctgtaagcac                                           30

SEQ ID NO: 20            moltype = RNA  length = 22
FEATURE                  Location/Qualifiers
misc_feature             1..22
                         note = Nucleic acid
source                   1..22
                         mol_type = other RNA
                         organism = synthetic construct
SEQUENCE: 20
gataggtggt atcaacatct gt                                                   22

SEQ ID NO: 21            moltype = RNA  length = 30
```

```
FEATURE                 Location/Qualifiers
misc_feature            1..30
                        note = Nucleic acid
source                  1..30
                        mol_type = other RNA
                        organism = synthetic construct
SEQUENCE: 21
tatctggata ggtggtatca acatctgtaa                                        30

SEQ ID NO: 22           moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 22
aaacttggaa gagtgatgtg atgta                                             25

SEQ ID NO: 23           moltype = RNA   length = 27
FEATURE                 Location/Qualifiers
misc_feature            1..27
                        note = Nucleic acid
source                  1..27
                        mol_type = other RNA
                        organism = synthetic construct
SEQUENCE: 23
gctcacttgt tgaggcaaaa cttggaa                                           27

SEQ ID NO: 24           moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 24
gccttggcaa catttccact tcctg                                             25

SEQ ID NO: 25           moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 25
tacacacttt acctgttgag aatag                                             25

SEQ ID NO: 26           moltype = RNA   length = 24
FEATURE                 Location/Qualifiers
misc_feature            1..24
                        note = Nucleic acid
source                  1..24
                        mol_type = other RNA
                        organism = synthetic construct
SEQUENCE: 26
gataggtggt atcaacatct gtaa                                              24

SEQ ID NO: 27           moltype = RNA   length = 21
FEATURE                 Location/Qualifiers
misc_feature            1..21
                        note = Nucleic acid
source                  1..21
                        mol_type = other RNA
                        organism = synthetic construct
SEQUENCE: 27
gataggtggt atcaacatct g                                                 21

SEQ ID NO: 28           moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 28
gataggtggt atcaacatct gtaag                                             25
```

```
SEQ ID NO: 29           moltype = RNA   length = 20
FEATURE                 Location/Qualifiers
misc_feature            1..20
                        note = Nucleic acid
source                  1..20
                        mol_type = other RNA
                        organism = synthetic construct
SEQUENCE: 29
ggtggtatca acatctgtaa                                                      20

SEQ ID NO: 30           moltype = RNA   length = 20
FEATURE                 Location/Qualifiers
misc_feature            1..20
                        note = Nucleic acid
source                  1..20
                        mol_type = other RNA
                        organism = synthetic construct
SEQUENCE: 30
gtatcaacat ctgtaagcac                                                      20

SEQ ID NO: 31           moltype = RNA   length = 30
FEATURE                 Location/Qualifiers
misc_feature            1..30
                        note = Nucleic acid
misc_feature            27
                        note = n can be any nucleouide
source                  1..30
                        mol_type = other RNA
                        organism = synthetic construct
SEQUENCE: 31
cggctaattt cagagggcgc tttcttngac                                           30

SEQ ID NO: 32           moltype = RNA   length = 26
FEATURE                 Location/Qualifiers
misc_feature            1..26
                        note = Nucleic acid
source                  1..26
                        mol_type = other RNA
                        organism = synthetic construct
SEQUENCE: 32
acagtggtgc tgagatagta taggcc                                               26

SEQ ID NO: 33           moltype = RNA   length = 22
FEATURE                 Location/Qualifiers
misc_feature            1..22
                        note = Nucleic acid
source                  1..22
                        mol_type = other RNA
                        organism = synthetic construct
SEQUENCE: 33
taggccactt tgttgctctt gc                                                   22

SEQ ID NO: 34           moltype = RNA   length = 19
FEATURE                 Location/Qualifiers
misc_feature            1..19
                        note = Nucleic acid
source                  1..19
                        mol_type = other RNA
                        organism = synthetic construct
SEQUENCE: 34
ttcagagggc gctttcttc                                                       19

SEQ ID NO: 35           moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 35
tcttcaggtg caccttctgt ttctcaatct                                           30

SEQ ID NO: 36           moltype = RNA   length = 30
FEATURE                 Location/Qualifiers
misc_feature            1..30
                        note = Nucleic acid
source                  1..30
                        mol_type = other RNA
                        organism = synthetic construct
```

```
SEQUENCE: 36
tctgtgatac tcttcaggtg caccttctgt                                        30

SEQ ID NO: 37           moltype = RNA  length = 21
FEATURE                 Location/Qualifiers
misc_feature            1..21
                        note = Nucleic acid
source                  1..21
                        mol_type = other RNA
                        organism = synthetic construct
SEQUENCE: 37
tcttctgctc gggaggtgac a                                                 21

SEQ ID NO: 38           moltype = RNA  length = 20
FEATURE                 Location/Qualifiers
misc_feature            1..20
                        note = Nucleic acid
source                  1..20
                        mol_type = other RNA
                        organism = synthetic construct
SEQUENCE: 38
ccagttacta ttcagaagac                                                   20

SEQ ID NO: 39           moltype = RNA  length = 20
FEATURE                 Location/Qualifiers
misc_feature            1..20
                        note = Nucleic acid
source                  1..20
                        mol_type = other RNA
                        organism = synthetic construct
SEQUENCE: 39
tcttcaggtg caccttctgt                                                   20

SEQ ID NO: 40           moltype = RNA  length = 18
FEATURE                 Location/Qualifiers
misc_feature            1..18
                        note = Nucleic acid
source                  1..18
                        mol_type = other RNA
                        organism = synthetic construct
SEQUENCE: 40
tgctgctgtc ttcttgct                                                     18

SEQ ID NO: 41           moltype = RNA  length = 19
FEATURE                 Location/Qualifiers
misc_feature            1..19
                        note = Nucleic acid
source                  1..19
                        mol_type = other RNA
                        organism = synthetic construct
SEQUENCE: 41
ttgttaactt tttcccatt                                                    19

SEQ ID NO: 42           moltype = RNA  length = 20
FEATURE                 Location/Qualifiers
misc_feature            1..20
                        note = Nucleic acid
source                  1..20
                        mol_type = other RNA
                        organism = synthetic construct
SEQUENCE: 42
tgttaacttt ttcccattgg                                                   20

SEQ ID NO: 43           moltype = RNA  length = 20
FEATURE                 Location/Qualifiers
misc_feature            1..20
                        note = Nucleic acid
source                  1..20
                        mol_type = other RNA
                        organism = synthetic construct
SEQUENCE: 43
cattttgtta acttttccc                                                    20

SEQ ID NO: 44           moltype = RNA  length = 19
FEATURE                 Location/Qualifiers
misc_feature            1..19
                        note = Nucleic acid
source                  1..19
                        mol_type = other RNA
```

```
                        organism = synthetic construct
SEQUENCE: 44
ctgtagcttc acccttttcc                                                       19

SEQ ID NO: 45           moltype = RNA  length = 26
FEATURE                 Location/Qualifiers
misc_feature            1..26
                        note = Nucleic acid
source                  1..26
                        mol_type = other RNA
                        organism = synthetic construct
SEQUENCE: 45
gagagcttcc tgtagcttca cccttt                                                26

SEQ ID NO: 46           moltype = RNA  length = 28
FEATURE                 Location/Qualifiers
misc_feature            1..28
                        note = Nucleic acid
source                  1..28
                        mol_type = other RNA
                        organism = synthetic construct
SEQUENCE: 46
tcctgtagct tcacccttttc cacaggcg                                             28

SEQ ID NO: 47           moltype = RNA  length = 20
FEATURE                 Location/Qualifiers
misc_feature            1..20
                        note = Nucleic acid
source                  1..20
                        mol_type = other RNA
                        organism = synthetic construct
SEQUENCE: 47
tgtgttacct acccttgtcg                                                       20

SEQ ID NO: 48           moltype = RNA  length = 27
FEATURE                 Location/Qualifiers
misc_feature            1..27
                        note = Nucleic acid
source                  1..27
                        mol_type = other RNA
                        organism = synthetic construct
SEQUENCE: 48
tagactatct tttatattct gtaatat                                               27

SEQ ID NO: 49           moltype = RNA  length = 29
FEATURE                 Location/Qualifiers
misc_feature            1..29
                        note = Nucleic acid
source                  1..29
                        mol_type = other RNA
                        organism = synthetic construct
SEQUENCE: 49
gagagcttcc tgtagcttca ccctttcca                                             29

SEQ ID NO: 50           moltype = RNA  length = 31
FEATURE                 Location/Qualifiers
misc_feature            1..31
                        note = Nucleic acid
source                  1..31
                        mol_type = other RNA
                        organism = synthetic construct
SEQUENCE: 50
ttcctgtagc ttcacccttt ccacaggcgt t                                          31

SEQ ID NO: 51           moltype = RNA  length = 23
FEATURE                 Location/Qualifiers
misc_feature            1..23
                        note = Nucleic acid
source                  1..23
                        mol_type = other RNA
                        organism = synthetic construct
SEQUENCE: 51
agcttcctgt agcttcaccc ttt                                                   23

SEQ ID NO: 52           moltype = RNA  length = 29
FEATURE                 Location/Qualifiers
misc_feature            1..29
                        note = Nucleic acid
source                  1..29
```

```
                            mol_type = other RNA
                            organism = synthetic construct
SEQUENCE: 52
ggagagagct tcctgtagct tcacccttt                                            29

SEQ ID NO: 53               moltype = RNA   length = 23
FEATURE                     Location/Qualifiers
misc_feature                1..23
                            note = Nucleic acid
source                      1..23
                            mol_type = other RNA
                            organism = synthetic construct
SEQUENCE: 53
gagagcttcc tgtagcttca ccc                                                  23

SEQ ID NO: 54               moltype = RNA   length = 25
FEATURE                     Location/Qualifiers
misc_feature                1..25
                            note = Nucleic acid
source                      1..25
                            mol_type = other RNA
                            organism = synthetic construct
SEQUENCE: 54
tatgtgttac ctaccttgt cggtc                                                 25

SEQ ID NO: 55               moltype = RNA   length = 20
FEATURE                     Location/Qualifiers
misc_feature                1..20
                            note = Nucleic acid
source                      1..20
                            mol_type = other RNA
                            organism = synthetic construct
SEQUENCE: 55
ggagagagct tcctgtagct                                                      20

SEQ ID NO: 56               moltype = RNA   length = 23
FEATURE                     Location/Qualifiers
misc_feature                1..23
                            note = Nucleic acid
source                      1..23
                            mol_type = other RNA
                            organism = synthetic construct
SEQUENCE: 56
tcacccttc cacaggcgtt gca                                                   23

SEQ ID NO: 57               moltype = RNA   length = 28
FEATURE                     Location/Qualifiers
misc_feature                1..28
                            note = Nucleic acid
source                      1..28
                            mol_type = other RNA
                            organism = synthetic construct
SEQUENCE: 57
gctgggagag agcttcctgt agcttcac                                             28

SEQ ID NO: 58               moltype = RNA   length = 28
FEATURE                     Location/Qualifiers
misc_feature                1..28
                            note = Nucleic acid
source                      1..28
                            mol_type = other RNA
                            organism = synthetic construct
SEQUENCE: 58
tgttacctac ccttgtcggt ccttgtac                                             28

SEQ ID NO: 59               moltype = RNA   length = 28
FEATURE                     Location/Qualifiers
misc_feature                1..28
                            note = Nucleic acid
source                      1..28
                            mol_type = other RNA
                            organism = synthetic construct
SEQUENCE: 59
ctgctgtctt cttgctatga ataatgtc                                             28

SEQ ID NO: 60               moltype = RNA   length = 28
FEATURE                     Location/Qualifiers
misc_feature                1..28
                            note = Nucleic acid
```

```
source                    1..28
                          mol_type = other RNA
                          organism = synthetic construct
SEQUENCE: 60
ggcgttgcac tttgcaatgc tgctgtct                                        28

SEQ ID NO: 61             moltype = RNA  length = 28
FEATURE                   Location/Qualifiers
misc_feature              1..28
                          note = Nucleic acid
source                    1..28
                          mol_type = other RNA
                          organism = synthetic construct
SEQUENCE: 61
ttggaaatca agctgggaga gagcttcc                                        28

SEQ ID NO: 62             moltype = RNA  length = 28
FEATURE                   Location/Qualifiers
misc_feature              1..28
                          note = Nucleic acid
source                    1..28
                          mol_type = other RNA
                          organism = synthetic construct
SEQUENCE: 62
ctaccctTgt cggtccttgt acattttg                                        28

SEQ ID NO: 63             moltype = RNA  length = 28
FEATURE                   Location/Qualifiers
misc_feature              1..28
                          note = Nucleic acid
source                    1..28
                          mol_type = other RNA
                          organism = synthetic construct
SEQUENCE: 63
gtcaatccga cctgagcttt gttgtaga                                        28

SEQ ID NO: 64             moltype = RNA  length = 27
FEATURE                   Location/Qualifiers
misc_feature              1..27
                          note = Nucleic acid
source                    1..27
                          mol_type = other RNA
                          organism = synthetic construct
SEQUENCE: 64
cttgctatga ataatgtcaa tccgacc                                         27

SEQ ID NO: 65             moltype = RNA  length = 28
FEATURE                   Location/Qualifiers
misc_feature              1..28
                          note = Nucleic acid
source                    1..28
                          mol_type = other RNA
                          organism = synthetic construct
SEQUENCE: 65
tatatgtgtt acctaccctt gtcggtcc                                        28

SEQ ID NO: 66             moltype = RNA  length = 20
FEATURE                   Location/Qualifiers
misc_feature              1..20
                          note = Nucleic acid
source                    1..20
                          mol_type = other RNA
                          organism = synthetic construct
SEQUENCE: 66
tttgtgtctt tctgagaaac                                                 20

SEQ ID NO: 67             moltype = RNA  length = 20
FEATURE                   Location/Qualifiers
misc_feature              1..20
                          note = Nucleic acid
source                    1..20
                          mol_type = other RNA
                          organism = synthetic construct
SEQUENCE: 67
aaagacttac cttaagatac                                                 20

SEQ ID NO: 68             moltype = RNA  length = 20
FEATURE                   Location/Qualifiers
misc_feature              1..20
```

```
                          note = Nucleic acid
source                    1..20
                          mol_type = other RNA
                          organism = synthetic construct
SEQUENCE: 68
atctgtcaaa tcgcctgcag                                                      20

SEQ ID NO: 69             moltype = RNA   length = 19
FEATURE                   Location/Qualifiers
misc_feature              1..19
                          note = Nucleic acid
source                    1..19
                          mol_type = other RNA
                          organism = synthetic construct
SEQUENCE: 69
cgccgccatt tctcaacag                                                       19

SEQ ID NO: 70             moltype = RNA   length = 20
FEATURE                   Location/Qualifiers
misc_feature              1..20
                          note = Nucleic acid
source                    1..20
                          mol_type = other RNA
                          organism = synthetic construct
SEQUENCE: 70
tttgtattta gcatgttccc                                                      20

SEQ ID NO: 71             moltype = RNA   length = 17
FEATURE                   Location/Qualifiers
misc_feature              1..17
                          note = Nucleic acid
source                    1..17
                          mol_type = other RNA
                          organism = synthetic construct
SEQUENCE: 71
ccgccatttc tcaacag                                                         17

SEQ ID NO: 72             moltype = RNA   length = 21
FEATURE                   Location/Qualifiers
misc_feature              1..21
                          note = Nucleic acid
source                    1..21
                          mol_type = other RNA
                          organism = synthetic construct
SEQUENCE: 72
ttctcaggaa tttgtgtctt t                                                    21

SEQ ID NO: 73             moltype = RNA   length = 11
FEATURE                   Location/Qualifiers
misc_feature              1..11
                          note = Nucleic acid
source                    1..11
                          mol_type = other RNA
                          organism = synthetic construct
SEQUENCE: 73
gacaactctt t                                                               11

SEQ ID NO: 74             moltype = RNA   length = 20
FEATURE                   Location/Qualifiers
misc_feature              1..20
                          note = Nucleic acid
source                    1..20
                          mol_type = other RNA
                          organism = synthetic construct
SEQUENCE: 74
tcagcttctg ttagccactg                                                      20

SEQ ID NO: 75             moltype = RNA   length = 24
FEATURE                   Location/Qualifiers
misc_feature              1..24
                          note = Nucleic acid
source                    1..24
                          mol_type = other RNA
                          organism = synthetic construct
SEQUENCE: 75
tgttcagctt ctgttagcca ctga                                                 24

SEQ ID NO: 76             moltype = RNA   length = 27
FEATURE                   Location/Qualifiers
```

```
                            -continued misc_feature            1..27
                        note = Nucleic acid
source                  1..27
                        mol_type = other RNA
                        organism = synthetic construct
SEQUENCE: 76
ctgttcagct tctgttagcc actgatt                                              27

SEQ ID NO: 77           moltype = RNA  length = 30
FEATURE                 Location/Qualifiers
misc_feature            1..30
                        note = Nucleic acid
source                  1..30
                        mol_type = other RNA
                        organism = synthetic construct
SEQUENCE: 77
ttctcaacag atctgtcaaa tcgcctgcag                                           30

SEQ ID NO: 78           moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 78
gccactgatt aaatatcttt atatc                                                25

SEQ ID NO: 79           moltype = RNA  length = 30
FEATURE                 Location/Qualifiers
misc_feature            1..30
                        note = Nucleic acid
source                  1..30
                        mol_type = other RNA
                        organism = synthetic construct
SEQUENCE: 79
tctgttagcc actgattaaa tatctttata                                           30

SEQ ID NO: 80           moltype = RNA  length = 31
FEATURE                 Location/Qualifiers
misc_feature            1..31
                        note = Nucleic acid
source                  1..31
                        mol_type = other RNA
                        organism = synthetic construct
SEQUENCE: 80
gagaaactgt tcagcttctg ttagccactg a                                         31

SEQ ID NO: 81           moltype = RNA  length = 31
FEATURE                 Location/Qualifiers
misc_feature            1..31
                        note = Nucleic acid
source                  1..31
                        mol_type = other RNA
                        organism = synthetic construct
SEQUENCE: 81
tctttctgag aaactgttca gcttctgtta g                                         31

SEQ ID NO: 82           moltype = RNA  length = 26
FEATURE                 Location/Qualifiers
misc_feature            1..26
                        note = Nucleic acid
source                  1..26
                        mol_type = other RNA
                        organism = synthetic construct
SEQUENCE: 82
cagatctgtc aaatcgcctg caggta                                               26

SEQ ID NO: 83           moltype = RNA  length = 26
FEATURE                 Location/Qualifiers
misc_feature            1..26
                        note = Nucleic acid
source                  1..26
                        mol_type = other RNA
                        organism = synthetic construct
SEQUENCE: 83
caacagatct gtcaaatcgc ctgcag                                               26

SEQ ID NO: 84           moltype = RNA  length = 33
```

```
FEATURE                 Location/Qualifiers
misc_feature            1..33
                        note = Nucleic acid
source                  1..33
                        mol_type = other RNA
                        organism = synthetic construct
SEQUENCE: 84
aaactgttca gcttctgtta gccactgatt aaa                                    33

SEQ ID NO: 85           moltype = RNA   length = 31
FEATURE                 Location/Qualifiers
misc_feature            1..31
                        note = Nucleic acid
source                  1..31
                        mol_type = other RNA
                        organism = synthetic construct
SEQUENCE: 85
gaaactgttc agcttctgtt agccactgat t                                      31

SEQ ID NO: 86           moltype = RNA   length = 28
FEATURE                 Location/Qualifiers
misc_feature            1..28
                        note = Nucleic acid
source                  1..28
                        mol_type = other RNA
                        organism = synthetic construct
SEQUENCE: 86
aaactgttca gcttctgtta gccactga                                          28

SEQ ID NO: 87           moltype = RNA   length = 28
FEATURE                 Location/Qualifiers
misc_feature            1..28
                        note = Nucleic acid
source                  1..28
                        mol_type = other RNA
                        organism = synthetic construct
SEQUENCE: 87
tgagaaactg ttcagcttct gttagcca                                          28

SEQ ID NO: 88           moltype = RNA   length = 32
FEATURE                 Location/Qualifiers
misc_feature            1..32
                        note = Nucleic acid
source                  1..32
                        mol_type = other RNA
                        organism = synthetic construct
SEQUENCE: 88
ttctgagaaa ctgttcagct tctgttagcc ac                                     32

SEQ ID NO: 89           moltype = RNA   length = 26
FEATURE                 Location/Qualifiers
misc_feature            1..26
                        note = Nucleic acid
source                  1..26
                        mol_type = other RNA
                        organism = synthetic construct
SEQUENCE: 89
ttctgagaaa ctgttcagct tctgtt                                            26

SEQ ID NO: 90           moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 90
gatctgtcaa atcgcctgca ggtaa                                             25

SEQ ID NO: 91           moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 91
ataatgaaaa cgccgccatt tctca                                             25
```

```
SEQ ID NO: 92              moltype = RNA   length = 25
FEATURE                    Location/Qualifiers
misc_feature               1..25
                           note = Nucleic acid
source                     1..25
                           mol_type = other RNA
                           organism = synthetic construct
SEQUENCE: 92
aaactgttca gcttctgtta gccac                                               25

SEQ ID NO: 93              moltype = RNA   length = 25
FEATURE                    Location/Qualifiers
misc_feature               1..25
                           note = Nucleic acid
source                     1..25
                           mol_type = other RNA
                           organism = synthetic construct
SEQUENCE: 93
ttgtgtcttt ctgagaaact gttca                                               25

SEQ ID NO: 94              moltype = RNA   length = 25
FEATURE                    Location/Qualifiers
misc_feature               1..25
                           note = Nucleic acid
source                     1..25
                           mol_type = other RNA
                           organism = synthetic construct
SEQUENCE: 94
ccaattctca ggaatttgtg tcttt                                               25

SEQ ID NO: 95              moltype = RNA   length = 25
FEATURE                    Location/Qualifiers
misc_feature               1..25
                           note = Nucleic acid
source                     1..25
                           mol_type = other RNA
                           organism = synthetic construct
SEQUENCE: 95
atcgcctgca ggtaaaagca tatgg                                               25

SEQ ID NO: 96              moltype = RNA   length = 30
FEATURE                    Location/Qualifiers
misc_feature               1..30
                           note = Nucleic acid
source                     1..30
                           mol_type = other RNA
                           organism = synthetic construct
SEQUENCE: 96
tgaaaacgcc gccatttctc aacagatctg                                          30

SEQ ID NO: 97              moltype = RNA   length = 30
FEATURE                    Location/Qualifiers
misc_feature               1..30
                           note = Nucleic acid
source                     1..30
                           mol_type = other RNA
                           organism = synthetic construct
SEQUENCE: 97
cataatgaaa acgccgccat ttctcaacag                                          30

SEQ ID NO: 98              moltype = RNA   length = 30
FEATURE                    Location/Qualifiers
misc_feature               1..30
                           note = Nucleic acid
source                     1..30
                           mol_type = other RNA
                           organism = synthetic construct
SEQUENCE: 98
tgttcagctt ctgttagcca ctgattaaat                                          30

SEQ ID NO: 99              moltype = RNA   length = 24
FEATURE                    Location/Qualifiers
misc_feature               1..24
                           note = Nucleic acid
source                     1..24
                           mol_type = other RNA
                           organism = synthetic construct
SEQUENCE: 99
cagatctgtc aaatcgcctg cagg                                                24
```

```
SEQ ID NO: 100          moltype = RNA   length = 27
FEATURE                 Location/Qualifiers
misc_feature            1..27
                        note = Nucleic acid
source                  1..27
                        mol_type = other RNA
                        organism = synthetic construct
SEQUENCE: 100
caacagatct gtcaaatcgc ctgcagg                                       27

SEQ ID NO: 101          moltype = RNA   length = 29
FEATURE                 Location/Qualifiers
misc_feature            1..29
                        note = Nucleic acid
source                  1..29
                        mol_type = other RNA
                        organism = synthetic construct
SEQUENCE: 101
ctcaacagat ctgtcaaatc gcctgcagg                                     29

SEQ ID NO: 102          moltype = RNA   length = 23
FEATURE                 Location/Qualifiers
misc_feature            1..23
                        note = Nucleic acid
source                  1..23
                        mol_type = other RNA
                        organism = synthetic construct
SEQUENCE: 102
gatctgtcaa atcgcctgca ggt                                           23

SEQ ID NO: 103          moltype = RNA   length = 22
FEATURE                 Location/Qualifiers
misc_feature            1..22
                        note = Nucleic acid
source                  1..22
                        mol_type = other RNA
                        organism = synthetic construct
SEQUENCE: 103
gatctgtcaa atcgcctgca gg                                            22

SEQ ID NO: 104          moltype = RNA   length = 21
FEATURE                 Location/Qualifiers
misc_feature            1..21
                        note = Nucleic acid
source                  1..21
                        mol_type = other RNA
                        organism = synthetic construct
SEQUENCE: 104
gatctgtcaa atcgcctgca g                                             21

SEQ ID NO: 105          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 105
cagatctgtc aaatcgcctg caggt                                         25

SEQ ID NO: 106          moltype = RNA   length = 23
FEATURE                 Location/Qualifiers
misc_feature            1..23
                        note = Nucleic acid
source                  1..23
                        mol_type = other RNA
                        organism = synthetic construct
SEQUENCE: 106
cagatctgtc aaatcgcctg cag                                           23

SEQ ID NO: 107          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 107
```

```
gtgtctttct gagaaactgt tcagc                                                    25

SEQ ID NO: 108           moltype = RNA   length = 28
FEATURE                  Location/Qualifiers
misc_feature             1..28
                         note = Nucleic acid
source                   1..28
                         mol_type = other RNA
                         organism = synthetic construct
SEQUENCE: 108
gagaaactgt tcagcttctg ttagccac                                                 28

SEQ ID NO: 109           moltype = RNA   length = 28
FEATURE                  Location/Qualifiers
misc_feature             1..28
                         note = Nucleic acid
source                   1..28
                         mol_type = other RNA
                         organism = synthetic construct
SEQUENCE: 109
gaaactgttc agcttctgtt agccactg                                                 28

SEQ ID NO: 110           moltype = RNA   length = 24
FEATURE                  Location/Qualifiers
misc_feature             1..24
                         note = Nucleic acid
source                   1..24
                         mol_type = other RNA
                         organism = synthetic construct
SEQUENCE: 110
ctgttcagct tctgttagcc actg                                                     24

SEQ ID NO: 111           moltype = RNA   length = 27
FEATURE                  Location/Qualifiers
misc_feature             1..27
                         note = Nucleic acid
source                   1..27
                         mol_type = other RNA
                         organism = synthetic construct
SEQUENCE: 111
atctgtcaaa tcgcctgcag gtaaaag                                                  27

SEQ ID NO: 112           moltype = RNA   length = 29
FEATURE                  Location/Qualifiers
misc_feature             1..29
                         note = Nucleic acid
source                   1..29
                         mol_type = other RNA
                         organism = synthetic construct
SEQUENCE: 112
gatctgtcaa atcgcctgca ggtaaaagc                                                29

SEQ ID NO: 113           moltype = RNA   length = 19
FEATURE                  Location/Qualifiers
misc_feature             1..19
                         note = Nucleic acid
source                   1..19
                         mol_type = other RNA
                         organism = synthetic construct
SEQUENCE: 113
gctgaattat ttcttcccc                                                           19

SEQ ID NO: 114           moltype = RNA   length = 19
FEATURE                  Location/Qualifiers
misc_feature             1..19
                         note = Nucleic acid
source                   1..19
                         mol_type = other RNA
                         organism = synthetic construct
SEQUENCE: 114
tttttctgtc tgacagctg                                                           19

SEQ ID NO: 115           moltype = RNA   length = 18
FEATURE                  Location/Qualifiers
misc_feature             1..18
                         note = Nucleic acid
source                   1..18
                         mol_type = other RNA
                         organism = synthetic construct
```

| SEQUENCE: 115 | | |
| --- | --- | --- |
| tctgttttg aggattgc | | 18 |

| SEQ ID NO: 116 | moltype = RNA length = 17 | |
| --- | --- | --- |
| FEATURE | Location/Qualifiers | |
| misc_feature | 1..17 | |
| | note = Nucleic acid | |
| source | 1..17 | |
| | mol_type = other RNA | |
| | organism = synthetic construct | |
| SEQUENCE: 116 | | |
| ccaccgcaga ttcaggc | | 17 |

| SEQ ID NO: 117 | moltype = RNA length = 17 | |
| --- | --- | --- |
| FEATURE | Location/Qualifiers | |
| misc_feature | 1..17 | |
| | note = Nucleic acid | |
| source | 1..17 | |
| | mol_type = other RNA | |
| | organism = synthetic construct | |
| SEQUENCE: 117 | | |
| gcccaatgcc atcctgg | | 17 |

| SEQ ID NO: 118 | moltype = RNA length = 17 | |
| --- | --- | --- |
| FEATURE | Location/Qualifiers | |
| misc_feature | 1..17 | |
| | note = Nucleic acid | |
| source | 1..17 | |
| | mol_type = other RNA | |
| | organism = synthetic construct | |
| SEQUENCE: 118 | | |
| tttgcagacc tcctgcc | | 17 |

| SEQ ID NO: 119 | moltype = RNA length = 17 | |
| --- | --- | --- |
| FEATURE | Location/Qualifiers | |
| misc_feature | 1..17 | |
| | note = Nucleic acid | |
| source | 1..17 | |
| | mol_type = other RNA | |
| | organism = synthetic construct | |
| SEQUENCE: 119 | | |
| cagtttgccg ctgccca | | 17 |

| SEQ ID NO: 120 | moltype = RNA length = 20 | |
| --- | --- | --- |
| FEATURE | Location/Qualifiers | |
| misc_feature | 1..20 | |
| | note = Nucleic acid | |
| source | 1..20 | |
| | mol_type = other RNA | |
| | organism = synthetic construct | |
| SEQUENCE: 120 | | |
| gttgcattca atgttctgac | | 20 |

| SEQ ID NO: 121 | moltype = RNA length = 21 | |
| --- | --- | --- |
| FEATURE | Location/Qualifiers | |
| misc_feature | 1..21 | |
| | note = Nucleic acid | |
| source | 1..21 | |
| | mol_type = other RNA | |
| | organism = synthetic construct | |
| SEQUENCE: 121 | | |
| atttttcctg tagaatactg g | | 21 |

| SEQ ID NO: 122 | moltype = RNA length = 34 | |
| --- | --- | --- |
| FEATURE | Location/Qualifiers | |
| misc_feature | 1..34 | |
| | note = Nucleic acid | |
| source | 1..34 | |
| | mol_type = other RNA | |
| | organism = synthetic construct | |
| SEQUENCE: 122 | | |
| gctgcccaat gcgatcctgg agttcctgta agat | | 34 |

| SEQ ID NO: 123 | moltype = RNA length = 28 | |
| --- | --- | --- |
| FEATURE | Location/Qualifiers | |
| misc_feature | 1..28 | |
| | note = Nucleic acid | |
| source | 1..28 | |
| | mol_type = other RNA | |

```
                            organism = synthetic construct
SEQUENCE: 123
gctgcccaat gccatcctgg agttcctg                                        28

SEQ ID NO: 124          moltype = RNA   length = 31
FEATURE                 Location/Qualifiers
misc_feature            1..31
                        note = Nucleic acid
source                  1..31
                        mol_type = other RNA
                        organism = synthetic construct
SEQUENCE: 124
gctgcccaat gccatcctgg agttcctgta a                                    31

SEQ ID NO: 125          moltype = RNA   length = 31
FEATURE                 Location/Qualifiers
misc_feature            1..31
                        note = Nucleic acid
source                  1..31
                        mol_type = other RNA
                        organism = synthetic construct
SEQUENCE: 125
caatgccatc ctggagttcc tgtaagatac c                                    31

SEQ ID NO: 126          moltype = RNA   length = 32
FEATURE                 Location/Qualifiers
misc_feature            1..32
                        note = Nucleic acid
source                  1..32
                        mol_type = other RNA
                        organism = synthetic construct
SEQUENCE: 126
gctgcccaat gccatcctgg agttcctgta ag                                   32

SEQ ID NO: 127          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 127
ccaatgccat cctggagttc ctgtaagata                                      30

SEQ ID NO: 128          moltype = RNA   length = 39
FEATURE                 Location/Qualifiers
misc_feature            1..39
                        note = Nucleic acid
source                  1..39
                        mol_type = other RNA
                        organism = synthetic construct
SEQUENCE: 128
ttgccgctgc ccaatgccat cctggagttc ctgtaagat                            39

SEQ ID NO: 129          moltype = RNA   length = 34
FEATURE                 Location/Qualifiers
misc_feature            1..34
                        note = Nucleic acid
source                  1..34
                        mol_type = other RNA
                        organism = synthetic construct
SEQUENCE: 129
gctgcccaat gccatcctgg agttcctgta agat                                 34

SEQ ID NO: 130          moltype = RNA   length = 27
FEATURE                 Location/Qualifiers
misc_feature            1..27
                        note = Nucleic acid
source                  1..27
                        mol_type = other RNA
                        organism = synthetic construct
SEQUENCE: 130
caatgccatc ctggagttcc tgtaaga                                         27

SEQ ID NO: 131          moltype = RNA   length = 26
FEATURE                 Location/Qualifiers
misc_feature            1..26
                        note = Nucleic acid
source                  1..26
```

```
                         mol_type = other RNA
                         organism = synthetic construct
SEQUENCE: 131
cagtttgccg ctgcccaatg ccatcc                                            26

SEQ ID NO: 132          moltype = RNA   length = 24
FEATURE                 Location/Qualifiers
misc_feature            1..24
                        note = Nucleic acid
source                  1..24
                        mol_type = other RNA
                        organism = synthetic construct
SEQUENCE: 132
cttccccagt tgcattcaat gttc                                              24

SEQ ID NO: 133          moltype = RNA   length = 23
FEATURE                 Location/Qualifiers
misc_feature            1..23
                        note = Nucleic acid
source                  1..23
                        mol_type = other RNA
                        organism = synthetic construct
SEQUENCE: 133
ctggcatctg tttttgagga ttg                                               23

SEQ ID NO: 134          moltype = RNA   length = 20
FEATURE                 Location/Qualifiers
misc_feature            1..20
                        note = Nucleic acid
source                  1..20
                        mol_type = other RNA
                        organism = synthetic construct
SEQUENCE: 134
ttagatctgt cgccctacct                                                   20

SEQ ID NO: 135          moltype = RNA   length = 39
FEATURE                 Location/Qualifiers
misc_feature            1..39
                        note = Nucleic acid
source                  1..39
                        mol_type = other RNA
                        organism = synthetic construct
SEQUENCE: 135
gctgcccaat gccatcctgg agttcctgta agataccaa                              39

SEQ ID NO: 136          moltype = RNA   length = 34
FEATURE                 Location/Qualifiers
misc_feature            1..34
                        note = Nucleic acid
source                  1..34
                        mol_type = other RNA
                        organism = synthetic construct
SEQUENCE: 136
gcccaatgcc atcctggagt tcctgtaaga tacc                                   34

SEQ ID NO: 137          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 137
catcctggag ttcctgtaag atacc                                             25

SEQ ID NO: 138          moltype = RNA   length = 28
FEATURE                 Location/Qualifiers
misc_feature            1..28
                        note = Nucleic acid
source                  1..28
                        mol_type = other RNA
                        organism = synthetic construct
SEQUENCE: 138
tgccatcctg gagttcctgt aagatacc                                          28

SEQ ID NO: 139          moltype = RNA   length = 25
FEATURE                 Location/Qualifiers
misc_feature            1..25
                        note = Nucleic acid
```

```
                       source          1..25
                                       mol_type = other RNA
                                       organism = synthetic construct
SEQUENCE: 139
tgccatcctg gagttcctgt aagat                                                 25

SEQ ID NO: 140         moltype = RNA   length = 28
FEATURE                Location/Qualifiers
misc_feature           1..28
                       note = Nucleic acid
source                 1..28
                       mol_type = other RNA
                       organism = synthetic construct
SEQUENCE: 140
caatgccatc ctggagttcc tgtaagat                                              28

SEQ ID NO: 141         moltype = RNA   length = 31
FEATURE                Location/Qualifiers
misc_feature           1..31
                       note = Nucleic acid
source                 1..31
                       mol_type = other RNA
                       organism = synthetic construct
SEQUENCE: 141
gcccaatgcc atcctggagt tcctgtaaga t                                          31

SEQ ID NO: 142         moltype = RNA   length = 28
FEATURE                Location/Qualifiers
misc_feature           1..28
                       note = Nucleic acid
source                 1..28
                       mol_type = other RNA
                       organism = synthetic construct
SEQUENCE: 142
gcccaatgcc atcctggagt tcctgtaa                                              28

SEQ ID NO: 143         moltype = RNA   length = 34
FEATURE                Location/Qualifiers
misc_feature           1..34
                       note = Nucleic acid
source                 1..34
                       mol_type = other RNA
                       organism = synthetic construct
SEQUENCE: 143
gccgctgccc aatgacatcc tggagttcct gtaa                                       34

SEQ ID NO: 144         moltype = RNA   length = 25
FEATURE                Location/Qualifiers
misc_feature           1..25
                       note = Nucleic acid
source                 1..25
                       mol_type = other RNA
                       organism = synthetic construct
SEQUENCE: 144
gccatcctgg agttcctgta agata                                                 25

SEQ ID NO: 145         moltype = RNA   length = 25
FEATURE                Location/Qualifiers
misc_feature           1..25
                       note = Nucleic acid
source                 1..25
                       mol_type = other RNA
                       organism = synthetic construct
SEQUENCE: 145
ccaatgccat cctggagttc ctgta                                                 25

SEQ ID NO: 146         moltype = RNA   length = 25
FEATURE                Location/Qualifiers
misc_feature           1..25
                       note = Nucleic acid
source                 1..25
                       mol_type = other RNA
                       organism = synthetic construct
SEQUENCE: 146
ctgacaacag tttgccgctg cccaa                                                 25

SEQ ID NO: 147         moltype = RNA   length = 25
FEATURE                Location/Qualifiers
misc_feature           1..25
```

```
                        note = Nucleic acid
source                  1..25
                        mol_type = other RNA
                        organism = synthetic construct
SEQUENCE: 147
tttgaggatt gctgaattat ttctt                                         25

SEQ ID NO: 148          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 148
cagtttgccg ctgcccaatg ccatcctgga                                    30

SEQ ID NO: 149          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 149
ttgccgctgc ccaatgccat cctggagttc                                    30

SEQ ID NO: 150          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 150
tttgccgctg cccaatgcca tcctg                                         25

SEQ ID NO: 151          moltype = RNA   length = 22
FEATURE                 Location/Qualifiers
misc_feature            1..22
                        note = Nucleic acid
source                  1..22
                        mol_type = other RNA
                        organism = synthetic construct
SEQUENCE: 151
ccaatgccat cctggagttc ct                                            22

SEQ ID NO: 152          moltype = RNA   length = 29
FEATURE                 Location/Qualifiers
misc_feature            1..29
                        note = Nucleic acid
source                  1..29
                        mol_type = other RNA
                        organism = synthetic construct
SEQUENCE: 152
cccaatgcca tcctggagtt cctgtaaga                                     29

SEQ ID NO: 153          moltype = RNA   length = 28
FEATURE                 Location/Qualifiers
misc_feature            1..28
                        note = Nucleic acid
source                  1..28
                        mol_type = other RNA
                        organism = synthetic construct
SEQUENCE: 153
ccgctgccca atgccatcct ggagttcc                                      28

SEQ ID NO: 154          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 154
cccaatgcca tcctggagtt cctgtaagat                                    30

SEQ ID NO: 155          moltype = RNA   length = 30
FEATURE                 Location/Qualifiers
```

```
misc_feature              1..30
                          note = Nucleic acid
source                    1..30
                          mol_type = other RNA
                          organism = synthetic construct
SEQUENCE: 155
ccgctgccca atgccatcct ggagttcctg                                          30

SEQ ID NO: 156            moltype = RNA  length = 30
FEATURE                   Location/Qualifiers
misc_feature              1..30
                          note = Nucleic acid
source                    1..30
                          mol_type = other RNA
                          organism = synthetic construct
SEQUENCE: 156
tgcccaatgc catcctggag ttcctgtaag                                          30

SEQ ID NO: 157            moltype = RNA  length = 28
FEATURE                   Location/Qualifiers
misc_feature              1..28
                          note = Nucleic acid
source                    1..28
                          mol_type = other RNA
                          organism = synthetic construct
SEQUENCE: 157
cccaatgcca tcctggagtt cctgtaag                                            28

SEQ ID NO: 158            moltype = RNA  length = 28
FEATURE                   Location/Qualifiers
misc_feature              1..28
                          note = Nucleic acid
source                    1..28
                          mol_type = other RNA
                          organism = synthetic construct
SEQUENCE: 158
tgcccaatgc catcctggag ttcctgta                                            28

SEQ ID NO: 159            moltype = RNA  length = 22
FEATURE                   Location/Qualifiers
misc_feature              1..22
                          note = Nucleic acid
source                    1..22
                          mol_type = other RNA
                          organism = synthetic construct
SEQUENCE: 159
caatgccatc ctggagttcc tg                                                  22

SEQ ID NO: 160            moltype = RNA  length = 29
FEATURE                   Location/Qualifiers
misc_feature              1..29
                          note = Nucleic acid
source                    1..29
                          mol_type = other RNA
                          organism = synthetic construct
SEQUENCE: 160
agcctctcgc tcactcaccc tgcaaagga                                           29

SEQ ID NO: 161            moltype = RNA  length = 29
FEATURE                   Location/Qualifiers
misc_feature              1..29
                          note = Nucleic acid
source                    1..29
                          mol_type = other RNA
                          organism = synthetic construct
SEQUENCE: 161
ccactcagag ctcagatctt ctaacttcc                                           29

SEQ ID NO: 162            moltype = RNA  length = 27
FEATURE                   Location/Qualifiers
misc_feature              1..27
                          note = Nucleic acid
source                    1..27
                          mol_type = other RNA
                          organism = synthetic construct
SEQUENCE: 162
cttccactca gagctcagat cttctaa                                             27

SEQ ID NO: 163            moltype = RNA  length = 25
```

```
FEATURE                 Location/Qualifiers
misc_feature            1..25
                        note = Nucleic acid
source                  1..25
                        mol_type = other RNA
                        organism = synthetic construct
SEQUENCE: 163
gggatccagt atacttacag gctcc                                             25

SEQ ID NO: 164          moltype = RNA  length = 17
FEATURE                 Location/Qualifiers
misc_feature            1..17
                        note = Nucleic acid
source                  1..17
                        mol_type = other RNA
                        organism = synthetic construct
SEQUENCE: 164
ctcagagctc agatctt                                                      17

SEQ ID NO: 165          moltype = RNA  length = 15
FEATURE                 Location/Qualifiers
misc_feature            1..15
                        note = Nucleic acid
source                  1..15
                        mol_type = other RNA
                        organism = synthetic construct
SEQUENCE: 165
ggctgctttg ccctc                                                        15

SEQ ID NO: 166          moltype = RNA  length = 27
FEATURE                 Location/Qualifiers
misc_feature            1..27
                        note = Nucleic acid
source                  1..27
                        mol_type = other RNA
                        organism = synthetic construct
SEQUENCE: 166
ctcagatctt ctaacttcct ctttaac                                           27

SEQ ID NO: 167          moltype = RNA  length = 29
FEATURE                 Location/Qualifiers
misc_feature            1..29
                        note = Nucleic acid
source                  1..29
                        mol_type = other RNA
                        organism = synthetic construct
SEQUENCE: 167
ctcagagctc agatcttcta acttcctct                                         29

SEQ ID NO: 168          moltype = RNA  length = 27
FEATURE                 Location/Qualifiers
misc_feature            1..27
                        note = Nucleic acid
source                  1..27
                        mol_type = other RNA
                        organism = synthetic construct
SEQUENCE: 168
cgccttccac tcagagctca gatcttc                                           27

SEQ ID NO: 169          moltype = RNA  length = 27
FEATURE                 Location/Qualifiers
misc_feature            1..27
                        note = Nucleic acid
source                  1..27
                        mol_type = other RNA
                        organism = synthetic construct
SEQUENCE: 169
tcagctcttg aagtaaacgg tttaccg                                           27

SEQ ID NO: 170          moltype = RNA  length = 27
FEATURE                 Location/Qualifiers
misc_feature            1..27
                        note = Nucleic acid
source                  1..27
                        mol_type = other RNA
                        organism = synthetic construct
SEQUENCE: 170
tttgccctca gctcttgaag taaacgg                                           27
```

```
SEQ ID NO: 171         moltype = RNA   length = 27
FEATURE                Location/Qualifiers
misc_feature           1..27
                       note = Nucleic acid
source                 1..27
                       mol_type = other RNA
                       organism = synthetic construct
SEQUENCE: 171
ggctgctttg ccctcagctc ttgaagt                                         27

SEQ ID NO: 172         moltype = RNA   length = 26
FEATURE                Location/Qualifiers
misc_feature           1..26
                       note = Nucleic acid
source                 1..26
                       mol_type = other RNA
                       organism = synthetic construct
SEQUENCE: 172
caggagctag gtcaggctgc tttgcc                                          26

SEQ ID NO: 173         moltype = RNA   length = 25
FEATURE                Location/Qualifiers
misc_feature           1..25
                       note = Nucleic acid
source                 1..25
                       mol_type = other RNA
                       organism = synthetic construct
SEQUENCE: 173
tccaatagtg gtcagtccag gagct                                           25

SEQ ID NO: 174         moltype = RNA   length = 27
FEATURE                Location/Qualifiers
misc_feature           1..27
                       note = Nucleic acid
source                 1..27
                       mol_type = other RNA
                       organism = synthetic construct
SEQUENCE: 174
aaagagaatg ggatccagta tacttac                                         27

SEQ ID NO: 175         moltype = RNA   length = 27
FEATURE                Location/Qualifiers
misc_feature           1..27
                       note = Nucleic acid
source                 1..27
                       mol_type = other RNA
                       organism = synthetic construct
SEQUENCE: 175
aaatagctag agccaaagag aatggga                                         27

SEQ ID NO: 176         moltype = RNA   length = 33
FEATURE                Location/Qualifiers
misc_feature           1..33
                       note = Nucleic acid
source                 1..33
                       mol_type = other RNA
                       organism = synthetic construct
SEQUENCE: 176
ggctgctttg ccctcagctc ttgaagtaaa cgg                                  33

SEQ ID NO: 177         moltype = RNA   length = 30
FEATURE                Location/Qualifiers
misc_feature           1..30
                       note = Nucleic acid
source                 1..30
                       mol_type = other RNA
                       organism = synthetic construct
SEQUENCE: 177
aggctgcttt gccctcagct cttgaagtaa                                      30

SEQ ID NO: 178         moltype = RNA   length = 30
FEATURE                Location/Qualifiers
misc_feature           1..30
                       note = Nucleic acid
source                 1..30
                       mol_type = other RNA
                       organism = synthetic construct
SEQUENCE: 178
gtcaggctgc tttgccctca gctcttgaag                                      30
```

```
SEQ ID NO: 179          moltype = RNA  length = 30
FEATURE                 Location/Qualifiers
misc_feature            1..30
                        note = Nucleic acid
source                  1..30
                        mol_type = other RNA
                        organism = synthetic construct
SEQUENCE: 179
aggtcaggct gctttgccct cagctcttga                                         30

SEQ ID NO: 180          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 180
cagagctcag atcttctaac ttcct                                              25

SEQ ID NO: 181          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 181
cttacaggct ccaatagtgg tcagt                                              25

SEQ ID NO: 182          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 182
atgggatcca gtatacttac aggct                                              25

SEQ ID NO: 183          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 183
agagaatggg atccagtata cttac                                              25

SEQ ID NO: 184          moltype = RNA  length = 27
FEATURE                 Location/Qualifiers
misc_feature            1..27
                        note = Nucleic acid
source                  1..27
                        mol_type = other RNA
                        organism = synthetic construct
SEQUENCE: 184
aacttcctct ttaacagaaa agcatac                                            27

SEQ ID NO: 185          moltype = RNA  length = 23
FEATURE                 Location/Qualifiers
misc_feature            1..23
                        note = Nucleic acid
source                  1..23
                        mol_type = other RNA
                        organism = synthetic construct
SEQUENCE: 185
ctcatacctt ctgcttgatg atc                                                23

SEQ ID NO: 186          moltype = RNA  length = 20
FEATURE                 Location/Qualifiers
misc_feature            1..20
                        note = Nucleic acid
source                  1..20
                        mol_type = other RNA
                        organism = synthetic construct
SEQUENCE: 186
```

```
tcaaggaaga tggcatttct                                                   20

SEQ ID NO: 187          moltype = RNA   length = 20
FEATURE                 Location/Qualifiers
misc_feature            1..20
                        note = Nucleic acid
source                  1..20
                        mol_type = other RNA
                        organism = synthetic construct
SEQUENCE: 187
gaaagccagt cggtaagttc                                                   20

SEQ ID NO: 188          moltype = RNA   length = 15
FEATURE                 Location/Qualifiers
misc_feature            1..15
                        note = Nucleic acid
source                  1..15
                        mol_type = other RNA
                        organism = synthetic construct
SEQUENCE: 188
cacccaccat caccc                                                        15

SEQ ID NO: 189          moltype = RNA   length = 23
FEATURE                 Location/Qualifiers
misc_feature            1..23
                        note = Nucleic acid
source                  1..23
                        mol_type = other RNA
                        organism = synthetic construct
SEQUENCE: 189
cctctgtgat tttataactt gat                                               23

SEQ ID NO: 190          moltype = RNA   length = 20
FEATURE                 Location/Qualifiers
misc_feature            1..20
                        note = Nucleic acid
source                  1..20
                        mol_type = other RNA
                        organism = synthetic construct
SEQUENCE: 190
tgatatcctc aaggtcaccc                                                   20

SEQ ID NO: 191          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 191
ggtacctcca acatcaagga agatggcatt                                        30

SEQ ID NO: 192          moltype = RNA   length = 26
FEATURE                 Location/Qualifiers
misc_feature            1..26
                        note = Nucleic acid
source                  1..26
                        mol_type = other RNA
                        organism = synthetic construct
SEQUENCE: 192
atttctagtt tggagatggc agtttc                                            26

SEQ ID NO: 193          moltype = RNA   length = 26
FEATURE                 Location/Qualifiers
misc_feature            1..26
                        note = Nucleic acid
source                  1..26
                        mol_type = other RNA
                        organism = synthetic construct
SEQUENCE: 193
catcaaggaa gatggcattt ctagtt                                            26

SEQ ID NO: 194          moltype = RNA   length = 26
FEATURE                 Location/Qualifiers
misc_feature            1..26
                        note = Nucleic acid
source                  1..26
                        mol_type = other RNA
                        organism = synthetic construct
```

```
SEQUENCE: 194
gagcaggtac ctccaacatc aaggaa                                      26

SEQ ID NO: 195          moltype = RNA  length = 30
FEATURE                 Location/Qualifiers
misc_feature            1..30
                        note = Nucleic acid
source                  1..30
                        mol_type = other RNA
                        organism = synthetic construct
SEQUENCE: 195
ctccaacatc aaggaagatg gcatttctag                                  30

SEQ ID NO: 196          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 196
accagagtaa cagtctgagt aggag                                       25

SEQ ID NO: 197          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 197
caccagagta acagtctgag tagga                                       25

SEQ ID NO: 198          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 198
tcaccagagt aacagtctga gtagg                                       25

SEQ ID NO: 199          moltype = RNA  length = 25
FEATURE                 Location/Qualifiers
misc_feature            1..25
                        note = Nucleic acid
source                  1..25
                        mol_type = other RNA
                        organism = synthetic construct
SEQUENCE: 199
gtcaccagag taacagtctg agtag                                       25

SEQ ID NO: 200          moltype = RNA  length = 26
FEATURE                 Location/Qualifiers
misc_feature            1..26
                        note = Nucleic acid
source                  1..26
                        mol_type = other RNA
                        organism = synthetic construct
SEQUENCE: 200
accagagtaa cagtctgagt aggagc                                      26

SEQ ID NO: 201          moltype = RNA  length = 24
FEATURE                 Location/Qualifiers
misc_feature            1..24
                        note = Nucleic acid
source                  1..24
                        mol_type = other RNA
                        organism = synthetic construct
SEQUENCE: 201
ttctgtccaa gcccggttga aatc                                        24

SEQ ID NO: 202          moltype = RNA  length = 30
FEATURE                 Location/Qualifiers
misc_feature            1..30
                        note = Nucleic acid
source                  1..30
                        mol_type = other RNA
```

```
                        organism = synthetic construct
SEQUENCE: 202
acatcaagga agatggcatt tctagtttgg                                          30

SEQ ID NO: 203          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 203
acatcaagga agatggcatt tctag                                               25

SEQ ID NO: 204          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 204
atcattttt ctcataccttt ctgct                                               25

SEQ ID NO: 205          moltype = RNA   length = 21
FEATURE                 Location/Qualifiers
misc_feature            1..21
                        note = Nucleic acid
source                  1..21
                        mol_type = other RNA
                        organism = synthetic construct
SEQUENCE: 205
cacccaccat caccctctgt g                                                   21

SEQ ID NO: 206          moltype = RNA   length = 22
FEATURE                 Location/Qualifiers
misc_feature            1..22
                        note = Nucleic acid
source                  1..22
                        mol_type = other RNA
                        organism = synthetic construct
SEQUENCE: 206
atcatctcgt tgatatcctc aa                                                  22

SEQ ID NO: 207          moltype = RNA   length = 28
FEATURE                 Location/Qualifiers
misc_feature            1..28
                        note = Nucleic acid
source                  1..28
                        mol_type = other RNA
                        organism = synthetic construct
SEQUENCE: 207
ctccaacatc aaggaagatg gcatttct                                            28

SEQ ID NO: 208          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 208
catcaaggaa gatggcattt ctagt                                               25

SEQ ID NO: 209          moltype = RNA   length = 18
FEATURE                 Location/Qualifiers
misc_feature            1..18
                        note = Nucleic acid
source                  1..18
                        mol_type = other RNA
                        organism = synthetic construct
SEQUENCE: 209
ttgctggtct tgttttttc                                                      18

SEQ ID NO: 210          moltype = RNA   length = 16
FEATURE                 Location/Qualifiers
misc_feature            1..16
                        note = Nucleic acid
source                  1..16
```

```
                            mol_type = other RNA
                            organism = synthetic construct
SEQUENCE: 210
ccgtaatgat tgttct                                                       16

SEQ ID NO: 211              moltype = RNA   length = 18
FEATURE                     Location/Qualifiers
misc_feature                1..18
                            note = Nucleic acid
source                      1..18
                            mol_type = other RNA
                            organism = synthetic construct
SEQUENCE: 211
gctggtcttg tttttcaa                                                     18

SEQ ID NO: 212              moltype = RNA   length = 20
FEATURE                     Location/Qualifiers
misc_feature                1..20
                            note = Nucleic acid
source                      1..20
                            mol_type = other RNA
                            organism = synthetic construct
SEQUENCE: 212
tggtcttgtt tttcaaattt                                                   20

SEQ ID NO: 213              moltype = RNA   length = 20
FEATURE                     Location/Qualifiers
misc_feature                1..20
                            note = Nucleic acid
source                      1..20
                            mol_type = other RNA
                            organism = synthetic construct
SEQUENCE: 213
gtcttgtttt tcaaattttg                                                   20

SEQ ID NO: 214              moltype = RNA   length = 20
FEATURE                     Location/Qualifiers
misc_feature                1..20
                            note = Nucleic acid
source                      1..20
                            mol_type = other RNA
                            organism = synthetic construct
SEQUENCE: 214
cttgttttc aaattttggg                                                    20

SEQ ID NO: 215              moltype = RNA   length = 19
FEATURE                     Location/Qualifiers
misc_feature                1..19
                            note = Nucleic acid
source                      1..19
                            mol_type = other RNA
                            organism = synthetic construct
SEQUENCE: 215
tgtttttcaa attttgggc                                                    19

SEQ ID NO: 216              moltype = RNA   length = 33
FEATURE                     Location/Qualifiers
misc_feature                1..33
                            note = Nucleic acid
source                      1..33
                            mol_type = other RNA
                            organism = synthetic construct
SEQUENCE: 216
tccaactggg gacgcctctg ttccaaatcc tgc                                    33

SEQ ID NO: 217              moltype = RNA   length = 21
FEATURE                     Location/Qualifiers
misc_feature                1..21
                            note = Nucleic acid
source                      1..21
                            mol_type = other RNA
                            organism = synthetic construct
SEQUENCE: 217
tcctgcattg ttgcctgtaa g                                                 21

SEQ ID NO: 218              moltype = RNA   length = 30
FEATURE                     Location/Qualifiers
misc_feature                1..30
                            note = Nucleic acid
```

| | | |
|---|---|---|
| source | 1..30<br>mol_type = other RNA<br>organism = synthetic construct | |
| SEQUENCE: 218 | | |
| tccaactggg gacgcctctg ttccaaatcc | | 30 |
| | | |
| SEQ ID NO: 219<br>FEATURE<br>misc_feature | moltype = RNA   length = 21<br>Location/Qualifiers<br>1..21<br>note = Nucleic acid | |
| source | 1..21<br>mol_type = other RNA<br>organism = synthetic construct | |
| SEQUENCE: 219 | | |
| actggggacg cctctgttcc a | | 21 |
| | | |
| SEQ ID NO: 220<br>FEATURE<br>misc_feature | moltype = RNA   length = 20<br>Location/Qualifiers<br>1..20<br>note = Nucleic acid | |
| source | 1..20<br>mol_type = other RNA<br>organism = synthetic construct | |
| SEQUENCE: 220 | | |
| ccgtaatgat tgttctagcc | | 20 |
| | | |
| SEQ ID NO: 221<br>FEATURE<br>misc_feature | moltype = RNA   length = 20<br>Location/Qualifiers<br>1..20<br>note = Nucleic acid | |
| source | 1..20<br>mol_type = other RNA<br>organism = synthetic construct | |
| SEQUENCE: 221 | | |
| tgttaaaaaa cttacttcga | | 20 |
| | | |
| SEQ ID NO: 222<br>FEATURE<br>misc_feature | moltype = RNA   length = 18<br>Location/Qualifiers<br>1..18<br>note = Nucleic acid | |
| source | 1..18<br>mol_type = other RNA<br>organism = synthetic construct | |
| SEQUENCE: 222 | | |
| ctgttgcctc cggttctg | | 18 |
| | | |
| SEQ ID NO: 223<br>FEATURE<br>misc_feature | moltype = RNA   length = 18<br>Location/Qualifiers<br>1..18<br>note = Nucleic acid | |
| source | 1..18<br>mol_type = other RNA<br>organism = synthetic construct | |
| SEQUENCE: 223 | | |
| ttggctctgg cctgtcct | | 18 |
| | | |
| SEQ ID NO: 224<br>FEATURE<br>misc_feature | moltype = RNA   length = 33<br>Location/Qualifiers<br>1..33<br>note = Nucleic acid | |
| source | 1..33<br>mol_type = other RNA<br>organism = synthetic construct | |
| SEQUENCE: 224 | | |
| ttcaactgtt gcctccggtt ctgaaggtgt tct | | 33 |
| | | |
| SEQ ID NO: 225<br>FEATURE<br>misc_feature | moltype = RNA   length = 25<br>Location/Qualifiers<br>1..25<br>note = Nucleic acid | |
| source | 1..25<br>mol_type = other RNA<br>organism = synthetic construct | |
| SEQUENCE: 225 | | |
| tacttcatcc cactgattct gaatt | | 25 |
| | | |
| SEQ ID NO: 226<br>FEATURE<br>misc_feature | moltype = RNA   length = 25<br>Location/Qualifiers<br>1..25 | |

```
                        note = Nucleic acid
source                  1..25
                        mol_type = other RNA
                        organism = synthetic construct
SEQUENCE: 226
ctgaaggtgt tcttgtactt catcc                                               25

SEQ ID NO: 227          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 227
ctgttgcctc cggttctgaa ggtgt                                               25

SEQ ID NO: 228          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 228
ctgttgcctc cggttctgaa ggtgttcttg                                          30

SEQ ID NO: 229          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 229
caactgttgc ctccggttct gaaggtgttc                                          30

SEQ ID NO: 230          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 230
ttgcctccgg ttctgaaggt gttcttgtac                                          30

SEQ ID NO: 231          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 231
gttgcctccg gttctgaagg tgttc                                               25

SEQ ID NO: 232          moltype = RNA   length = 23
FEATURE                 Location/Qualifiers
misc_feature            1..23
                        note = Nucleic acid
source                  1..23
                        mol_type = other RNA
                        organism = synthetic construct
SEQUENCE: 232
ctccggttct gaaggtgttc ttg                                                 23

SEQ ID NO: 233          moltype = RNA   length = 22
FEATURE                 Location/Qualifiers
misc_feature            1..22
                        note = Nucleic acid
source                  1..22
                        mol_type = other RNA
                        organism = synthetic construct
SEQUENCE: 233
ctccggttct gaaggtgttc tt                                                  22

SEQ ID NO: 234          moltype = RNA   length = 21
FEATURE                 Location/Qualifiers
```

```
misc_feature           1..21
                       note = Nucleic acid
source                 1..21
                       mol_type = other RNA
                       organism = synthetic construct
SEQUENCE: 234
ctccggttct gaaggtgttc t                                            21

SEQ ID NO: 235         moltype = RNA  length = 20
FEATURE                Location/Qualifiers
misc_feature           1..20
                       note = Nucleic acid
source                 1..20
                       mol_type = other RNA
                       organism = synthetic construct
SEQUENCE: 235
ctccggttct gaaggtgttc                                              20

SEQ ID NO: 236         moltype = RNA  length = 19
FEATURE                Location/Qualifiers
misc_feature           1..19
                       note = Nucleic acid
source                 1..19
                       mol_type = other RNA
                       organism = synthetic construct
SEQUENCE: 236
ctccggttct gaaggtgtt                                               19

SEQ ID NO: 237         moltype = RNA  length = 25
FEATURE                Location/Qualifiers
misc_feature           1..25
                       note = Nucleic acid
source                 1..25
                       mol_type = other RNA
                       organism = synthetic construct
SEQUENCE: 237
cattcaactg ttgcctccgg ttctg                                        25

SEQ ID NO: 238         moltype = RNA  length = 24
FEATURE                Location/Qualifiers
misc_feature           1..24
                       note = Nucleic acid
source                 1..24
                       mol_type = other RNA
                       organism = synthetic construct
SEQUENCE: 238
ctgttgcctc cggttctgaa ggtg                                         24

SEQ ID NO: 239         moltype = RNA  length = 31
FEATURE                Location/Qualifiers
misc_feature           1..31
                       note = Nucleic acid
source                 1..31
                       mol_type = other RNA
                       organism = synthetic construct
SEQUENCE: 239
cattcaactg ttgcctccgg ttctgaaggt g                                 31

SEQ ID NO: 240         moltype = RNA  length = 21
FEATURE                Location/Qualifiers
misc_feature           1..21
                       note = Nucleic acid
source                 1..21
                       mol_type = other RNA
                       organism = synthetic construct
SEQUENCE: 240
tactaacctt ggtttctgtg a                                            21

SEQ ID NO: 241         moltype = RNA  length = 27
FEATURE                Location/Qualifiers
misc_feature           1..27
                       note = Nucleic acid
source                 1..27
                       mol_type = other RNA
                       organism = synthetic construct
SEQUENCE: 241
tgtataggga ccctccttcc atgactc                                      27

SEQ ID NO: 242         moltype = RNA  length = 25
```

```
FEATURE               Location/Qualifiers
misc_feature          1..25
                      note = Nucleic acid
source                1..25
                      mol_type = other RNA
                      organism = synthetic construct
SEQUENCE: 242
ctaaccttgg tttctgtgat tttct                                          25

SEQ ID NO: 243        moltype = RNA  length = 27
FEATURE               Location/Qualifiers
misc_feature          1..27
                      note = Nucleic acid
source                1..27
                      mol_type = other RNA
                      organism = synthetic construct
SEQUENCE: 243
ggtatctttg atactaacct tggtttc                                        27

SEQ ID NO: 244        moltype = RNA  length = 22
FEATURE               Location/Qualifiers
misc_feature          1..22
                      note = Nucleic acid
source                1..22
                      mol_type = other RNA
                      organism = synthetic construct
SEQUENCE: 244
attctttcaa ctagaataaa ag                                             22

SEQ ID NO: 245        moltype = RNA  length = 25
FEATURE               Location/Qualifiers
misc_feature          1..25
                      note = Nucleic acid
source                1..25
                      mol_type = other RNA
                      organism = synthetic construct
SEQUENCE: 245
gattctgaat tctttcaact agaat                                          25

SEQ ID NO: 246        moltype = RNA  length = 20
FEATURE               Location/Qualifiers
misc_feature          1..20
                      note = Nucleic acid
source                1..20
                      mol_type = other RNA
                      organism = synthetic construct
SEQUENCE: 246
atcccactga ttctgaattc                                                20

SEQ ID NO: 247        moltype = RNA  length = 22
FEATURE               Location/Qualifiers
misc_feature          1..22
                      note = Nucleic acid
source                1..22
                      mol_type = other RNA
                      organism = synthetic construct
SEQUENCE: 247
aaccgagacc ggacaggatt ct                                             22

SEQ ID NO: 248        moltype = RNA  length = 20
FEATURE               Location/Qualifiers
misc_feature          1..20
                      note = Nucleic acid
source                1..20
                      mol_type = other RNA
                      organism = synthetic construct
SEQUENCE: 248
ctgttgcagt aatctatgag                                                20

SEQ ID NO: 249        moltype = RNA  length = 23
FEATURE               Location/Qualifiers
misc_feature          1..23
                      note = Nucleic acid
source                1..23
                      mol_type = other RNA
                      organism = synthetic construct
SEQUENCE: 249
tgccattgtt tcatcagctc ttt                                            23
```

```
SEQ ID NO: 250         moltype = RNA   length = 20
FEATURE                Location/Qualifiers
misc_feature           1..20
                       note = Nucleic acid
source                 1..20
                       mol_type = other RNA
                       organism = synthetic construct
SEQUENCE: 250
tgcagtaatc tatgagtttc                                              20

SEQ ID NO: 251         moltype = RNA   length = 20
FEATURE                Location/Qualifiers
misc_feature           1..20
                       note = Nucleic acid
source                 1..20
                       mol_type = other RNA
                       organism = synthetic construct
SEQUENCE: 251
tcctgtagga cattggcagt                                              20

SEQ ID NO: 252         moltype = RNA   length = 18
FEATURE                Location/Qualifiers
misc_feature           1..18
                       note = Nucleic acid
source                 1..18
                       mol_type = other RNA
                       organism = synthetic construct
SEQUENCE: 252
gagtcttcta ggagcctt                                                18

SEQ ID NO: 253         moltype = RNA   length = 25
FEATURE                Location/Qualifiers
misc_feature           1..25
                       note = Nucleic acid
source                 1..25
                       mol_type = other RNA
                       organism = synthetic construct
SEQUENCE: 253
ggccaaacct cggcttacct gaaat                                        25

SEQ ID NO: 254         moltype = RNA   length = 20
FEATURE                Location/Qualifiers
misc_feature           1..20
                       note = Nucleic acid
source                 1..20
                       mol_type = other RNA
                       organism = synthetic construct
SEQUENCE: 254
ggccaaacct cggcttacct                                              20

SEQ ID NO: 255         moltype = RNA   length = 29
FEATURE                Location/Qualifiers
misc_feature           1..29
                       note = Nucleic acid
source                 1..29
                       mol_type = other RNA
                       organism = synthetic construct
SEQUENCE: 255
aatcagctgg gagagagctt cctgtagct                                    29

SEQ ID NO: 256         moltype = RNA   length = 26
FEATURE                Location/Qualifiers
misc_feature           1..26
                       note = Nucleic acid
source                 1..26
                       mol_type = other RNA
                       organism = synthetic construct
SEQUENCE: 256
tcgttcttct gtcgtcgtaa cgtttc                                       26

SEQ ID NO: 257         moltype = RNA   length = 16
FEATURE                Location/Qualifiers
misc_feature           1..16
                       note = Nucleic acid
source                 1..16
                       mol_type = other RNA
                       organism = synthetic construct
SEQUENCE: 257
caccgattgt cttcga                                                  16
```

SEQ ID NO: 258          moltype = RNA   length = 17
FEATURE                 Location/Qualifiers
misc_feature            1..17
                        note = Nucleic acid
source                  1..17
                        mol_type = other RNA
                        organism = synthetic construct
SEQUENCE: 258
cccttgtacg atttatg                                                  17

SEQ ID NO: 259          moltype = RNA   length = 18
FEATURE                 Location/Qualifiers
misc_feature            1..18
                        note = Nucleic acid
source                  1..18
                        mol_type = other RNA
                        organism = synthetic construct
SEQUENCE: 259
tctgtgttta aggactct                                                 18

SEQ ID NO: 260          moltype = RNA   length = 31
FEATURE                 Location/Qualifiers
misc_feature            1..31
                        note = Nucleic acid
source                  1..31
                        mol_type = other RNA
                        organism = synthetic construct
SEQUENCE: 260
gccgctgccc aatgccatcc tggagttcct g                                  31

SEQ ID NO: 261          moltype = RNA   length = 29
FEATURE                 Location/Qualifiers
misc_feature            1..29
                        note = Nucleic acid
source                  1..29
                        mol_type = other RNA
                        organism = synthetic construct
SEQUENCE: 261
attagatctg tcgccctacc tcttttttc                                     29

SEQ ID NO: 262          moltype = RNA   length = 27
FEATURE                 Location/Qualifiers
misc_feature            1..27
                        note = Nucleic acid
source                  1..27
                        mol_type = other RNA
                        organism = synthetic construct
SEQUENCE: 262
tgtcgcccta cctcttttt ctgtctg                                        27

SEQ ID NO: 263          moltype = RNA   length = 25
FEATURE                 Location/Qualifiers
misc_feature            1..25
                        note = Nucleic acid
source                  1..25
                        mol_type = other RNA
                        organism = synthetic construct
SEQUENCE: 263
gcccaatgcc atcctggagt tcctg                                         25

SEQ ID NO: 264          moltype = RNA   length = 30
FEATURE                 Location/Qualifiers
misc_feature            1..30
                        note = Nucleic acid
source                  1..30
                        mol_type = other RNA
                        organism = synthetic construct
SEQUENCE: 264
gagcctctcg ctcactcacc ctgcaaagga                                    30

SEQ ID NO: 265          moltype = RNA   length = 36
FEATURE                 Location/Qualifiers
misc_feature            1..36
                        note = Nucleic acid
source                  1..36
                        mol_type = other RNA
                        organism = synthetic construct
SEQUENCE: 265

```
atcattttt ctcatacctt ctgctaggag ctaaaa                                          36

SEQ ID NO: 266              moltype = RNA   length = 26
FEATURE                     Location/Qualifiers
misc_feature                1..26
                            note = Nucleic acid
source                      1..26
                            mol_type = other RNA
                            organism = synthetic construct
SEQUENCE: 266
ggaagctaag gaagaagctg agcagg                                                    26

SEQ ID NO: 267              moltype = AA   length = 5
FEATURE                     Location/Qualifiers
REGION                      1..5
                            note = Synthetic polypeptide
source                      1..5
                            mol_type = protein
                            organism = synthetic construct
SEQUENCE: 267
SYWMH                                                                            5

SEQ ID NO: 268              moltype = AA   length = 17
FEATURE                     Location/Qualifiers
REGION                      1..17
                            note = Synthetic polypeptide
source                      1..17
                            mol_type = protein
                            organism = synthetic construct
SEQUENCE: 268
EINPTNGRTN YIEKFKS                                                              17

SEQ ID NO: 269              moltype = AA   length = 7
FEATURE                     Location/Qualifiers
REGION                      1..7
                            note = Synthetic polypeptide
source                      1..7
                            mol_type = protein
                            organism = synthetic construct
SEQUENCE: 269
GTRAYHY                                                                          7

SEQ ID NO: 270              moltype = AA   length = 11
FEATURE                     Location/Qualifiers
REGION                      1..11
                            note = Synthetic polypeptide
source                      1..11
                            mol_type = protein
                            organism = synthetic construct
SEQUENCE: 270
RASDNLYSNL A                                                                    11

SEQ ID NO: 271              moltype = AA   length = 7
FEATURE                     Location/Qualifiers
REGION                      1..7
                            note = Synthetic polypeptide
source                      1..7
                            mol_type = protein
                            organism = synthetic construct
SEQUENCE: 271
DATNLAD                                                                          7

SEQ ID NO: 272              moltype = AA   length = 9
FEATURE                     Location/Qualifiers
REGION                      1..9
                            note = Synthetic polypeptide
source                      1..9
                            mol_type = protein
                            organism = synthetic construct
SEQUENCE: 272
QHFWGTPLT                                                                        9

SEQ ID NO: 273              moltype = AA   length = 7
FEATURE                     Location/Qualifiers
REGION                      1..7
                            note = Synthetic polypeptide
source                      1..7
                            mol_type = protein
                            organism = synthetic construct
```

```
SEQUENCE: 273
GYTFTSY                                                                      7

SEQ ID NO: 274         moltype = AA  length = 6
FEATURE                Location/Qualifiers
REGION                 1..6
                       note = Synthetic polypeptide
source                 1..6
                       mol_type = protein
                       organism = synthetic construct
SEQUENCE: 274
NPTNGR                                                                       6

SEQ ID NO: 275         moltype = AA  length = 6
FEATURE                Location/Qualifiers
REGION                 1..6
                       note = Synthetic polypeptide
source                 1..6
                       mol_type = protein
                       organism = synthetic construct
SEQUENCE: 275
TSYWMH                                                                       6

SEQ ID NO: 276         moltype = AA  length = 13
FEATURE                Location/Qualifiers
REGION                 1..13
                       note = Synthetic polypeptide
source                 1..13
                       mol_type = protein
                       organism = synthetic construct
SEQUENCE: 276
WIGEINPTNG RTN                                                              13

SEQ ID NO: 277         moltype = AA  length = 6
FEATURE                Location/Qualifiers
REGION                 1..6
                       note = Synthetic polypeptide
source                 1..6
                       mol_type = protein
                       organism = synthetic construct
SEQUENCE: 277
ARGTRA                                                                       6

SEQ ID NO: 278         moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 278
YSNLAWY                                                                      7

SEQ ID NO: 279         moltype = AA  length = 10
FEATURE                Location/Qualifiers
REGION                 1..10
                       note = Synthetic polypeptide
source                 1..10
                       mol_type = protein
                       organism = synthetic construct
SEQUENCE: 279
LLVYDATNLA                                                                  10

SEQ ID NO: 280         moltype = AA  length = 8
FEATURE                Location/Qualifiers
REGION                 1..8
                       note = Synthetic polypeptide
source                 1..8
                       mol_type = protein
                       organism = synthetic construct
SEQUENCE: 280
QHFWGTPL                                                                     8

SEQ ID NO: 281         moltype = AA  length = 9
FEATURE                Location/Qualifiers
REGION                 1..9
                       note = Synthetic polypeptide
source                 1..9
                       mol_type = protein
```

```
                         organism = synthetic construct
SEQUENCE: 281
QHFAGTPLT                                                            9

SEQ ID NO: 282           moltype = AA   length = 8
FEATURE                  Location/Qualifiers
REGION                   1..8
                         note = Synthetic polypeptide
source                   1..8
                         mol_type = protein
                         organism = synthetic construct
SEQUENCE: 282
QHFAGTPL                                                             8

SEQ ID NO: 283           moltype = AA   length = 116
FEATURE                  Location/Qualifiers
REGION                   1..116
                         note = Synthetic polypeptide
source                   1..116
                         mol_type = protein
                         organism = synthetic construct
SEQUENCE: 283
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSS       116

SEQ ID NO: 284           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 284
DIQMTQSPAS LSVSVGETVT ITCRASDNLY SNLAWYQQKQ GKSPQLLVYD ATNLADGVPS    60
RFSGSGSGTQ YSLKINSLQS EDFGTYYCQH FWGTPLTFGA GTKLELK                 107

SEQ ID NO: 285           moltype = AA   length = 116
FEATURE                  Location/Qualifiers
REGION                   1..116
                         note = Synthetic polypeptide
source                   1..116
                         mol_type = protein
                         organism = synthetic construct
SEQUENCE: 285
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSS       116

SEQ ID NO: 286           moltype = AA   length = 107
FEATURE                  Location/Qualifiers
REGION                   1..107
                         note = Synthetic polypeptide
source                   1..107
                         mol_type = protein
                         organism = synthetic construct
SEQUENCE: 286
DIQMTQSPSS LSASVGDRVT ITCRASDNLY SNLAWYQQKP GKSPKLLVYD ATNLADGVPS    60
RFSGSGSGTD YSLKINSLQS EDFGTYYCQH FWGTPLTFGA GTKLELK                 107

SEQ ID NO: 287           moltype = AA   length = 330
FEATURE                  Location/Qualifiers
REGION                   1..330
                         note = Synthetic polypeptide
source                   1..330
                         mol_type = protein
                         organism = synthetic construct
SEQUENCE: 287
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 288           moltype = AA   length = 110
FEATURE                  Location/Qualifiers
REGION                   1..110
                         note = Synthetic polypeptide
source                   1..110
                         mol_type = protein
```

```
                                organism = synthetic construct
SEQUENCE: 288
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP             110

SEQ ID NO: 289          moltype = AA  length = 446
FEATURE                 Location/Qualifiers
REGION                  1..446
                        note = Synthetic polypeptide
source                  1..446
                        mol_type = protein
                        organism = synthetic construct
SEQUENCE: 289
QVQLQQPGAE LVKPGASVKL SCKASGYTFT SYWMHWVKQR PGQGLEWIGE INPTNGRTNY   60
IEKFKSKATL TVDKSSSTAY MQLSSLTSED SAVYYCARGT RAYHYWGQGT SVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 290          moltype = AA  length = 226
FEATURE                 Location/Qualifiers
REGION                  1..226
                        note = Synthetic polypeptide
source                  1..226
                        mol_type = protein
                        organism = synthetic construct
SEQUENCE: 290
QVQLQQPGAE LVKPGASVKL SCKASGYTFT SYWMHWVKQR PGQGLEWIGE INPTNGRTNY   60
IEKFKSKATL TVDKSSSTAY MQLSSLTSED SAVYYCARGT RAYHYWGQGT SVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCP                226

SEQ ID NO: 291          moltype = AA  length = 446
FEATURE                 Location/Qualifiers
REGION                  1..446
                        note = Synthetic polypeptide
source                  1..446
                        mol_type = protein
                        organism = synthetic construct
SEQUENCE: 291
EVQLVQSGAE VKKPGASVKV SCKASGYTFT SYWMHWVRQA PGQRLEWIGE INPTNGRTNY   60
IEKFKSRATL TVDKSASTAY MELSSLRSED TAVYYCARGT RAYHYWGQGT MVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 292          moltype = AA  length = 217
FEATURE                 Location/Qualifiers
REGION                  1..217
                        note = Synthetic polypeptide
source                  1..217
                        mol_type = protein
                        organism = synthetic construct
SEQUENCE: 292
DIQMTQSPSS LSASVGDRVT ITCRASDNLY SNLAWYQQKP GKSPKLLVYD ATNLADGVPS   60
RFSGSGSGTD YSLKINSLQS EDFGTYYCQH FWGTPLTFGA GTKLELKAST KGPSVFPLAP  120
SSKSTSGGTA ALGCLVKDYF PEPVTVSWNS GALTSGVHTF PAVLQSSGLY SLSSVVTVPS  180
SSLGTQTYIC NVNHKPSNTK VDKKVEPKSC DKTHTCP                          217

SEQ ID NO: 293          moltype = AA  length = 226
FEATURE                 Location/Qualifiers
REGION                  1..226
                        note = Synthetic polypeptide
source                  1..226
                        mol_type = protein
                        organism = synthetic construct
SEQUENCE: 293
QVQLQQPGAE LVKPGASVKL SCKASGYTFT SYWMHWVKQR PGQGLEWIGE INPTNGRTNY   60
IEKFKSKATL TVDKSSSTAY MQLSSLTSED SAVYYCARGT RAYHYWGQGT SVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCP                226

SEQ ID NO: 294          moltype = AA  length = 226
```

```
FEATURE              Location/Qualifiers
REGION               1..226
                     note = Synthetic polypeptide
source               1..226
                     mol_type = protein
                     organism = synthetic construct
SEQUENCE: 294
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                  226

SEQ ID NO: 295       moltype = DNA  length = 13993
FEATURE              Location/Qualifiers
source               1..13993
                     mol_type = genomic DNA
                     organism = Homo sapiens
SEQUENCE: 295
tcctggcatc agttactgtg ttgactcact cagtgttggg atcactcact ttccccctac    60
aggactcaga tctgggaggc aattccttc ggagaaaaac gaataggaaa aactgaagtg   120
ttactttttt taaagctgct gaagtttgtt ggtttctcat tgttttaag cctactggag   180
caataaagtt tgaagaactt ttaccaggtt ttttttatcg ctgccttgat atacacttt   240
caaaatgctt tggtgggaag aagtagagga ctgttatgaa agagaagatg ttcaaaagaa   300
aacattcaca aatgggtaa atgcacaatt ttctaagttt gggaagcagc atattgagaa   360
cctcttcagt gacctacagg atgggaggcg cctcctagac ctcctcgaag gcctgacagg   420
gcaaaaactg ccaaaagaaa aaggatccac aagagttcat gccctgaaca atgtcaacaa   480
ggcactgcgg gttttgcaga acaataatgt tgatttagtg aatattggaa gtactgacat   540
cgtagatgga aatcataaac tgactcttgg tttgatttgg aatataatcc tccactggca   600
ggtcaaaaat gtaatgaaaa atatcatggc tggattgcaa caaaccaaca gtgaaaagat   660
tctcctgagc tgggtccgac aatcaactcg taattatcca caggttaatg taatcaactt   720
caccaccagc tggtctgatg gcctggcttt gaatgctctc atccatagtc ataggccaga   780
cctatttgac tggaatagtg tggtttgcca gcagtcagcc acacaacgac tggaacatgc   840
attcaacatc gccagatatc aattaggcat agagaaacta ctcgatcctg aagatgttga   900
taccacctat ccagataaga agtccatctt aatgtacatc aatcactct tccaagtttt   960
gcctcaacaa gtgagcattg aagccatcca ggaagtggaa atgttgccaa ggccacctaa  1020
agtgactaaa gaagaacatt ttcagttaca tcatcaaatg cactattctc aacagatcac  1080
ggtcagtcta gcacagggat atgagagaac ttcttcccct aagcctcgat tcaagagcta  1140
tgcctacaca caggctgctt atgtcaccac ctctgaccct cacaggagcc catttccttc  1200
acagcatttg gaagctcctg aagcaagtc atttggcagt tcattgatgg agagtgaagt  1260
aaacctggac cgttatcaaa cagctttaga agaagtatta tcgtggcttc tttctgctga  1320
ggacacattg caagcacaag gagagatttc taatgatgtg gaagtggtga agaccagtt  1380
tcatactcat gaggggtaca tgatggattt gacagcccat cagggccggg ttggtaatat  1440
tctacaattg ggaagtaagc tgattggaac aggaaaatta tcagaagatg aagaaactga  1500
agtacaagag cagatgaatc tcctaaattc aagatgggaa tgcctcaggg tagctagcat  1560
ggaaaaacaa agcaatttac atagagtttt aatggatctc cagaatcaga aactgaaaga  1620
gttgaatgac tggctaacaa aaacagaaga aagaacaagg aaaatggagg aagagcctct  1680
tggacctgat cttgaagacc taaaacgcca agtacaacaa cataaggtgc ttcaagaga  1740
tctagaacaa gaacaagtca gggtcaattc tctcactcac atggtggtgg tagttgatga  1800
atctagtgga gatcacgcaa ctgctgcttt ggaagaacaa cttaaggtat gggagatcg  1860
atgggcaaac atctgtagat ggacagaaga ccgctgggtt cttttacaag acatccttct  1920
caaatggcaa cgtcttactg aagaacagtg ccttttttagt gcatggcttt cagaaaaaga  1980
agatgcagtg aacaagattc acacaactgg ctttaaagat caaaatgaaa tgttatcaag  2040
tcttcaaaaa ctggccgttt taaagcgga tctagaaaag aaaaagcaat ccatgggcaa  2100
actgtattca ctcaaacaag atcttctttc aacactgaag aataagtcag tgacccagaa  2160
gacggaagca tggctggata ctttgcccg tgtgttgggat aatttagtcc aaaaacttga  2220
aaagagtaca gcacagattt cacaggctgt caccaccact cagccatcac taacacagac  2280
aactgtaatg gaaacagtaa ctacggtgac cacaagggaa cagatcctgg taaagcatgc  2340
tcaagaggaa cttccaccac cacctcccca aagaagagg cagattactg tggattctga  2400
aattaggaaa aggttggatg ttgatataac tgaacttcac agctggatta ctcgctcaga  2460
agctgtgttg cagagtcctg aatttgcaat cttttcggaag gaaggcaact tctcagactt  2520
aaaagaaaaa gtcaatgcca tagagcgaga aaaagctgag aagttcagaa aactgcaaga  2580
tgccagcaga tcagctcagg ccctggtgga acagatggtg aatgagggtg ttaatgcaga  2640
tagcatcaaa caagcctcag aacaactgaa cagccggtgg atcgaattct gccagttgct  2700
aagtgagaga cttaactggc tggagtatca gaacaacatc atcgctttct ataatcgact  2760
acaacaattg gagcagatga caactactgc tgaaaactgg ttgaaaatcc aacccaccac  2820
cccatcagag ccaacagcaa ttaaaagtca gttaaaaatt tgtaaggatg aagtcaaccg  2880
gctatcaggt cttcaacctc aaattgaacg attaaaaatt caaagcatag ccctgaaaga  2940
gaaaggacaa ggacccatgt tcctggatgc agactttgtg gccttacaa atcatttaa   3000
gcaagtcttt tctgatgtgc aggccagaga gaaagctca cagacaattt ttgacacttt  3060
gccaccaatg cgctatcagg agaccatgag tgccatcagg acatgggtcc agcagtcaga  3120
aaccaaactc tccatacctc aacttagtgt caccgactat gaaatcatgg agcagagact  3180
cgggaattg caggctttac aaagtttctct gcaagagcaa caagtggcc tatactatct  3240
cagcaccact gtgaaagaga gtcgaagaa agcgccctct gaaattagcc ggaaatatca  3300
atcagaattt gaagaaattg agggacgctg gaagagctcc tcccagc tggttgagca  3360
ttgtcaaaag ctagaggagc aaatgaataa actccgaaaa attcagaatc acatacaaac  3420
cctgaagaaa tggatggctg aagttgatgt ttttctgaag aggaatggc ctgcccttgg  3480
ggattcagaa attctaaaaa agcagctgaa acagtgcaga cttttagtca gtgatattca  3540
gacaattcag cccagtctaa acagtgtcaa tgaaggtggg cagaagataa agaatgaagc  3600
agagccagag tttgcttcga gacttgagac agaactcaaa gaacttaaca ctcagtggga  3660
```

```
tcacatgtgc caacaggtct atgccagaaa ggaggccttg aagggaggtt tggagaaaac  3720
tgtaagcctc cagaaagatc tatcagagat gcacgaatgg atgacacaag ctgaagaaga  3780
gtatcttgag agagattttg aatataaaac tccagatgaa ttacagaaag cagttgaaga  3840
gatgaagaga gctaaagaag aggcccaaca aaaagaagcg aaagtgaaac tccttactga  3900
gtctgtaaat agtgtcatag ctcaagctcc acctgtagca caagaggcct taaaaaagga  3960
acttgaaact ctaaccacca actaccagtg gctctgcact aggctgaatg ggaaatgcaa  4020
gactttggaa gaagtttggg catgttgcaa tgagttattg tcatacttgg agaaagcaaa  4080
caagtggcta aatgaagtag aatttaaact taaaaccact gaaaacattc ctggcggagc  4140
tgaggaaatc tctgaggtgc tagattcact tgaaaatttg atgcgacatt cagaggataa  4200
cccaaatcag attcgcatat tggcacagac cctaacagat ggcgagtca tggatgagct  4260
aatcaatgag gaacttgaga catttaattc tcgttggagg gaactacatg aagaggctgt  4320
aaggaggcaa aagttgcttg aacagagcat ccagtctgcc caggagactg aaaaatcctt  4380
acacttaatc caggagtccc tcacattcat tgacaagcag ttggcagctt atattgcaga  4440
caaggtggac gcagctcaaa tgcctcagga agcccaagaa atccaatctg atttgacaag  4500
tcatgagatc agtttagaag aaatgaagaa acataatcag gggaaggagg ctgcccaaag  4560
agtcctgtct cagattgatg ttgcacagaa aaaattacaa gatgtctcca tgaagtttcg  4620
attattccag aaaccagcca attttgagca gcgtctacaa gaaagtaaga tgatttaga   4680
tgaagtgaag atgcacttgc ctgcattgga acaaaagagt gtggaacagg aagtagtaca  4740
gtcacagcta aatcattgtg tgaacttgta taaaagtctg agtgaagtga agtctgaagt  4800
ggaaatggtg ataaagactg gacgtcagat tgtacagaaa aagcagacgg aaaatcccaa  4860
agaacttgat gaaagagtaa cagctttgaa attgcattat aatgagctgg gagcaaaggt  4920
aacagaaaga aagcaacagt tggagaaatg cttgaaattg tcccgtaaga tgcgaaagga  4980
aatgaatgtc ttgacagaat ggctggcagc tacagatatg gaattgacaa agagatcagc  5040
agttgaagga atgcctagta atttggattc tgaagttgcc tggggaaagg ctactcaaaa  5100
agagattgag aaacagaagg tgcacctgaa gagtatcaca gaggtaggag aggccttgaa  5160
aacagttttg ggcaagaagg agacgttggt ggaagataaa ctcagtcttc tgaatagtaa  5220
ctggatagct gtcacctccc gagcagaaga gtggttaaat cttttgttgg aataccagaa  5280
acacatggaa acttttgacc agaatgtgga ccacatcaca aagtggatca ttcaggctga  5340
cacacttttg gatgaatcag agaaaaagaa accccagcaa aaagaagacg tgcttaagcg  5400
tttaaaggca gaactgaatg acatacgccc aaaggtggac tctcacgtg accaagcagc  5460
aaacttgatg gcaaaccgcg gtgaccactg caggaaatta gtagagcccc aaatctcaga  5520
gctcaaccat cgatttgcag ccatttcaca cagaattaag actggaaagg cctccattcc  5580
tttgaaggaa ttggagcagt ttaactcaga tatacaaaaa ttgcttgaac cactggaggc  5640
tgaaattcag caggggtga atctgaaaga ggaagacttc aataaagata tgaatgaaga  5700
caatgagggt actgtaaaag aattgttgca aagaggagac aacttacaac aaagaatcac  5760
agatgagaga aagcgagagg aaataaagat aaaacagcag ctgttacaga caaaacataa  5820
tgctctcaag gatttgaggt ctcaagaag aaaaaaggct ctagaaattt ctcatcagtg  5880
gtatcagtac aagaggcagg ctgatgatct cctgaaatgc ttggatgaca ttgaaaaaaa  5940
attagccagc ctacctgagc ccagagatga aaggaaaata aaggaaattg atcgggaatt  6000
gcagaagaag aaaagaggagc tgaatgcagt gcgtaggcaa gctgagggct tgtctgagga  6060
tggggccgca atggcagtgg agccaactca gatccagctc agcaagcgct ggcgggaaat  6120
tgagagcaaa tttgctcagt ttcgaagact caactttgca caaattcaca ctgtccgtga  6180
agaaactgat atggtgatga ctgaagacat gcctttgaa atttcttatg tgccttctac  6240
ttatttgact gaaatcactc atgtctcaca agcccctatta gaagtggaac aacttctcaa  6300
tgctcctgac ctctgtgcta aggactttga agatctcttt aagcaagagg agtctctgaa  6360
gaatataaaa gatagtctac aacaaagctc aggtcggatt gacattattc atagcaagaa  6420
gacagcagca ttgcaaagtg caacgcctgt ggaaaggggt aagctacagg aagctctctc  6480
ccagcttgat ttccaatggg aaaagttaa caaaatgtac aaggaccgac aagggcgatt  6540
tgacagatct gttgagaaat ggcggcgttt tcattatgat ataaagatat ttaatcagtg  6600
gctaacagaa gctgaacagt ttctcagaaa gacacaaatt cctgagaatt gggaacatgc  6660
taaatacaaa tggtatctta aggaactcca ggatggcatt gggcagcgga aaactgttgt  6720
cagaacattg aatgcaactg gggaagaaat aattcagcaa tcctcaaaaa cagatgccaa  6780
tattctacag gaaaaattgg gaagcctgaa tctgcggtgg caggaggtct gcaaacagct  6840
gtcagacaga aaaaagaggc tagaagaaca aaagaatatc ttgtcagaat tcaaagaga   6900
tttaaatgaa tttgttttat ggttgaggag agcagataac attgctagta tcccacttga  6960
acctggaaaa gagcagcaac taaaagaaaa gcttgagcaa gtcaagttac tggtggaaga  7020
gttgccctg cgccagggaa ttctcaaaca attaaatgaa actggaggac ccgtgcttgt  7080
aagtgctccc ataagcccag aagagcaaga taaacttgaa aataagctca agcagacaaa  7140
tctccagtgg ataaaggttt ccagagcttt acctgagaaa caaggagaaa ttgaagctca  7200
aataaagac cttgggcagc ttgaaaaaaa gcttgaagac cttgaagagc agttaaatca  7260
tctgctgctg tggttatctc ctattaggaa tcagttggaa atttataacc aaccaaacca  7320
agaaggacca tttgacgttc aggaaactga aatagcagtt caagctaaac aaccggatgt  7380
ggaagagatt ttgtctaaag gcagcatttt gtacaaggaa aaaccagcca ctcagccagt  7440
gaagagagaa ttagaagatc tgagctctga gtggaaggga gtaaaccgtt tacttcaaga  7500
gctgagggca aagcagcctg acctagctcc tggactgacc actattggag cctctcctac  7560
tcagactgtt actctggtga cacaacctgt ggttactaag gaaactgcca tctccaaact  7620
agaaatgcca tcttccttga tgttggaggt acctgctctg gcagattca accgggcttg   7680
gacagaactt accgactggc tttctctgct tgatcaagtt ataaaatcac agagggtgat  7740
ggtgggtgac cttgaggata tcaacgagat gatcatcaag cagaaggcaa caatgcagga  7800
ttgaacag agcgtcccc agttggaaga actcattacc gctgcccaaa atttgaaaaa   7860
caagaccagc aatcaagagg ctagaacaat cattacggat cgaattgaaa gaattcagaa  7920
tcagtgggat gaagtacaag aacaccttca gaaccggagg caacagttga atgaaatgtt  7980
aaaggattca acacaatggc tggaagctaa ggaagaagct gagcaggtct taggacaggc  8040
cagagccaag cttgagtcag gaaggagggg tccctataca ggatgcaa tccaaaagaa   8100
aatcacagaa accaagcagt tggccaaaga cctccgccag tggcagacaa atgtagatgt  8160
ggcaaatgac ttgccctga acttctccg ggattattct gcagatgata ccagaaaagt   8220
ccacatgata acagagaata tcaatgcctc ttggagaagc attcataaaa gggtgagtga  8280
gcgagaggct gctttggaag aaactcatag attactgcaa cagttccccc tggacctgga  8340
aaagtttctt gcctggctta cagaagctga aacaactgcc aatgtcctac aggatgctac  8400
```

```
ccgtaaggaa aggctcctag aagactccaa gggagtaaaa gagctgatga aacaatggca   8460
agacctccaa ggtgaaattg aagctcacac agatgtttat cacaacctgg atgaaaacag   8520
ccaaaaaatc ctgagatccc tggaaggttc cgatgatgca gtcctgttac aaagacgttt   8580
ggataacatg aacttcaagt ggagtgaact tcggaaaaag tctctcaaca ttaggtccca   8640
tttggaagcc agttctgacc agtggaagcg tctgcacctt tctctgcagg aacttctggt   8700
gtggctacag ctgaaagatg atgaattaag ccggcaggca cctattggag gcgactttcc   8760
agcagttcag aagcagaacg atgtacatag ggccttcaag agggaattga aaactaaaga   8820
acctgtaatc atgagtactc ttgagactgt acgaatattt ctgacagagc agcctttgga   8880
aggactagag aaactctacc aggagcccag agagctgcct cctgaggaga gagcccagaa   8940
tgtcactcgg cttctacgaa agcaggctga ggaggtcaat actgagtggg aaaaattgaa   9000
cctgcactcc gctgactggc agagaaaaat agatgagacc cttgaaagac tccaggaact   9060
tcaagaggcc acgatgagc tggacctcaa gctgcgccaa gctgaggtga tcaagggatc   9120
ctggcagccc gtgggcgatc tcctcattga ctctctccaa gatcacctcg agaaagtcaa   9180
ggcacttcga ggagaaattg cgcctctgaa agagaacgtg agccacgtca atgaccttgc   9240
tcgccagctt accactttgg gcattcagct ctcaccgtat aacctcagca ctctggaaga   9300
cctgaacacc agatgaaagc ttctgcaggt ggccgtcgag gaccgagtca ggcagctgca   9360
tgaagcccac agggactttg gtccagcatc tcagcacttt ctttccacgt ctgtccaggg   9420
tccctgggag agagccatct cgccaaacaa agtgccctac tatatcaacc acgagactca   9480
aacaacttgc tgggaccatc ccaaaatgac agagctctac cagtctttag ctgacctgaa   9540
taatgtcaga ttctcagctt ataggactgc catgaaactc cgaagactgc agaaggccct   9600
ttgcttggat ctcttgagcc tgtcagctgc atgtgatgcc ttggaccagc acaacctcaa   9660
gcaaaatgac cagcccatgg atatcctgca gattattaat tgtttgacca ctatttatga   9720
ccgcctggag caagagcaca caatttggt caacgtccct ctctgcgtgg atatgtgtct   9780
gaactggctg ctgaatgttt atgatacggg acgaacaggg aggatccgtg tcctgtcttt   9840
taaaactggc atcatttccc tgtgtaaagc acatttggaa gacaagtaca gataccttt   9900
caagcaagtg gcaagttcaa caggattttg tgaccagcgg aggctgggcc tccttctgca   9960
tgattctatc caaattccaa gacagttggg tgaagttgca tcccttgggg gcagtaacat  10020
tgagccaagt gtccggagct gcttccaatt tgctaataat aagccagaga tcgaagcggc  10080
cctcttccta gactggatga gactggaacc ccagtccatg gtgtggctgc ccgtcctgca  10140
cagagtggct gctgcagaaa ctgccaagca tcaggccaaa tgtaacatct aacaagagtg  10200
tccaatcatt ggattcaggt acaggagtct aaagcacttt aattatgaca tctgccaaag  10260
ctgctttttt tctggtcgag ttgcaaaagg ccataaaatg cactatccca tggtggaata  10320
ttgcactccg actacatcag gagaagatgt tcgagacttt gccaaggtac taaaaaacaa  10380
atttcgaacc aaaaggtatt ttgcgaacca tccccgaagg ggctacctgc cagtgcagaa  10440
tgtcttagag ggggacaaca tggaaactcc cgttactcg atcaacttct ggccagtaga  10500
ttctgcgcct gcctcgtccc ctcagctttc acacgatgat actcattcac gcattgaaca  10560
ttatgctagc aggctagcag aaatggaaaa cagcaatgga tcttatctaa atgatagcat  10620
ctctcctaat gagagcatag atgatgaaca tttgttaatc cagcattact gccaaagttt  10680
gaaccaggac tcccccctga gccagcctcg tagtcctgcc cagatcttga tttccttaga  10740
gagtgaggaa agaggggagc tagagagaat cctagcagat cttgaggaag aaaacaggaa  10800
tctgcaagca gaatatgacc gtctaaagca gcagcacgaa cataaaggcc tgtccccact  10860
gccgtccct cctgaaatga tgcccacctc tccccagagt ccccgggatg ctgagctcat  10920
tgctgaggcc aagctactgc gtcaacacaa aggccgcctg gaagccagga tgcaaatcct  10980
ggaagaccac aataaacagc tggagtcaca gttacacagg ctaaggcagc tgctggagca  11040
accccaggca gaggccaaag tgaatggcac aacggtgtcc tctccttcta cctctctaca  11100
gaggtccgac agcagtcagc ctatgctgct ccgagtggtt ggcagtcaaa cttcggactc  11160
catgggtgag gaagatcttc tcagtcctcc ccaggacaca agcacaggt tagaggaggt  11220
gatgagcaa ctcaacaact ccttccctag ttcaagagga gaaatccc ctggaaagcc  11280
aatgagagag gacacaatgt aggaagtctt ttccacatgg cagatgattt gggcagagcg  11340
atggagtcct tagtatcagt catgacagat gaagaaggag cagaataaat gttttacaac  11400
tcctgattcc cgcatggttt ttataatatt catacaacaa agaggattag acagtaagag  11460
tttacaagaa ataaatctat attttttgtga agggtagtgg tattatactg tagatttcag  11520
tagtttctaa gtctgttatt gttttgttaa caatggcagg ttttacacgt ctatgcaatt  11580
gtacaaaaaa gttataagaa aactacatgt aaaatcttga tagctaaata acttgccatt  11640
tctttatatg gaacgcattt tgggttgttt aaaaattat aacagttata aagaaagatt  11700
gtaaactaaa gtgtgcttta taaaaaaaag ttgtttataa aaaccccta aaacaaaaca  11760
aacacacaca cacacacata cacacacaca cacaaaactt tgaggcagcg cattgttttg  11820
catccttttg gcgtgatatc catatgaaat tcatggcttt ttcttttttt gcatattaaa  11880
gataagactt cctctaccac cacaccaaat gactactaca cactgctcat ttgagaactg  11940
tcagctgagt ggggcaggct tgagttttca tttcatatat ctatatgtct ataagtatat  12000
aaatactata gttatataga taagagata cgaattccta tagactgact ttttccattt  12060
tttaaatgtt catgtcacat cctaatgaaa agaaattact tctagtcagt catccaggct  12120
tacctgcttg gtctagaatg gattttccc ggagccggaa gccaggagga aactacacca  12180
cactaaaaca ttgtctacag ctccagatgt ttctcatttt aaaacaacttt ccactgacaa  12240
cgaaagtaaa gtaaagtatt ggatttttt aaagggaaca tgtgaatgaa tacacaggac  12300
ttattatatc agagtgagta atcggttggt tggttgattg attgattgat tgatacattc  12360
agcttcctgc tgctagcaat gccacgattt agatttaatg atgcttcagt ggaaatcaat  12420
cagaaggtat tctgaccttg tgaacatcag aaggtatttt ttaactccca agcagtagca  12480
ggacgatgat agggctggag ggctatggat tcccagccca tccctgtgaa ggagtaggcc  12540
actcttaagg tgaaggattg gatgattgtt cataatacat aaagttctct gtaattacaa  12600
ctaaattatt atgccctctt ctcacagtca aaaggaactg ggtggtttgg ttttgttgc  12660
tttttagat ttattgtccc atgtgggatg agttttaaa tgccacaaga cataatttaa  12720
aataaataaa ctttgggaaa aggtgtaaaa cagtagcccc atcacattg tgatactgac  12780
aggtatcaac ccagaagccc atgaactgtg tttccatcct tgcatttct ctgcgagtag  12840
ttccacacag gtttgtaagt aagtaagaaa gaaggcaaat tgattcaaat gttacaaaaa  12900
aaccccttctt ggtggattag acaggttaaa tatataaaca aacaaacaaa aattgctcaa  12960
aaagaggag aaaagctcaa gaggaaaagc taaggactgg taggaaaaag ctttactctt  13020
tcatgccatt ttatttcttt ttgatttta aatcattcat tcaatagata ccaccgtgtg  13080
acctataatt ttgcaaatct gttacctctg acatcaagtg taattagctt ttggagagtg  13140
```

```
ggctgacatc aagtgtaatt agcttttgga gagtgggttt tgtccattat taataattaa  13200
ttaattaaca tcaaacacgg cttctcatgc tatttctacc tcactttggt tttggggtgt  13260
tcctgataat tgtgcacacc tgagttcaca gcttcaccac ttgtccattg cgttattttc  13320
tttttccttt ataattcttt cttttcctt cataattttc aaaagaaaac ccaaagctct   13380
aaggtaacaa attaccaaat tacatgaaga tttggttttt gtcttgcatt tttttccttt  13440
atgtgacgct ggacctttc tttacccaag gattttaaa actcagattt aaaacaaggg   13500
gttactttac atcctactaa gaagtttaag taagtaagtt tcattctaaa atcagaggta  13560
aatagagtgc ataaataatt ttgttttaat cttttgttt ttcttttaga cacattagct   13620
ctggagtgag tctgtcataa tatttgaaca aaaattgaga gctttattgc tgcattttaa  13680
gcataattaa tttggacatt atttcgtgtt gtgttcttta taaccaccaa gtattaaact  13740
gtaaatcata atgtaactga agcataaaca tcacatggca tgttttgtca ttgtttttcag 13800
gtactgagtt cttacttgag tatcataata tattgtgttt taacaccaac actgtaacat  13860
ttacgaatta tttttttaaa cttcagtttt actgcatttt cacaacatat cagacttcac  13920
caaatatatg ccttactatt gtattatagt actgctttac tgtgtatctc aataaagcac  13980
gcagttatgt tac                                                     13993

SEQ ID NO: 296       moltype = DNA  length = 30
FEATURE              Location/Qualifiers
source               1..30
                     mol_type = other DNA
                     organism = synthetic construct
SEQUENCE: 296
ctccaacatc aaggaagatg gcatttctag                                       30
```

MUSCLE TARGETING COMPLEXES AND USES THEREOF FOR TREATING DYSTROPHINOPATHIES

RELATED APPLICATIONS

This application is a continuation of U.S. application Ser. No. 18/181,623, entitled "MUSCLE TARGETING COMPLEXES AND USES THEREOF FOR TREATING DYSTROPHINOPATHIES", filed Mar. 10, 2023, which is a continuation of U.S. application Ser. No. 17/930,522, entitled "MUSCLE TARGETING COMPLEXES AND USES THEREOF FOR TREATING DYSTROPHINOPATHIES", filed Sep. 8, 2022, now U.S. Pat. No. 11,633,496, which is a continuation of U.S. application Ser. No. 17/751,875, entitled "MUSCLE TARGETING COMPLEXES AND USES THEREOF FOR TREATING DYSTROPHINOPATHIES", filed May 24, 2022, now U.S. Pat. No. 11,497,815, which is a continuation of U.S. application Ser. No. 17/580,844, entitled "MUSCLE TARGETING COMPLEXES AND USES THEREOF FOR TREATING DYSTROPHINOPATHIES", filed Jan. 21, 2022, now U.S. Pat. No. 11,369,689, which is a continuation of U.S. application Ser. No. 17/501,066, entitled "MUSCLE TARGETING COMPLEXES AND USES THEREOF FOR TREATING DYSTROPHINOPATHIES", filed Oct. 14, 2021, now U.S. Pat. No. 11,248,056, which is a continuation of U.S. application Ser. No. 17/205,151, entitled "MUSCLE TARGETING COMPLEXES AND USES THEREOF FOR TREATING DYSTROPHINOPATHIES", filed Mar. 18, 2021, now U.S. Pat. No. 11,168,141, which is a continuation of U.S. application Ser. No. 17/265,024, entitled "MUSCLE TARGETING COMPLEXES AND USES THEREOF FOR TREATING DYSTROPHINOPATHIES", filed Feb. 1, 2021, which is a national stage filing under 35 U.S.C. § 371 of International Application No. PCT/US2019/044949, entitled "MUSCLE TARGETING COMPLEXES AND USES THEREOF FOR TREATING DYSTROPHINOPATHIES", filed Aug. 2, 2019, which claims the benefit of the filing date of U.S. Provisional Application No. 62/714,031, entitled "MUSCLE TARGETING COMPLEXES AND USES THEREOF FOR TREATING DYSTROPHINOPATHIES", filed Aug. 2, 2018; and U.S. Provisional Application No. 62/855,766, entitled "MUSCLE TARGETING COMPLEXES AND USES THEREOF FOR TREATING DYSTROPHINOPATHIES", filed May 31, 2019; the contents of each of which are incorporated herein by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO AN ELECTRONIC SEQUENCE LISTING

The contents of the electronic sequence listing (D082470008US09-SEQ-COB.xml; Size: 392,178 bytes; and Date of Creation: Oct. 19, 2023) are herein incorporated by reference in their entirety.

BACKGROUND OF INVENTION

Dystrophinopathies are a group of distinct neuromuscular diseases that result from mutations in dystrophin gene. Dystrophinopathies include Duchenne muscular dystrophy, Becker muscular dystrophy, and X-linked dilated cardiomyopathy. Dystrophin (DMD) is a large gene, containing 79 exons and ~2.6 million total base pairs. Numerous mutations in DMD, including exonic frameshift, deletion, substitution, and duplicative mutations, are able to diminish the expression of functional dystrophin, leading to dystrophinopathies. One agent that targets exon 51 of human DMD, eteplirsen, has been preliminarily approved by the U.S. Food and Drug Administration (FDA) however its efficacy is still being evaluated.

SUMMARY OF INVENTION

According to some aspects, the disclosure provides complexes that target muscle cells for purposes of delivering molecular payloads to those cells. In some embodiments, complexes provided herein are particularly useful for delivering molecular payloads that increase or restore expression or activity of functional DMD. In some embodiments, complexes comprise oligonucleotide based molecular payloads that promote normal expression of functional DMD through an in-frame exon skipping mechanism or suppression of stop codons. In other embodiments, complexes are configured for delivering a mini-dystrophin gene or synthetic mRNA that increases or restores functional dystrophin activity. Accordingly, in some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor mediated internalization, following which the molecular payload may be released to perform a function inside the cells. For example, complexes engineered to deliver oligonucleotides may release the oligonucleotides such that the oligonucleotides can promote expression of functional DMD (e.g., through an exon skipping mechanism) in the muscle cells. In some embodiments, the oligonucleotides are released by endosomal cleavage of covalent linkers connecting oligonucleotides and muscle-targeting agents of the complexes.

Some aspects of the disclosure comprise a complex comprising a muscle-targeting agent covalently linked to a molecular payload configured for promoting the expression or activity of a DMD, wherein the muscle-targeting agent specifically binds to an internalizing cell surface receptor on muscle cells.

In some embodiments, the muscle-targeting agent is a muscle-targeting antibody. In some embodiments, a muscle-targeting antibody is an antibody that specifically binds to an extracellular epitope of a transferrin receptor (e.g., an epitope of the apical domain of the transferrin receptor). A muscle-targeting antibody may specifically binds to an epitope of a sequence in the range of C89 to F760 of SEQ ID NO: 1-3. In some embodiments, the equilibrium dissociation constant (Kd) of binding of a muscle-targeting antibody to a transferrin receptor is in a range from $10^{-11}$ M to $10^{-6}$ M.

In some embodiments, a muscle-targeting antibody of a complex competes for specific binding to an epitope of a transferrin receptor with an antibody listed in Table 1 (e.g., competes for specific binding to an epitope of a transferrin receptor with an Kd of less than or equal to $10^{-6}$ M, e.g., in a range of $10^{-11}$ M to $10^{-6}$ M).

In some embodiments, a muscle-targeting antibody of a complex does not specifically bind to the transferrin binding site of a transferrin receptor and/or does not inhibit binding of transferrin to a transferrin receptor. In some embodiments, a muscle-targeting antibody of a complex is cross-reactive with extracellular epitopes of two or more of a human, non-human primate and rodent transferrin receptor. In some embodiments, a muscle-targeting antibody of a complex is configured to promote transferrin receptor mediated internalization of the molecular payload into a muscle cell.

A muscle-targeting antibody (e.g., muscle-targeting antibody is an antibody that specifically binds to an extracellular epitope of a transferrin receptor) is a chimeric antibody, wherein optionally the chimeric antibody is a humanized monoclonal antibody. A muscle-targeting antibody may be in the form of a ScFv, Fab fragment, Fab' fragment, F(ab')$_2$ fragment, or Fv fragment.

In some embodiments, a molecular payload of a complex is an oligonucleotide. In some embodiments, an oligonucleotide comprises a sequence listed in Table 2. In some embodiments, an oligonucleotide comprises a sequence as provided in any one of SEQ ID NO: 15-266. In some embodiments, an oligonucleotide comprises a region of complementarity to a mutated DMD allele.

In some embodiments, an oligonucleotide is configured to suppress a truncating mutation in a DMD allele by mono- or multi-exon skipping. In some embodiments, an oligonucleotide promotes antisense-mediated exon skipping to produce in-frame dystrophin mRNA. In some embodiments, an oligonucleotide promotes skipping of an exon of DMD in the range of exon 8 to exon 55 (e.g., exon 23 to exon 53). In some embodiments, an oligonucleotide promotes skipping of exon 8, exon 23, exon 44, exon 45, exon 50, exon 51, exon 52, exon 53, and/or exon 55. In some embodiments, an oligonucleotide promotes skipping of multiple exons in the range of exon 44 to exon 53.

An oligonucleotide of the disclosure may comprise at least one modified internucleotide linkage (e.g., a phosphorothioate linkage). In some embodiments, an oligonucleotide comprises phosphorothioate linkages in the Rp stereochemical conformation and in the Sp stereochemical conformation. In some embodiments, an oligonucleotide comprises phosphorothioate linkages that are all in the Rp stereochemical conformation. In other embodiments, an oligonucleotide comprises phosphorothioate linkages that are all in the Sp stereochemical conformation.

An oligonucleotide of the disclosure may comprise one or more modified nucleotides (e.g., 2'-modified nucleotides). In some embodiments, a modified nucleotide is a 2'-O-methyl, 2'-fluoro (2'-F), 2'-O-methoxyethyl (2'-MOE), or 2',4'-bridged nucleotide. In some embodiments, a modified nucleotides is a bridged nucleotide (e.g., selected from: 2'4'-constrained 2'-O-ethyl (cEt) and locked nucleic acid (LNA) nucleotides).

In some embodiments, an oligonucleotide is a gapmer oligonucleotide that directs RNAse H-mediated cleavage of an miRNA that negatively regulates DMD expression in a cell, optionally wherein the miRNA is miR-31. A gapmer oligonucleotide may comprise a central portion of 5 to 15 deoxyribonucleotides flanked by wings of 2 to 8 modified nucleotides (e.g., 2'-modified nucleotides).

In some embodiments, an oligonucleotide is a mixmer oligonucleotide. In some embodiments, a mixmer oligonucleotide promotes exon skipping. A mixmer oligonucleotide may comprise two or more different 2' modified nucleotides.

In some embodiments, an oligonucleotide is an RNAi oligonucleotide that promotes RNAi-mediated cleavage of an miRNA that negatively regulates DMD expression in a cell, optionally wherein the miRNA is miR-31. An RNAi oligonucleotide may be a double-stranded oligonucleotide of 19 to 25 nucleotides in length. In some embodiments, an RNAi oligonucleotide comprises at least one 2' modified nucleotide.

In some embodiments, an oligonucleotide comprises a guide sequence for a genome editing nuclease.

In some embodiments, an oligonucleotide is a phosphorodiamidite morpholino oligomer (PMO).

In other embodiments, a molecular payload is a polypeptide. In some embodiments, a molecular payload is a polypeptide that is a functional fragment of dystrophin protein.

In some embodiments, a muscle-targeting agent is covalently linked to a molecular payload via a cleavable linker (e.g., a protease-sensitive linker, pH-sensitive linker, or glutathione-sensitive linker). A protease-sensitive linker may comprise a sequence cleavable by a lysosomal protease and/or an endosomal protease. In some embodiments, a protease-sensitive linker comprises a valine-citrulline dipeptide sequence. A pH-sensitive linker may be cleaved at a pH in a range of 4 to 6.

In some embodiments, a muscle-targeting agent is covalently linked to a molecular payload via a non-cleavable linker (e.g., an alkane linker).

In some embodiments, a muscle-targeting antibody comprises a non-natural amino acid to which an oligonucleotide can be covalently linked. In some embodiments, a muscle-targeting antibody is covalently linked to an oligonucleotide via conjugation to a lysine residue or a cysteine residue of the antibody. In some embodiments, an oligonucleotide is conjugated to a cysteine residue of the antibody via a maleimide-containing linker, optionally wherein the maleimide-containing linker comprises a maleimidocaproyl or maleimidomethyl cyclohexane-1-carboxylate group.

In some embodiments, a muscle-targeting antibody is a glycosylated antibody that comprises at least one sugar moiety to which a oligonucleotide is covalently linked. In some embodiments, a glycosylated antibody that comprises at least one sugar moiety that is a branched mannose. In some embodiments, a muscle-targeting antibody is a glycosylated antibody that comprises one to four sugar moieties each of which is covalently linked to a separate oligonucleotide. In some embodiments, a muscle-targeting antibody is a fully-glycosylated antibody or a partially-glycosylated antibody. A partially-glycosylated antibody may be produced via chemical or enzymatic means. In some embodiments, a partially-glycosylated antibody is produced in a cell that is deficient for an enzyme in the N- or O-glycosylation pathway.

Some aspects of the disclosure comprise a method of delivering an molecular payload to a cell expressing transferrin receptor. In some embodiments, methods of delivering an molecular payload to a cell expressing transferrin receptor comprise contacting the cell with a complex comprising a muscle-targeting agent covalently linked to a molecular payload configured for promoting the expression or activity of a DMD.

Some aspects of the disclosure comprise a method of promoting the expression or activity of a DMD protein in a cell. In some embodiments, methods of promoting the expression or activity of a DMD protein in a cell comprise contacting the cell with a complex comprising a muscle-targeting agent covalently linked to a molecular payload configured for promoting the expression or activity of a DMD in an amount effective for promoting internalization of the molecular payload to the cell. In some embodiments, the cell is in vitro. In some embodiments, the cell is in a subject. In some embodiments, the subject is a human.

Further aspects of the disclosure comprise a method of treating a subject having a mutated DMD allele that is associated with a dystrophinopathy. In some embodiments, methods of treating a subject having a mutated DMD allele that is associated with a dystrophinopathy comprise administering to the subject an effective amount of a complex comprising a muscle-targeting agent covalently linked to a molecular payload configured for promoting the expression or activity of a DMD.

Yet further aspects of the disclosure comprise a method of promoting skipping of an exon of a DMD mRNA transcript in a cell. In some embodiments, methods of promoting skipping of an exon of a DMD mRNA transcript comprise administering to the cell an effective amount of the complex comprising a muscle-targeting agent covalently linked to a molecular payload configured for promoting the expression or activity of a DMD. In some embodiments, methods promote skipping of exon 8, exon 23, exon 44, exon 45, exon 50, exon 51, exon 52, exon 53, and/or exon 55 of the DMD mRNA transcript.

DETAILED DESCRIPTION OF INVENTION

Figure 1:
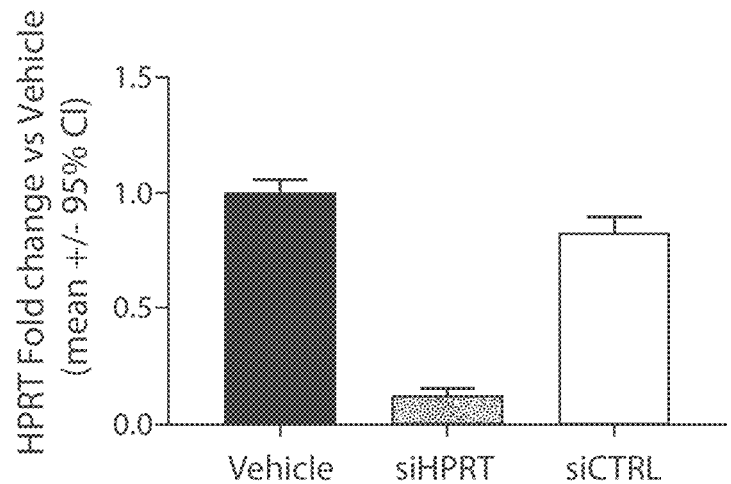
FIG. 1 depicts a non-limiting schematic showing the effect of transfecting cells with an siRNA.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that modulate (e.g., promote) the expression or activity of target genes in muscle cells, e.g., in a subject having or suspected of having a rare muscle disease. For example, in some embodiments, complexes are provided for targeting DMD, e.g., a mutated DMD allele. In some embodiments, complexes provided herein may comprise oligonucleotides that promote normal expression and activity of DMD. As another example, complexes may comprise oligonucleotides that induce skipping of exon of DMD mRNA. In some embodiments, synthetic nucleic acid payloads (e.g., DNA or RNA payloads) may be used that express one or more proteins that promote normal expression and activity of DMD.

In some embodiments, complexes may comprise molecular payloads of synthetic cDNAs and/or synthetic mRNAs, e.g., that express dystrophin or fragments thereof (e.g., a dystrophin mini gene). In some embodiments, complexes may comprise molecular payloads such as guide molecules (e.g., guide RNAs) that are capable of targeting nucleic acid programmable nucleases (e.g., Cas9) to a sequence at or near a disease-associated mutation of DMD, e.g., a mutated DMD exon. In some embodiments, such nucleic programmable nucleases could be used to cleave part or all of a disease-associated mutation of DMD, e.g., a mutated DMD exon, to promote expression of functional DMD. In some embodiments, complexes may comprise molecular payloads that upregulate the expression and/or activity of genes that can replace the function of dystrophin, such as utrophin.

Further aspects of the disclosure, including a description of defined terms, are provided below.

I. Definitions

Administering: As used herein, the terms "administering" or "administration" means to provide a complex to a subject in a manner that is physiologically and/or pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1. CH2, and/or CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferring receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

DMD: As used herein, the term "DMD" refers to a gene that encodes dystrophin protein, a key component of the dystrophin-glycoprotein complex, which bridges the inner cytoskeleton and the extracellular matrix in muscle cells, particularly muscle fibers. Deletions, duplications, and point mutations in DMD may cause dystrophinopathies, such as Duchenne muscular dystrophy, Becker muscular dystrophy, or cardiomyopathy. Alternative promoter usage and alternative splicing result in numerous distinct transcript variants and protein isoforms for this gene. In some embodiments, a dystrophin gene may be a human (Gene ID: 1756), non-human primate (e.g., Gene ID: 465559), or rodent gene (e.g., Gene ID: 13405: Gene ID: 24907). In addition, multiple human transcript variants (e.g., as annotated under GenBank RefSeq Accession Numbers: NM_000109.3, NM_004006.2 (SEQ ID NO: 295), NM_004009.3, NM_004010.3 and NM_004011.3) have been characterized that encode different protein isoforms.

DMD allele: As used herein, the term "DMD allele" refers to any one of alternative forms (e.g., wild-type or mutant forms) of a DMD gene. In some embodiments, a DMD allele may encode for dystrophin that retains its normal and typical functions. In some embodiments, a DMD allele may comprise one or more mutations that results in muscular dystrophy. Common mutations that lead to duchenne muscular dystrophy involve frameshift, deletion, substitution, and duplicative mutations of one or more of 79 exons present in a dystrophin allele, e.g., exon 8, exon 23, exon 41, exon 44, exon 50, exon 51, exon 52, exon 53, or exon 55. Further examples of DMD mutations are disclosed, for example, in Flanigan K M, et al., Mutational spectrum of DMD mutations in dystrophinopathy patients: application of modern diagnostic techniques to a large cohort. Hum Mutat. 2009 December; 30 (12):1657-66, the contents of which are incorporated herein by reference in its entirety.

Dystrophinopathy: As used herein, the term "dystrophinopathy" refers to a muscle disease results from one or more mutated DMD alleles. Dystrophinopathies include a spectrum of conditions (ranging from mild to severe) that includes Duchenne muscular dystrophy, Becker muscular dystrophy, and DMD-associated dilated cardiomyopathy (DCM). In some embodiments, at one end of the spectrum, dystrophinopathy is phenotypically associated with an asymptomatic increase in serum concentration of creatine phosphokinase (CK) and/or muscle cramps with myoglobinuria. In some embodiments, at the other end of the spectrum, dystrophinopathy is phenotypically associated with progressive muscle diseases that are generally classified as Duchenne or Becker muscular dystrophy when skeletal muscle is primarily affected and as DMD-associated dilated cardiomyopathy (DCM) when the heart is primarily affected. Symptoms of Duchenne muscular dystrophy include muscle loss or degeneration, diminished muscle function, pseudo-hypertrophy of the tongue and calf muscles, higher risk of neurological abnormalities, and a shortened lifespan. Duchenne muscular dystrophy is associated with Online Mendelian Inheritance in Man (OMIM) Entry #310200. Becker muscular dystrophy is associated with OMIM Entry #300376. Dilated cardiomyopathy is associated with OMIM Entry X #302045.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation. e.g., ligand binding to the receptor. In some embodiments. an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services. NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O-methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W E., (2002) Clin. Biochem. 35:425-445; Gavilondo J. V., and Larrick J. W. (2002) BioTechniques 29:128-145: Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S A., and Green L. L. (2002) Current Opinion in Biotechnology 13:593-597: Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of a oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having a disease resulting from a mutated DMD gene sequence, e.g., a mutation in an exon of a DMD gene sequence. In some embodiments, a subject has a dystrophinopathy, e.g., Duchenne muscular dystrophy.

Transferrin receptor: As used herein, the term, "transferrin receptor" (also known as TFRC, CD71, p90, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

II. Complexes

Provided herein are complexes that comprise a targeting agent, e.g. an antibody, covalently linked to a molecular payload. In some embodiments, a complex comprises a muscle-targeting antibody covalently linked to a oligonucleotide. A complex may comprise an antibody that specifically binds a single antigenic site or that binds to at least two antigenic sites that may exist on the same or different antigens.

A complex may be used to modulate the activity or function of at least one gene, protein, and/or nucleic acid. In some embodiments, the molecular payload present with a complex is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a disease-associated repeat in muscle cells.

In some embodiments, a complex comprises a muscle-targeting agent, e.g. an anti-transferrin receptor antibody, covalently linked to a molecular payload, e.g. a mixmer antisense oligonucleotide that targets a mutated DMD allele to promote exon skipping.

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" *Nature* 1988; 333: 861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" *J Biol Chem* 1996; 271: 15160-5; and Weisbart R. H. et al., "Cell type specific targeted intracellular delivery into muscle of a monoclonal antibody that binds myosin IIb" *Mol Immunol*, 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to as an anti-transferrin receptor antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or derivatized using several known methodologies, e.g. library design using phage display. Exemplary methodologies have been characterized in the art and are incorporated by reference (Diez, P. et al. "High-throughput phage-display screening in array format", Enzyme and microbial technology, 2015, 79, 34-41; Christoph M. H. and Stanley, J. R. "Antibody Phage Display: Technique and Applications" J Invest Dermatol, 2014, 134:2; Engleman, Edgar (Ed.) "Human Hybridomas and Monoclonal Antibodies." 1985, Springer). In other embodiments, an anti-transferrin antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same": U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052).

Any appropriate anti-transferrin receptor antibodies may be used in the complexes disclosed herein. Examples of anti-transferrin receptor antibodies, including associated references and binding epitopes are listed in Table 1. In some embodiments, the anti-transferrin receptor antibody comprises the complementarity determining regions (CDR-H1, CDR-H2, CDR-H3, CDR-L1, CDR-L2, and CDR-L3) of any of the anti-transferrin receptor antibodies provided herein, e.g., anti-transferrin receptor antibodies listed in Table 1.

TABLE 1

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522 | Apical domain of TfR (residues 305-366 of human TfR sequence XM_052730.3, available in GenBank) |

TABLE 1-continued

List of anti-transferrin receptor antibody clones, including associated references and binding epitope information.

| Antibody Clone Name | Reference(s) | Epitope/Notes |
|---|---|---|
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |
| (From Genentech) 7A4, 8A2, 15D2, 10D11, 7B10, 15G11, 16G5, 13C3, 16G4, 16F6, 7G7, 4C2, 1B12, and 13D4 | WO 2016/081643, filed 5/26/2016, entitled "ANTI-TRANSFERRIN RECEPTOR ANTIBODIES AND METHODS OF USE" U.S. Pat. No. 9,708,406, filed May 20, 2014, "Anti-transferrin receptor antibodies and methods of use" | Apical domain and non-apical regions |
| (From Armagen) 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. US Patent App. 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A Streptococcus invasion. Cellular microbiology. 16: 1806-21. | |
| DF1513 | Ortiz-Zapater E et al. Trafficking of the human transferrin receptor in plant cells: effects of tyrphostin A23 and brefeldin A. Plant J 48:757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149 ER-MP21, YTA74.4, BU54, 2B6, RI7 217 | Commercially available anti-transferrin receptor antibodies. | Novus Biologicals 8100 Southpark Way, A-8 Littleton CO 80120 |
| (From INSERM) BA120g | US Patent App. 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I.S. et al. "Anti-transferrin receptor monoclonal antibody and toxin-antibody conjugates affect growth of human tumour cells." Nature, 1981, volume 294, pages 171-173 | |
| R17 217.1.3, SE9C11, OKT9 (BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K.C. et al. "Transferrin receptors in human tissues: their distribution and possible clinical relevance." J Clin Pathol. 1983 May;36(5):539-45. | |

In some embodiments, the muscle-targeting agent is an anti-transferrin receptor antibody. In some embodiment, an anti-transferrin receptor antibody specifically binds to a transferrin protein having an amino acid sequence as disclosed herein. In some embodiments, an anti-transferrin receptor antibody may specifically bind to any extracellular epitope of a transferrin receptor or an epitope that becomes exposed to an antibody, including the apical domain, the transferrin binding domain, and the protease-like domain. In some embodiments, an anti-transferrin receptor antibody binds to an amino acid segment of a human or non-human primate transferrin receptor, as provided in SEQ ID Nos. 1-3 in the range of amino acids C89 to F760. In some embodiments, an anti-transferrin receptor antibody specifically binds with binding affinity of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. Anti-transferrin receptor antibodies used herein may be capable of competing for binding with other anti-transferrin receptor antibodies, e.g. OKT9, 8D3, that bind to transferrin receptor with $10^{-3}$ M, $10^{-4}$ M, $10^{-5}$ M, $10^{-6}$ M, $10^{-7}$ M, or less.

An example human transferrin receptor amino acid sequence, corresponding to NCBI sequence NP_003225.2 (transferrin receptor protein 1 isoform 1, *Homo sapiens*) is as follows:

(SEQ ID NO: 1)
MMDQARSAFSNLFGGEPLSYTRFSLARQVDGDNSHVEMKLAVDEEENAD

NNTKANVTKPKRCSGSICYGTIAVIVFFLIGFMIGYLGYCKGVEPKTEC

ERLAGTESPVREEPGEDFPAARRLYWDDLKRKLSEKLDSTDFTGTIKLL

NENSYVPREAGSQKDENLALYVENQFREFKLSKVWRDQHFVKIQVKDSA

QNSVIIVDKNGRLVYLVENPGGYVAYSKAATVTGKLVHANFGTKKDFED

LYTPVNGSIVIVRAGKITFAEKVANAESLNAIGVLIYMDQTKFPIVNAE

LSFFGHAHLGTGDPYTPGFPSFNHTQFPPSRSSGLPNIPVQTISRAAAE

KLFGNMEGDCPSDWKTDSTCRMVTSESKNVKLTVSNVLKEIKILNIFGV

IKGFVEPDHYVVVGAQRDAWGPGAAKSGVGTALLLKLAQMFSDMVLKDG

FQPSRSIIFASWSAGDFGSVGATEWLEGYLSSLHLKAFTYINLDKAVLG

TSNFKVSASPLLYTLIEKTMQNVKHPVTGQFLYQDSNWASKVEKLTLDN

AAFPFLAYSGIPAVSFCFCEDTDYPYLGTTMDTYKELIERIPELNKVAR

-continued

AAAEVAGQFVIKLTHDVELNLDYERYNSQLLSFVRDLNQYRADIKEMGL

SLQWLYSARGDFFRATSRLTTDFGNAEKTDRFVMKKLNDRVMRVEYHFL

SPYVSPKESPFRHVFWGSGSHTLPALLENLKLRKQNNGAFNETLFRNQL

ALATWTIQGAANALSGDVWDIDNEF.

An example non-human primate transferrin receptor amino acid sequence, corresponding to NCBI sequence NP_001244232.1 (transferrin receptor protein 1, *Macaca mulatta*) is as follows:

(SEQ ID NO: 2)
MMDQARSAFSNLFGGEPLSYTRFSLARQVDGDNSHVEMKLGVDEEENTD

NNTKPNGTKPKRCGGNICYGTIAVIIFFLIGFMIGYLGYCKGVEPKTEC

ERLAGTESPAREEPEEDFPAAPRLYWDDLKRKLSEKLDTTDFTSTIKLL

NENLYVPREAGSQKDENLALYIENQFREFKLSKVWRDQHFVKIQVKDSA

QNSVIIVDKNGGLVYLVENPGGYVAYSKAATVTGKLVHANFGTKKDFED

LDSPVNGSIVIVRAGKITFAEKVANAESLNAIGVLIYMDQTKFPIVKAD

LSFFGHAHLGTGDPYTPGFPSFNHTQFPPSQSSGLPNIPVQTISRAAAE

KLFGNMEGDCPSDWKTDSTCKMVTSENKSVKLTVSNVLKETKILNIFGV

IKGFVEPDHYVVVGAQRDAWGPGAAKSSVGTALLLKLAQMFSDMVLKDG

FQPSRSIIFASWSAGDFGSVGATEWLEGYLSSLHLKAFTYINLDKAVLG

TSNFKVSASPLLYTLIEKTMQDVKHPVTGRSLYQDSNWASKVEKLTLDN

AAFPFLAYSGIPAVSFCFCEDTDYPYLGTTMDTYKELVERIPELNKVAR

AAAEVAGQFVIKLTHDTELNLDYERYNSQLLLFLRDLNQYRADVKEMGL

SLQWLYSARGDFFRATSRLTTDFRNAEKRDKFVMKKLNDRVMRVEYYFL

SPYVSPKESPFRHVFWGSGSHTLSALLESLKLRRQNNSAFNETLFRNQL

ALATWTIQGAANALSGDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 3)
MMDQARSAFSNLFGGEPLSYTRFSLARQVDGDNSHVEMKLGVDEEENTD

NNTKANGTKPKRCGGNICYGTIAVIIFFLIGFMIGYLGYCKGVEPKTEC

ERLAGTESPAREEPEEDFPAAPRLYWDDLKRKLSEKLDTTDFTSTIKLL

NENLYVPREAGSQKDENLALYIENQFREFKLSKVWRDQHFVKIQVKDSA

QNSVIIVDKNGGLVYLVENPGGYVAYSKAATVTGKLVHANFGTKKDFED

LDSPVNGSIVIVRAGKITFAEKVANAESLNAIGVLIYMDQTKFPIVKAD

LSFFGHAHLGTGDPYTPGFPSFNHTQFPPSQSSGLPNIPVQTISRAAAE

KLFGNMEGDCPSDWKTDSTCKMVTSENKSVKLTVSNVLKETKILNIFGV

IKGFVEPDHYVVVGAQRDAWGPGAAKSSVGTALLLKLAQMFSDMVLKDG

FQPSRSIIFASWSAGDFGSVGATEWLEGYLSSLHLKAFTYINLDKAVLG

TSNFKVSASPLLYTLIEKTMQDVKHPVTGRSLYQDSNWASKVEKLTLDN

AAFPFLAYSGIPAVSFCFCEDTDYPYLGTTMDTYKELVERIPELNKVAR

AAAEVAGQFVIKLTHDTELNLDYERYNSQLLLFLRDLNQYRADVKEMGL

SLQWLYSARGDFFRATSRLTTDFRNAEKRDKFVMKKLNDRVMRVEYYFL

SPYVSPKESPFRHVFWGSGSHTLSALLESLKLRRQNNSAFNETLFRNQL

ALATWTIQGAANALSGDVWDIDNEF.

An example mouse transferrin receptor amino acid sequence, corresponding to NCBI sequence NP_001344227.1 (transferrin receptor protein 1, *Mus musculus*) is as follows:

(SEQ ID NO: 4)
MMDQARSAFSNLFGGEPLSYTRFSLARQVDGDNSHVEMKLAADEEENAD

NNMKASVRKPKRFNGRLCFAAIALVIFFLIGFMSGYLGYCKRVEQKEEC

VKLAETEETDKSETMETEDVPTSSRLYWADLKTLLSEKLNSIEFADTIK

QLSQNTYTPREAGSQKDESLAYYIENQFHEFKFSKVWRDEHYVKIQVKS

SIGQNMVTIVQSNGNLDPVESPEGYVAFSKPTEVSGKLVHANFGTKKDF

EELSYSVNGSLVIVRAGEITFAEKVANAQSFNAIGVLIYMDKNKFPVVE

ADLALFGHAHLGTGDPYTPGFPSFNHTQFPPSQSSGLPNIPVQTISRAA

AEKLFGKMEGSCPARWNIDSSCKLELSQNQNVKLIVKNVLKERRILNIF

GVIKGYEEPDRYVVVGAQRDALGAGVAAKSSVGTGLLLKLAQVFSDMIS

KDGFRPSRSIIFASWTAGDFGAVGATEWLEGYLSSLHLKAFTYINLDKV

VLGTSNFKVSASPLLYTLMGKIMQDVKHPVDGKSLYRDSNWISKVEKLS

FDNAAYPFLAYSGIPAVSFCFCEDADYPYLGTRLDTYEALTQKVPQLNQ

MVRTAAEVAGQLIIKLTHDVELNLDYEMYNSKLLSFMKDLNQFKTDIRD

MGLSLQWLYSARGDYFRATSRLTTDFHNAEKTNRFVMREINDRIMKVEY

HFLSPYVSPRESPFRHIFWGSGSHTLSALVENLKLRQKNITAFNETLFR

NQLALATWTIQGVANALSGDIWNIDNEF

In some embodiments, an anti-transferrin receptor antibody binds to an amino acid segment of the receptor as follows:
FVKIQVKDSAQNSVIIVDKNGRLVYLVENPGGYVAY-SKAATVTGKLVHANFGTKKDFE DLYTPVNGSIV-IVRAGKITFAEKVANAESLNAIGVLIYMDQTKFPIV-NAELSFFGHAHLG TGDPYTPGFPSFNHTQFPPSR-SSGLPNIPVQTISRAAAEKLFGNMEGDCPSDWKTD-STCR MVTSESKNVKLTVSNVLKE (SEQ ID NO: 5) and does not inhibit the binding interactions between transferrin receptors and transferrin and/or human hemochromatosis protein (also known as HFE).

Appropriate methodologies may be used to obtain and/or produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988).

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway. e.g. a glycosyltransferase. In some embodiments, an antibody is functionalized with sugar or carbohydrate molecules as described in International Patent Application Publication WO2014065661, published on May 1, 2014, entitled, *"Modified antibody, antibody-conjugate and process for the preparation thereof"*.

Some aspects of the disclosure provide proteins that bind to transferrin receptor (e.g., an extracellular portion of the transferrin receptor). In some embodiments, transferrin receptor antibodies provided herein bind specifically to transferrin receptor (e.g., human transferrin receptor). Transferrin receptors are internalizing cell surface receptors that transport transferrin across the cellular membrane and participate in the regulation and homeostasis of intracellular iron levels. In some embodiments, transferrin receptor antibodies provided herein bind specifically to transferrin receptor from human, non-human primates, mouse, rat, etc. In some embodiments, transferrin receptor antibodies provided herein bind to human transferrin receptor. In some embodiments, transferrin receptor antibodies provided herein specifically bind to human transferrin receptor. In some embodiments, transferrin receptor antibodies provided herein bind to an apical domain of human transferrin receptor. In some embodiments, transferrin receptor antibodies provided herein specifically bind to an apical domain of human transferrin receptor.

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 1. In some embodiments, transferrin receptor antibodies include the CDR-H1, CDR-H2, and CDR-H3 as provided for any one of the anti-transferrin receptor antibodies selected from Table 1. In some embodiments, anti-transferrin receptor antibodies include the CDR-L1, CDR-L2, and CDR-L3 as provided for any one of the anti-transferrin receptor antibodies selected from Table 1. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 1. The disclosure also includes any nucleic acid sequence that encodes a molecule comprising a CDR-H1, CDR-H2, CDR-H3, CDR-L1. CDR-L2, or CDR-L3 as provided for any one of the anti-transferrin receptor antibodies selected from Table 1. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or light chain CDR3s of any one of the anti-transferrin receptor antibodies selected from Table 1.

In some examples, any of the anti-transferrin receptor antibodies of the disclosure have one or more CDR (e.g., CDR-H or CDR-L) sequences substantially similar to any of the CDR-H1, CDR-H2, CDR-H3, CDR-L1, CDR-L2, and/ or CDR-L3 sequences from one of the anti-transferrin receptor antibodies selected from Table 1. In some embodiments, the position of one or more CDRs along the VH (e.g., CDR-H1, CDR-H2, or CDR-H3) and/or VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or CDR-H3 described herein may be one, two, three, four, five or more amino acids shorter than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or CDR-H3 described herein may be one, two, three, four, five or more amino acids longer than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 1. For example, the antibodies may include one or more CDR sequence(s) from any of the anti-transferrin receptor antibodies selected from Table 1 containing up to 5, 4, 3, 2, or 1 amino acid residue variations as compared to the corresponding CDR region in any one of the CDRs provided herein (e.g., CDRs from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 1. In some embodiments, any of the VL domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 1.

In some embodiments, anti-transferrin receptor antibodies of the disclosure include any antibody that includes a heavy chain variable domain and/or a light chain variable domain of any anti-transferrin receptor antibody, such as any one of the anti-transferrin receptor antibodies selected from Table 1. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 1.

Aspects of the disclosure provide anti-transferrin receptor antibodies having a heavy chain variable (VH) and/or a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 1. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 1.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 1. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 1. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 1. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 1. In some embodiments, the light chain variable framework region that is derived from said amino acid sequence consists of said amino acid sequence but for the presence of up to 10 amino acid substitutions, deletions, and/or insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 1. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99/%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 1. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 1. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 1.

In some embodiments, the anti-transferrin receptor antibody is any anti-transferrin receptor antibody, such as any one of the anti-transferrin receptor antibodies selected from Table 1.

In some embodiments, an anti-transferrin receptor antibody comprises a VL domain comprising the amino acid sequence of any anti-transferrin receptor antibody, such as any one of the anti-transferrin receptor antibodies selected from Table 1, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, the muscle-targeting agent is a transferrin receptor antibody (e.g., antibody and variants thereof as described in International Application Publication WO 2016/081643, incorporated herein by reference).

In some embodiments, the heavy chain and light chain CDRs of an example antibody according to different definition systems are provided in Table 1.1. The different definition systems, e.g., the Kabat definition, the Chothia definition, and/or the contact definition have been described. See, e.g., (e.g., Kabat, E. A., et al. (1991) Sequences of Proteins of Immunological Interest, Fifth Edition. U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) 1. Molec. Biol. 273:927-948; and Almagro, J. Mol. Recognit. 17:132-143 (2004). See also hgmp.mrc.ac.uk and bioinf.org.uk/abs).

Example heavy chain variable domain (VH) and light chain variable domain sequences are also provided.

VH (SEQ ID NO: 283)
QVQLQQPGAELVKPGASVKLSCKASGYTFTSYWMHWVKQRPGQGLEWIG
EINPTNGRTNYIEKFKSKATLTVDKSSSTAYMQLSSLTSEDSAVYYCAR
GTRAYHYWGQGTSVTVSS

VL (SEQ ID NO: 284)
DIQMTQSPASLSVSVGETVTITCRASDNLYSNLAWYQQKQGKSPQLLVY
DATNLADGVPSRFSGSGSGTQYSLKINSLQSEDFGTYYCQHFWGTPLTF
GAGTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 1.1. Alternatively or in addition, the transferrin receptor antibody of the present disclosure comprises a CDR-L1, a CDR-L2, and a CDR-L3 that are the same as the CDR-L1, CDR-L2, and CDR-L3 shown in Table 1.1.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 1.1. "Collectively" means that the total number of amino acid variations in all of the three heavy chain CDRs is within the defined range. Alternatively or in addition, the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 1.1.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 1.1. Alternatively or in addition, the transferrin receptor antibody of the present disclosure may comprise CDR-L1, a CDR-L2, and a CDR-L3, at least one of which contains no more than 3 amino acid

TABLE 1

Heavy chain and light chain CDRs of the mouse transferrin receptor antibody

| CDRs | Kabat | Chothia | Contact |
|---|---|---|---|
| CDR-H1 | SYWMH (SEQ ID NO: 267) | GYTFTSY (SEQ ID NO: 273) | TSYWMH (SEQ ID NO: 275) |
| CDR-H2 | EINPTNGRTNYIEKFKS (SEQ ID NO: 268) | NPTNGR (SEQ ID NO: 274) | WIGEINPTNGRTN (SEQ ID NO: 276) |
| CDR-H3 | GTRAYHY (SEQ ID NO: 269) | GTRAYHY (SEQ ID NO: 269) | ARGTRA (SEQ ID NO: 277) |
| CDR-L1 | RASDNLYSNLA (SEQ ID NO: 270) | RASDNLYSNLA (SEQ ID NO: 270) | YSNLAWY (SEQ ID NO: 278) |
| CDR-L2 | DATNLAD (SEQ ID NO: 271) | DATNLAD (SEQ ID NO: 271) | LLVYDATNLA (SEQ ID NO: 279) |
| CDR-L3 | QHFWGTPLT (SEQ ID NO: 272) | QHFWGTPLT (SEQ ID NO: 272) | QHFWGTPL (SEQ ID NO: 280) | variations (e.g., no more than 3, 2, or 1 amino acid variation) as compared with the counterpart light chain CDR as shown in Table 1.1.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 1.1. In some embodiments, the transferrin receptor antibody of the present disclosure comprises a CDR-L3 containing one amino acid variation as compared with the CDR-L3 as shown in Table 1.1. In some embodiments, the transferrin receptor antibody of the present disclosure comprises a CDR-L3 of QHFAGTPLT (SEQ ID NO: 281 according to the Kabat and Chothia definition system) or QHFAGTPL (SEQ ID NO: 282 according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 1.1, and comprises a CDR-L3 of QHFAGTPLT (SEQ ID NO: 281 according to the Kabat and Chothia definition system) or QHFAGTPL (SEQ ID NO: 282 according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 1.1. Alternatively or in addition, the transferrin receptor antibody of the present disclosure comprises light chain CDRs that collectively are at least 80% (e.g., 80%, 85%, 90%, 95%, or 98%) identical to the light chain CDRs as shown in Table 1.1.

In some embodiments, the transferrin receptor antibody of the present disclosure comprises a VH comprising the amino acid sequence of SEQ ID NO: 283. Alternatively or in addition, the transferrin receptor antibody of the present disclosure comprises a VL comprising the amino acid sequence of SEQ ID NO: 284.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 283. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 284.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 283. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 284.

In some embodiments, the transferrin receptor antibody of the present disclosure is a humanized antibody (e.g., a humanized variant). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1. CDR-H2, and CDR-H3 shown in Table 1.1, and comprises a humanized heavy chain variable region and/or a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 1.1) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 284, and/or one or more amino acid substitutions at positions 1, 5, 7, 11, 12, 20, 38, 40, 44, 66, 75, 81, 83, 87, and 108 as compared with the VH as set forth in SEQ ID NO: 283. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 284, and/or amino acid substitutions at all of positions 1, 5, 7, 11, 12, 20, 38, 40, 44, 66, 75, 81, 83, 87, and 108 as compared with the VH as set forth in SEQ ID NO: 283.

In some embodiments, the transferrin receptor antibody of the present disclosure is a humanized antibody and contains residues at positions 43 and 48 of the VL as set forth in SEQ ID NO: 284. Alternatively or in addition, the transferrin receptor antibody of the present disclosure is a humanized antibody and contains the residues at positions 48, 67, 69, 71, and 73 of the VH as set forth in SEQ ID NO: 283.

The VH and VL amino acid sequences of an example humanized antibody that may be used in accordance with the present disclosure are provided:

```
Humanized VH
                                       (SEQ ID NO: 285)
EVQLVQSGAEVKKPGASVKVSCKASGYTFTSYWMHWVRQAPGQRLEWIG
EINPTNGRTNYIEKFKSRATLTVDKSASTAYMELSSLRSEDTAVYYCAR
GTRAYHYWGQGTMVTVSS Humanized VL
                                       (SEQ ID NO: 286)
DIQMTQSPSSLSASVGDRVTITCRASDNLYSNLAWYQQKPGKSPKLLVY
DATNLADGVPSRFSGSGSGTDYSLKINSLQSEDFGTYYCQHFWGTPLTF
GAGTKLELK
```

In some embodiments, the transferrin receptor antibody of the present disclosure comprises a VH comprising the amino acid sequence of SEQ ID NO: 285. Alternatively or in addition, the transferrin receptor antibody of the present disclosure comprises a VL comprising the amino acid sequence of SEQ ID NO: 286.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 285. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 286.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 285. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 286.

In some embodiments, the transferrin receptor antibody of the present disclosure is a humanized variant comprising amino acid substitutions at one or more of positions 43 and 48 as compared with the VL as set forth in SEQ ID NO: 284, and/or amino acid substitutions at one or more of positions 48, 67, 69, 71, and 73 as compared with the VH as set forth in SEQ ID NO: 283. In some embodiments, the transferrin receptor antibody of the present disclosure is a humanized variant comprising a S43A and/or a V48L mutation as compared with the VL as set forth in SEQ ID NO: 284, and/or one or more of A67V, L69I, V71R, and K73T mutations as compared with the VH as set forth in SEQ ID NO: 283.

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 284, and/or amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 283.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the heavy chain of any of the transferrin receptor antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain). e.g., IgG1, IgG2, or IgG4. An exemplary human IgG1 constant region is given below:

```
                                     (SEQ ID NO: 287)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK
```

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

```
                                     (SEQ ID NO: 288)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCP
```

Other antibody heavy and light chain constant regions are well known in the art, e.g., those provided in the IMGT database (www.imgt.org) or at www.vbase2.org/vbstat.php., both of which are incorporated by reference herein.

Exemplary heavy chain and light chain amino acid sequences of the transferrin receptor antibodies described are provided below:

```
Heavy Chain (VH + human IgG1 constant region)
                                     (SEQ ID NO: 289)
QVQLQQPGAELVKPGASVKLSCKASGYTFTSYWMHWVKQRPGQGLEWIG

EINPTNGRTNYIEKFKSKATLTVDKSSSTAYMQLSSLTSEDSAVYYCAR

GTRAYHYWGQGTSVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKENWYVDGVEVHNAKTKPREEQ
```

```
YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK

Light Chain (VL + kappa light chain)
                                          (SEQ ID NO: 290)
QVQLQQPGAELVKPGASVKLSCKASGYTFTSYWMHWVKQRPGQGLEWIG

EINPTNGRTNYIEKFKSKATLTVDKSSSTAYMQLSSLTSEDSAVYYCAR

GTRAYHYWGQGTSVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCP

Heavy Chain (humanized VH + human IgG1 constant
region)
                                          (SEQ ID NO: 291)
EVQLVQSGAEVKKPGASVKVSCKASGYTFTSYWMHWVRQAPGQRLEWIG

EINPTNGRTNYIEKFKSRATLTVDKSASTAYMELSSLRSEDTAVYYCAR

GTRAYHYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK

Light Chain (humanized VL + kappa light chain)
                                          (SEQ ID NO: 292)
DIQMTQSPSSLSASVGDRVTITCRASDNLYSNLAWYQQKPGKSPKLLVY

DATNLADGVPSRFSGSGSGTDYSLKINSLQSEDFGTYYCQHFWGTPLTF

GAGTKLELKASTKGPSVFPLAPSSKSTSGGTAALGCLVKDYFPEPVTVS

WNSGALTSGVHTFPAVLQSSGLYSLSSVVTVPSSSLGTQTYICNVNHKP

SNTKVDKKVEPKSCDKTHTCP
```

In some embodiments, the transferrin receptor antibody described herein comprises a heavy chain comprising an amino acid sequence that is at least 80% (e.g., 80%, 85%, 90%, 95%, or 98%) identical to SEQ ID NO: 289. Alternatively or in addition, the transferrin receptor antibody described herein comprises a light chain comprising an amino acid sequence that is at least 80% (e.g., 80%, 85%, 90%, 95%, or 98%) identical to SEQ ID NO: 290. In some embodiments, the transferrin receptor antibody described herein comprises a heavy chain comprising the amino acid sequence of SEQ ID NO: 289. Alternatively or in addition, the transferrin receptor antibody described herein comprises a light chain comprising the amino acid sequence of SEQ ID NO: 290.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 289. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 290.

In some embodiments, the transferrin receptor antibody described herein comprises a heavy chain comprising an amino acid sequence that is at least 80% (e.g., 80%, 85%, 90%, 95%, or 98%) identical to SEQ ID NO: 291. Alternatively or in addition, the transferrin receptor antibody described herein comprises a light chain comprising an amino acid sequence that is at least 80% (e.g., 80%, 85%, 90%, 95%, or 98%) identical to SEQ ID NO: 292. In some embodiments, the transferrin receptor antibody described herein comprises a heavy chain comprising the amino acid sequence of SEQ ID NO: 291. Alternatively or in addition, the transferrin receptor antibody described herein comprises a light chain comprising the amino acid sequence of SEQ ID NO: 292.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain of a humanized antibody as set forth in SEQ ID NO: 289. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of humanized antibody as set forth in SEQ ID NO: 290.

In some embodiments, the transferrin receptor antibody is an antigen binding fragment (FAB) of an intact antibody (full-length antibody). Antigen binding fragment of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Exemplary FABs amino acid sequences of the transferrin receptor antibodies described herein are provided below:

```
Heavy Chain FAB (VH + a portion of human IgG1
constant region)
                                          (SEQ ID NO: 293)
QVQLQQPGAELVKPGASVKLSCKASGYTFTSYWMHWVKQRPGQGLEWIG

EINPTNGRTNYIEKFKSKATLTVDKSSSTAYMQLSSLTSEDSAVYYCAR

GTRAYHYWGQGTSVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCP

Heavy Chain FAB (humanized VH + a portion of
human IgG1 constant region)
                                          (SEQ ID NO: 294)
EVQLVQSGAEVKKPGASVKVSCKASGYTFTSYWMHWVRQAPGQRLEWIG

EINPTNGRTNYIEKFKSRATLTVDKSASTAYMELSSLRSEDTAVYYCAR

GTRAYHYWGQGTMVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCP
```

The transferrin receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 289).

b. Other Muscle-Targeting Antibodies

In some embodiments, the muscle-targeting antibody is an antibody that specifically binds hemojuvelin, caveolin-3, Duchenne muscular dystrophy peptide, myosin IIb, or CD63. In some embodiments, the muscle-targeting antibody is an antibody that specifically binds a myogenic precursor protein. Exemplary myogenic precursor proteins include, without limitation, ABCG2. M-Cadherin/Cadherin-15, Caveolin-1, CD34, FoxK1. Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan. FABP3/H-FABP, GDF-8/Myostatin, GDF-11/GDF-8, integrin alpha 7, Integrin alpha 7 beta 1, Integrin beta 1/CD29, MCAM/CD146, MyoD. Myogenin, Myosin Light Chain Kinase Inhibitors, NCAM-1/CD56, and Troponin I. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g. amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g. amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g. the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919: WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919: WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) *J Biol Chem* 276: 6591-604).

In some embodiments, one or more amino in the constant region of a muscle-targeting antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcγ receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" *Biochim Biophys Acta* 2008, 1786: 126-38; Jarver P., et al., "In vivo biodistribution and efficacy of peptide mediated delivery" *Trends Pharmacol Sci* 2010; 31: 528-35; Samoylova T. I., et al., "Elucidation of muscle-binding peptides by phage display screening" *Muscle Nerve* 1999; 22: 460-6; U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." *Biomol Eng* 2002; 18: 269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 August 18:11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 6) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 6). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." *Int J Pharm* 2002; 231: 177-84; the entire contents of which are hereby incorporated by reference. Here, a 12 amino acid peptide having the sequence SKTFNTHPQSTP (SEQ ID NO: 7) was identified and this muscle-targeting peptide showed improved binding to C2C12 cells relative to the ASSLNIA (SEQ ID NO: 6) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" *J Virol* 2005; 79: 13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEH-KEEELI (SEQ ID NO: 8) appeared most frequently. Accordingly, in some embodiments, the muscle-targeting agent comprises the amino acid sequence TARGEHKEEELI (SEQ ID NO: 8).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081; Samoylova, T. I. and Smith, B. F. "Elucidation of muscle-binding peptides by phage display screening." Muscle Nerve, 1999, 22:4. 460-6). In some embodiments, a muscle-targeting peptide has been previously disclosed (see, e.g. Writer M. J. et al. "Targeted gene delivery to human airway epithelial cells with synthetic vectors incorporating novel targeting peptides selected by phage display." J. Drug Targeting. 2004; 12:185; Cai, D. "BDNF-mediated enhancement of inflammation and injury in the aging heart." Physiol Genomics. 2006, 24:3, 191-7; Zhang, L. "Molecular profiling of heart endothelial cells." Circulation, 2005, 112:11, 1601-11; McGuire. M. J. et al. "In vitro selection of a peptide with high selectivity for cardiomyocytes in vivo." J Mol Biol. 2004, 342:1, 171-82). Exemplary muscle-targeting peptides comprise an amino acid sequence of the following group: CQAQGQLVC (SEQ ID NO: 9), CSERSMNFC (SEQ ID NO: 10), CPKTRRVPC (SEQ ID NO: 11), WLSEAGPVVTVRALRGTGSW (SEQ ID NO: 12), ASSLNIA (SEQ ID NO: 6). CMQHSMRVC (SEQ ID NO: 13), and DDTRHWG (SEQ ID NO: 14). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include R-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic. e.g. bicyclic (see, e.g. Silvana, M. G. et al. Mol. Therapy, 2018, 26:1, 132-147).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed. These aptamers may be conceived of, produced, synthesized, and/or derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20; Germer, K. et al. "RNA aptamers and their therapeutic and diagnostic applications." int. J. Biochem. Mol. Biol. 2013; 4: 27-40). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214; Thiel, W. H. et al. "Smooth Muscle Cell-targeted RNA Aptamer Inhibits Neointimal Formation." Mol Ther. 2016, 24:4, 779-87). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about 10-15 kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4). GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FLJ46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and clofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or lack a C-terminal anchoring domain. In some embodiments, hemojuvelin may be annotated under GenBank RefSeq Accession Numbers NM_001316767.1, NM_145277.4, NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the splicing and processing of a RNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a mutated DMD allele. Exemplary molecular payloads are described in further detail herein, however, it should be appreciated that the exemplary molecular payloads provided herein are not meant to be limiting.

i. Oligonucleotides

Any suitable oligonucleotide may be used as a molecular payload, as described herein. In some embodiments, the oligonucleotide may be designed to induce exon skipping, e.g., EXONDYS 51 oligonucleotide (Sarepta Therapeutics, Inc.), which comprises SEQ ID NO: 195 (CUCCAACAU-CAAGGAAGAUGGCAUUUCUAG); WVE-210201 (Wave Life Sciences), which comprises SEQ ID NO: 186 (UCAAGGAAGAUGGCAUUUCU); Casimersen (Sarepta Therapeutics, Inc.), which comprises SEQ ID NO: 159 (CAAUGCCAUCCUGGAGUUCCUG); or Golodirsen (Sarepta Therapeutics, Inc.), which comprises SEQ ID NO: 231 (GUUGCCUCCGGUUCUGAAGGUGUUC).

In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to cause degradation and block translation of an mRNA. In some embodiments, the oligonucleotide may be designed to promote stability of an mRNA. In some embodiments, the oligonucleotide may be designed to promote translation of an mRNA. In some embodiments, an oligonucleotide may be designed to promote stability and promote translation of an mRNA. In some embodiments, an oligonucleotide may be a guide nucleic acid (e.g., guide RNA) for directing activity of an enzyme (e.g., a gene editing enzyme). In some embodiments, a guide nucleic acid may direct an enzyme to delete the entirety or a part of a mutated DMD allele (e.g., to facilitate in-frame exon skipping). In some embodiments, the oligonucleotide may be designed to target repressive regulators of DMD expression, e.g., miR-31. Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Examples of oligonucleotides useful for targeting DMD are provided in U.S. Patent Application Publication US20100130591A1, published on May 27, 2010, entitled "MULTIPLE EXON SKIPPING COMPOSITIONS FOR DMD"; U.S. Pat. No. 8,361,979, issued Jan. 29, 2013, entitled "MEANS AND METHOD FOR INDUCING EXON-SKIPPING"; U.S. Patent Application Publication 20120059042, published Mar. 8, 2012, entitled "METHOD FOR EFFICIENT EXON (44) SKIPPING IN DUCHENNE MUSCULAR DYSTROPHY AND ASSOCIATED MEANS; U.S. Patent Application Publication 20140329881, published Nov. 6, 2014, entitled "EXON SKIPPING COMPOSITIONS FOR TREATING MUSCULAR DYSTROPHY"; U.S. Pat. No. 8,232,384, issued Jul. 31, 2012, entitled "ANTISENSE OLIGONUCLEOTIDES FOR INDUCING EXON SKIPPING AND METHODS OF USE THEREOF"; U.S. Patent Application Publication 20120022134A1, published Jan. 26, 2012, entitled "METHODS AND MEANS FOR EFFICIENT SKIPPING OF EXON 45 IN DUCHENNE MUSCULAR DYSTROPHY PRE-MRNA; U.S. Patent Application Publication 20120077860, published Mar. 29, 2012, entitled "ADENO-ASSOCIATED VIRAL VECTOR FOR EXON SKIPPING IN A GENE ENCODING A DISPENSABLE DOMAN PROTEIN"; U.S. Pat. No. 8,324,371, issued Dec. 4, 2012, entitled "OLIGOMERS"; U.S. Pat. No. 9,078,911, issued Jul. 14, 2015, entitled "ANTISENSE OLIGONUCLEOTIDES", U.S. Pat. No. 9,079,934, issued Jul. 14, 2015, entitled "ANTI SENSE NUCLEIC ACIDS"; U.S. Pat. No. 9,034,838, issued May 19, 2015, entitled "MIR-31 IN DUCHENNE MUSCULAR DYSTROPHY THERAPY"; and International Patent Publication WO2017062862A3, published Apr. 13, 2017, entitled "OLIGONUCLEOTIDE COMPOSITIONS AND METHODS THEREOF", the contents of each of which are incorporated herein in their entireties.

Table 2 provides non-limiting examples of sequences of oligonucleotide that are useful for targeting DMD, e.g., for exon skipping. In some embodiments, an oligonucleotide may comprise any sequence provided in Table 2.

TABLE 2

Oligonucleotide sequences for targeting DMD.

| EXON | SEQ ID NO: | SEQUENCE |
|---|---|---|
| 8 | 15 | CUUCCUGGAUGGCUUCAAU |
| 8 | 16 | GUACAUUAAGAUGGACUUC |
| 8 | 17 | UAUCUGGAUAGGUGGUAUCAAGAUCUGUAA |
| 8 | 18 | AUGUAACUGAAAAUGUUCUUCUUUA |
| 8 | 19 | UGGAUAGGUGGUAUCAACAUCUGUAAGCAC |
| 8 | 20 | GAUAGGUGGUAUCAACAUCUGU |
| 8 | 21 | UAUCUGGAUAGGUGGUAUCAACAUCUGUAA |
| 8 | 22 | AAACUUGGAAGAGUGAUGUGAUGUA |
| 8 | 23 | GCUCACUUGUUGAGGCAAAACUUGGAA |
| 8 | 24 | GCCUUGGCAACAUUUCCACUUCCUG |
| 8 | 25 | UACACACUUUACCUGUUGAGAAUAG |
| 8 | 26 | GAUAGGUGGUAUCAACAUCUGUAA |
| 8 | 27 | GAUAGGUGGUAUCAACAUCUG |
| 8 | 28 | GAUAGGUGGUAUCAACAUCUGUAAG |
| 8 | 29 | GGUGGUAUCAACAUCUGUAA |
| 8 | 30 | GUAUCAACAUCUGUAAGCAC |
| 23 | 31 | CGGCUAAUUUCAGAGGGCGCUUUCUUNGAC |
| 23 | 32 | ACAGUGGUGCUGAGAUAGUAUAGGCC |
| 23 | 33 | UAGGCCACUUUGUUGCUCUUGC |
| 23 | 34 | UUCAGAGGGCGCUUUCUUC |
| 23 | 253 | GGCCAAACCUCGGCUUACCUGAAAU |
| 23 | 254 | GGCCAAACCUCGGCUUACCU |
| 35 | 35 | UCUUCAGGUGCACCUUCUGUUUCUCAAUCU |
| 35 | 36 | UCUGUGAUACUCUUCAGGUGCACCUUCUGU |
| 35 | 37 | UCUUCUGCUCGGGAGGUGACA |
| 35 | 38 | CCAGUUACUAUUCAGAAGAC |
| 35 | 39 | UCUUCAGGUGCACCUUCUGU |
| 43 | 40 | UGCUGCUGUCUUCUUGCU |
| 43 | 41 | UUGUUAACUUUUUCCCAUU |
| 43 | 42 | UGUUAACUUUUUCCCAUUGG |
| 43 | 43 | CAUUUUGUUAACUUUUUCCC |
| 43 | 44 | CUGUAGCUUCACCCUUUCC |
| 43 | 45 | GAGAGCUUCCUGUAGCUUCACCCUUU |
| 43 | 46 | UCCUGUAGCUUCACCCUUUCCACAGGCG |
| 43 | 47 | UGUGUUACCUACCCUUGUCG |
| 43 | 48 | UAGACUAUCUUUUAUAUUCUGUAAUAU |
| 43 | 49 | GAGAGCUUCCUGUAGCUUCACCCUUUCCA |
| 43 | 50 | UUCCUGUAGCUUCACCCUUUCCACAGGCGUU |
| 43 | 51 | AGCUUCCUGUAGCUUCACCCUUU |
| 43 | 52 | GGAGAGCUUCCUGUAGCUUCACCCUUU |

TABLE 2-continued

Oligonucleotide sequences for targeting DMD.

| EXON | SEQ ID NO: | SEQUENCE |
|---|---|---|
| 43 | 53 | GAGAGCUUCCUGUAGCUUCACCC |
| 43 | 54 | UAUGUGUUACCUACCCUUGUCGGUC |
| 43 | 55 | GGAGAGAGCUUCCUGUAGCU |
| 43 | 56 | UCACCCUUUCCACAGGCGUUGCA |
| 43 | 57 | GCUGGGAGAGAGCUUCCUGUAGCUUCAC |
| 43 | 58 | UGUUACCUACCCUUGUCGGUCCUUGUAC |
| 43 | 59 | CUGCUGUCUUCUUGCUAUGAAUAAUGUC |
| 43 | 60 | GGCGUUGCACUUUGCAAUGCUGCUGUCU |
| 43 | 61 | UUGGAAAUCAAGCUGGGAGAGAGCUUCC |
| 43 | 62 | CUACCCUUGUCGGUCCUUGUACAUUUUG |
| 43 | 63 | GUCAAUCCGACCUGAGCUUUGUUGUAGA |
| 43 | 64 | CUUGCUAUGAAUAAUGUCAAUCCGACC |
| 43 | 65 | UAUAUGUGUUACCUACCCUUGUCGGUCC |
| 43 | 255 | AAUCAGCUGGGAGAGAGCUUCCUGUAGCU |
| 43 | 256 | UCGUUCUUCUGUCGUCGUAACGUUUC |
| 44 | 66 | UUUGUGUCUUUCUGAGAAAC |
| 44 | 67 | AAAGACUUACCUUAAGAUAC |
| 44 | 68 | AUCUGUCAAAUCGCCUGCAG |
| 44 | 69 | CGCCGCCAUUUCUCAACAG |
| 44 | 70 | UUUGUAUUUAGCAUGUUCCC |
| 44 | 71 | CCGCCAUUUCUCAACAG |
| 44 | 72 | UUCUCAGGAAUUUGUGUCUUU |
| 44 | 73 | GACAACUCUUU |
| 44 | 74 | UCAGCUUCUGUUAGCCACUG |
| 44 | 75 | UGUUCAGCUUCUGUUAGCCACUGA |
| 44 | 76 | CUGUUCAGCUUCUGUUAGCCACUGAUU |
| 44 | 77 | UUCUCAACAGAUCUGUCAAAUCGCCUGCAG |
| 44 | 78 | GCCACUGAUUAAAUAUCUUUAUAUC |
| 44 | 79 | UCUGUUAGCCACUGAUUAAAUAUCUUUAUA |
| 44 | 80 | GAGAAACUGUUCAGCUUCUGUUAGCCACUGA |
| 44 | 81 | UCUUUCUGAGAAACUGUUCAGCUUCUGUUAG |
| 44 | 82 | CAGAUCUGUCAAAUCGCCUGCAGGUA |
| 44 | 83 | CAACAGAUCUGUCAAAUCGCCUGCAG |
| 44 | 84 | AAACUGUUCAGCUUCUGUUAGCCACUGAUUAAA |
| 44 | 85 | GAAACUGUUCAGCUUCUGUUAGCCACUGAUU |
| 44 | 86 | AAACUGUUCAGCUUCUGUUAGCCACUGA |
| 44 | 87 | UGAGAAACUGUUCAGCUUCUGUUAGCCA |
| 44 | 88 | UUCUGAGAAACUGUUCAGCUUCUGUUAGCCAC |
| 44 | 89 | UUCUGAGAAACUGUUCAGCUUCUGUU |
| 44 | 90 | GAUCUGUCAAAUCGCCUGCAGGUAA |
| 44 | 91 | AUAAUGAAAACGCCGCCAUUUCUCA |
| 44 | 92 | AAACUGUUCAGCUUCUGUUAGCCAC |
| 44 | 93 | UUGUGUCUUUCUGAGAAACUGUUCA |
| 44 | 94 | CCAAUUCUCAGGAAUUUGUGUCUUU |
| 44 | 95 | AUCGCCUGCAGGUAAAAGCAUAUGG |
| 44 | 96 | UGAAAACGCCGCCAUUUCUCAACAGAUCUG |
| 44 | 97 | CAUAAUGAAAACGCCGCCAUUUCUCAACAG |
| 44 | 98 | UGUUCAGCUUCUGUUAGCCACUGAUUAAAU |
| 44 | 99 | CAGAUCUGUCAAAUCGCCUGCAGG |
| 44 | 100 | CAACAGAUCUGUCAAAUCGCCUGCAGG |
| 44 | 101 | CUCAACAGAUCUGUCAAAUCGCCUGCAGG |
| 44 | 102 | GAUCUGUCAAAUCGCCUGCAGGU |
| 44 | 103 | GAUCUGUCAAAUCGCCUGCAGG |
| 44 | 104 | GAUCUGUCAAAUCGCCUGCAG |
| 44 | 105 | CAGAUCUGUCAAAUCGCCUGCAGGU |
| 44 | 106 | CAGAUCUGUCAAAUCGCCUGCAG |
| 44 | 107 | GUGUCUUUCUGAGAAACUGUUCAGC |
| 44 | 108 | GAGAAACUGUUCAGCUUCUGUUAGCCAC |
| 44 | 109 | GAAACUGUUCAGCUUCUGUUAGCCACUG |
| 44 | 110 | CUGUUCAGCUUCUGUUAGCCACUG |
| 44 | 111 | AUCUGUCAAAUCGCCUGCAGGUAAAAG |
| 44 | 112 | GAUCUGUCAAAUCGCCUGCAGGUAAAAGC |
| 44 | 257 | CACCGAUUGUCUUCGA |
| 44 | 258 | CCCUUGUACGAUUUAUG |
| 44 | 259 | UCUGUGUUUAAGGACUCU |
| 45 | 113 | GCUGAAUUAUUUCUUCCCC |
| 45 | 114 | UUUUUCUGUCUGACAGCUG |
| 45 | 115 | UCUGUUUUUGAGGAUUGC |
| 45 | 116 | CCACCGCAGAUUCAGGC |
| 45 | 117 | GCCCAAUGCCAUCCUGG |
| 45 | 118 | UUUGCAGACCUCCUGCC |
| 45 | 119 | CAGUUUGCCGCUGCCCA |
| 45 | 120 | GUUGCAUUCAAUGUUCUGAC |
| 45 | 121 | AUUUUUCCUGUAGAAUACUGG |

TABLE 2-continued

Oligonucleotide sequences for targeting DMD.

| EXON | SEQ ID NO: | SEQUENCE |
|---|---|---|
| 45 | 122 | GCUGCCCAAUGCGAUCCUGGAGUUCCUGUAAGAU |
| 45 | 123 | GCUGCCCAAUGCCAUCCUGGAGUUCCUG |
| 45 | 124 | GCUGCCCAAUGCCAUCCUGGAGUUCCUGUAA |
| 45 | 125 | CAAUGCCAUCCUGGAGUUCCUGUAAGAUACC |
| 45 | 126 | GCUGCCCAAUGCCAUCCUGGAGUUCCUGUAAG |
| 45 | 127 | CCAAUGCCAUCCUGGAGUUCCUGUAAGAUA |
| 45 | 128 | UUGCCGCUGCCCAAUGCCAUCCUGGAGUUCCUGUAAGAU |
| 45 | 129 | GCUGCCCAAUGCCAUCCUGGAGUUCCUGUAAGAU |
| 45 | 130 | CAAUGCCAUCCUGGAGUUCCUGUAAGA |
| 45 | 131 | CAGUUUGCCGCUGCCCAAUGCCAUCC |
| 45 | 132 | CUUCCCCAGUUGCAUUCAAUGUUC |
| 45 | 133 | CUGGCAUCUGUUUUUGAGGAUUG |
| 45 | 134 | UUAGAUCUGUCGCCCUACCU |
| 45 | 135 | GCUGCCCAAUGCCAUCCUGGAGUUCCUGUAAGAUACCAA |
| 45 | 136 | GCCCAAUGCCAUCCUGGAGUUCCUGUAAGAUACC |
| 45 | 137 | CAUCCUGGAGUUCCUGUAAGAUACC |
| 45 | 138 | UGCCAUCCUGGAGUUCCUGUAAGAUACC |
| 45 | 139 | UGCCAUCCUGGAGUUCCUGUAAGAU |
| 45 | 140 | CAAUGCCAUCCUGGAGUUCCUGUAAGAU |
| 45 | 141 | GCCCAAUGCCAUCCUGGAGUUCCUGUAAGAU |
| 45 | 142 | GCCCAAUGCCAUCCUGGAGUUCCUGUAA |
| 45 | 143 | GCCGCUGCCCAAUGACAUCCUGGAGUUCCUGUAA |
| 45 | 144 | GCCAUCCUGGAGUUCCUGUAAGAUA |
| 45 | 145 | CCAAUGCCAUCCUGGAGUUCCUGUA |
| 45 | 146 | CUGACAACAGUUUGCCGCUGCCCAA |
| 45 | 147 | UUUGAGGAUUGCUGAAUUAUUUCUU |
| 45 | 148 | CAGUUUGCCGCUGCCCAAUGCCAUCCUGGA |
| 45 | 149 | UUGCCGCUGCCCAAUGCCAUCCUGGAGUUC |
| 45 | 150 | UUUGCCGCUGCCCAAUGCCAUCCUG |
| 45 | 151 | CCAAUGCCAUCCUGGAGUUCCU |
| 45 | 152 | CCCAAUGCCAUCCUGGAGUUCCUGUAAGA |
| 45 | 153 | CCGCUGCCCAAUGCCAUCCUGGAGUUCC |
| 45 | 154 | CCCAAUGCCAUCCUGGAGUUCCUGUAAGAU |
| 45 | 155 | CCGCUGCCCAAUGCCAUCCUGGAGUUCCUG |
| 45 | 156 | UGCCCAAUGCCAUCCUGGAGUUCCUGUAAG |
| 45 | 157 | CCCAAUGCCAUCCUGGAGUUCCUGUAAG |
| 45 | 158 | UGCCCAAUGCCAUCCUGGAGUUCCUGUA |
| 45 | 159 | CAAUGCCAUCCUGGAGUUCCUG |
| 45 | 260 | GCCGCUGCCCAAUGCCAUCCUGGAGUUCCUG |
| 45 | 261 | AUUAGAUCUGUCGCCCUACCUCUUUUUUC |
| 45 | 262 | UGUCGCCCUACCUCUUUUUUCUGUCUG |
| 45 | 263 | GCCCAAUGCCAUCCUGGAGUUCCUG |
| 55 | 160 | AGCCUCUCGCUCACUCACCCUGCAAAGGA |
| 50 | 161 | CCACUCAGAGCUCAGAUCUUCUAACUUCC |
| 50 | 162 | CUUCCACUCAGAGCUCAGAUCUUCUAA |
| 50 | 163 | GGGAUCCAGUAUACUUACAGGCUCC |
| 50 | 164 | CUCAGAGCUCAGAUCUU |
| 50 | 165 | GGCUGCUUUGCCCUC |
| 50 | 166 | CUCAGAUCUUCUAACUUCCUCUUUAAC |
| 50 | 167 | CUCAGAGCUCAGAUCUUCUAACUUCCUCU |
| 50 | 168 | CGCCUUCCACUCAGAGCUCAGAUCUUC |
| 50 | 169 | UCAGCUCUUGAAGUAAACGGUUUACCG |
| 50 | 170 | UUUGCCCUCAGCUCUUGAAGUAAACGG |
| 50 | 171 | GGCUGCUUUGCCCUCAGCUCUUGAAGU |
| 50 | 172 | CAGGAGCUAGGUCAGGCUGCUUUGCC |
| 50 | 173 | UCCAAUAGUGGUCAGUCCAGGAGCU |
| 50 | 174 | AAAGAGAAUGGGAUCCAGUAUACUUAC |
| 50 | 175 | AAAUAGCUAGAGCCAAAGAGAAUGGGA |
| 50 | 176 | GGCUGCUUUGCCCUCAGCUCUUGAAGUAAACGG |
| 50 | 177 | AGGCUGCUUUGCCCUCAGCUCUUGAAGUAA |
| 50 | 178 | GUCAGGCUGCUUUGCCCUCAGCUCUUGAAG |
| 50 | 179 | AGGUCAGGCUGCUUUGCCCUCAGCUCUUGA |
| 50 | 180 | CAGAGCUCAGAUCUUCUAACUUCCU |
| 50 | 181 | CUUACAGGCUCCAAUAGUGGUCAGU |
| 50 | 182 | AUGGGAUCCAGUAUACUUACAGGCU |
| 50 | 183 | AGAGAAUGGGAUCCAGUAUACUUAC |
| 50 | 184 | AACUUCCUCUUUAACAGAAAAGCAUAC |
| 50 | 264 | GAGCUCUCGCUCACUCACCCUGCAAAGGA |
| 51 | 185 | CUCAUACCUUCUGCUUGAUGAUC |
| 51 | 186 | UCAAGGAAGAUGGCAUUUCU |
| 51 | 187 | GAAAGCCAGUCGGUAAGUUC |

TABLE 2-continued

Oligonucleotide sequences for targeting DMD.

| EXON | SEQ ID NO: | SEQUENCE |
|---|---|---|
| 51 | 188 | CACCCACCAUCACCC |
| 51 | 189 | CCUCUGUGAUUUUAUAACUUGAU |
| 51 | 190 | UGAUAUCCUCAAGGUCACCC |
| 51 | 191 | GGUACCUCCAACAUCAAGGAAGAUGGCAUU |
| 51 | 192 | AUUUCUAGUUUGGAGAUGGCAGUUUC |
| 51 | 193 | CAUCAAGGAAGAUGGCAUUUCUAGUU |
| 51 | 194 | GAGCAGGUACCUCCAACAUCAAGGAA |
| 51 | 195 | CUCCAACAUCAAGGAAGAUGGCAUUUCUAG |
| 51 | 196 | ACCAGAGUAACAGUCUGAGUAGGAG |
| 51 | 197 | CACCAGAGUAACAGUCUGAGUAGGA |
| 51 | 198 | UCACCAGAGUAACAGUCUGAGUAGG |
| 51 | 199 | GUCACCAGAGUAACAGUCUGAGUAG |
| 51 | 200 | ACCAGAGUAACAGUCUGAGUAGGAGC |
| 51 | 201 | UUCUGUCCAAGCCCGGUUGAAAUC |
| 51 | 202 | ACAUCAAGGAAGAUGGCAUUUCUAGUUUGG |
| 51 | 203 | ACAUCAAGGAAGAUGGCAUUUCUAG |
| 51 | 204 | AUCAUUUUUUCUCAUACCUUCUGCU |
| 51 | 205 | CACCCACCAUCACCCUCUGUG |
| 51 | 206 | AUCAUCUCGUUGAUAUCCUCAA |
| 51 | 207 | CUCCAACAUCAAGGAAGAUGGCAUUUCU |
| 51 | 208 | CAUCAAGGAAGAUGGCAUUUCUAGU |
| 51 | 265 | AUCAUUUUUUCUCAUACCUUCUGCUAGGAGCUAAAA |
| 52 | 209 | UUGCUGGUCUUGUUUUUC |
| 52 | 210 | CCGUAAUGAUUGUUCU |
| 52 | 211 | GCUGGUCUUGUUUUUCAA |
| 52 | 212 | UGGUCUUGUUUUUCAAAUUU |
| 52 | 213 | GUCUUGUUUUUCAAAUUUUG |
| 52 | 214 | CUUGUUUUUCAAAUUUGGG |
| 52 | 215 | UGUUUUUCAAAUUUGGGC |
| 52 | 216 | UCCAACUGGGGACGCCUCUGUUCCAAAUCCUGC |
| 52 | 217 | UCCUGCAUUGUUGCCUGUAAG |
| 52 | 218 | UCCAACUGGGGACGCCUCUGUUCCAAAUCC |
| 52 | 219 | ACUGGGGACGCCUCUGUUCCA |
| 52 | 220 | CCGUAAUGAUUGUUCUAGCC |
| 52 | 221 | UGUUAAAAACUUACUUCGA |
| 53 | 222 | CUGUUGCCUCCGGUUCUG |
| 53 | 223 | UUGGCUCUGGCCUGUCCU |
| 53 | 224 | UUCAACUGUUGCCUCCGGUUCUGAAGGUGUUCU |
| 53 | 225 | UACUUCAUCCCACUGAUUCUGAAUU |
| 53 | 226 | CUGAAGGUGUUCUUGUACUUCAUCC |
| 53 | 227 | CUGUUGCCUCCGGUUCUGAAGGUGU |
| 53 | 228 | CUGUUGCCUCCGGUUCUGAAGGUGUUCUUG |
| 53 | 229 | CAACUGUUGCCUCCGGUUCUGAAGGUGUUC |
| 53 | 230 | UUGCCUCCGGUUCUGAAGGUGUUCUUGUAC |
| 53 | 231 | GUUGCCUCCGGUUCUGAAGGUGUUC |
| 53 | 232 | CUCCGGUUCUGAAGGUGUUCUUG |
| 53 | 233 | CUCCGGUUCUGAAGGUGUUCUU |
| 53 | 234 | CUCCGGUUCUGAAGGUGUUCU |
| 53 | 235 | CUCCGGUUCUGAAGGUGUUC |
| 53 | 236 | CUCCGGUUCUGAAGGUGUU |
| 53 | 237 | CAUUCAACUGUUGCCUCCGGUUCUG |
| 53 | 238 | CUGUUGCCUCCGGUUCUGAAGGUG |
| 53 | 239 | CAUUCAACUGUUGCCUCCGGUUCUGAAGGUG |
| 53 | 240 | UACUAACCUUGGUUUCUGUGA |
| 53 | 241 | UGUAUAGGGACCCUCCUUCCAUGACUC |
| 53 | 242 | CUAACCUUGGUUUCUGUGAUUUUCU |
| 53 | 243 | GGUAUCUUUGAUACUAACCUUGGUUUC |
| 53 | 244 | AUUCUUUCAACUAGAAUAAAAG |
| 53 | 245 | GAUUCUGAAUUCUUUCAACUAGAAU |
| 53 | 246 | AUCCCACUGAUUCUGAAUUC |
| 53 | 247 | AACCGAGACCGGACAGGAUUCU |
| 53 | 266 | GGAAGCUAAGGAAGAAGCUGAGCAGG |
| 55 | 248 | CUGUUGCAGUAAUCUAUGAG |
| 55 | 249 | UGCCAUUGUUUCAUCAGCUCUUU |
| 55 | 250 | UGCAGUAAUCUAUGAGUUUC |
| 55 | 251 | UCCUGUAGGACAUUGGCAGU |
| 55 | 252 | GAGUCUUCUAGGAGCCUU |

Examples of oligonucleotides for promoting DMD gene editing include International Patent Publication WO2018053632A1, published Mar. 29, 2018, entitled "METHODS OF MODIFYING THE DYSTROPHIN GENE AND RESTORING DYSTROPHIN EXPRESSION AND USES THEREOF"; International Patent Publication WO2017049407A1, published Mar. 30, 2017, entitled "MODIFICATION OF THE DYSTROPHIN GENE AND USES THEREOF"; International Patent Publication WO2016161380A1, published Oct. 6, 2016, entitled "CRISPR/CAS-RELATED METHODS AND COMPOSI- TIONS FOR TREATING DUCHENNE MUSCULAR DYSTROPHY AND BECKER MUSCULAR DYSTROPHY"; International Patent Publication WO2017095967, published Jun. 8, 2017, entitled "THERAPEUTIC TARGETS FOR THE CORRECTION OF THE HUMAN DYSTROPHIN GENE BY GENE EDITING AND METHODS OF USE"; International Patent Publication WO2017072590A1, published May 4, 2017, entitled "MATERIALS AND METHODS FOR TREATMENT OF DUCHENNE MUSCULAR DYSTROPHY"; International Patent Publication WO2018098480A1, published May 31, 2018, entitled "PREVENTION OF MUSCULAR DYSTROPHY BY CRISPR/CPF1-MEDIATED GENE EDITING"; US Patent Application Publication US20170266320A1, published Sep. 21, 2017, entitled "RNA-Guided Systems for In Vivo Gene Editing"; International Patent Publication WO2016025469A1, published Feb. 18, 2016, entitled "PREVENTION OF MUSCULAR DYSTROPHY BY CRISPR/CAS9-MEDIATED GENE EDITING"; U.S. Patent Application Publication 2016/0201089, published Jul. 14, 2016, entitled "RNA-GUIDED GENE EDITING AND GENE REGULATION"; and U.S. Patent Application Publication 2013/0145487, published Jun. 6, 2013, entitled "MEGANUCLEASE VARIANTS CLEAVING A DNA TARGET SEQUENCE FROM THE DYSTROPHIN GENE AND USES THEREOF", the contents of each of which are incorporated herein in their entireties. In some embodiments, an oligonucleotide may have a region of complementarity to DMD gene sequences of multiple species, e.g., selected from human, mouse and non-human species.

In some embodiments, the oligonucleotide may have region of complementarity to a mutant DMD allele, for example, a DMD allele with at least one mutation in any of exons 1-79 of DMD in humans that leads to a frameshift and improper RNA splicing/processing.

In some embodiments, the oligonucleotide may target lncRNA or mRNA, e.g., for degradation. In some embodiments, the oligonucleotide may target, e.g., for degradation, a nucleic acid encoding a protein involved in a mismatch repair pathway. e.g., MSH2, MutLalpha, MutSbeta, MutLalpha. Non-limiting examples of proteins involved in mismatch repair pathways, for which mRNAs encoding such proteins may be targeted by oligonucleotides described herein, are described in Iyer, R. R. et al., "*DNA triplet repeat expansion and mismatch repair*" Annu Rev Biochem. 2015; 84:199-226; and Schmidt M. H. and Pearson C. E., "Disease-associated repeat instability and mismatch repair" DNA Repair (Amst). 2016 February; 38:117-26.

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In a some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the function of the target (e.g., mRNA) to cause a change of activity (e.g., inhibiting translation, altering splicing, exon skipping) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of an target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

b. Oligonucleotide Modifications:

The oligonucleotides described herein may be modified, e.g., comprise a modified sugar moiety, a modified internucleoside linkage, a modified nucleotide and/or combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleotides

In some embodiments, an oligonucleotide include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some embodiments, an oligonucleotide can include at least one 2'-O-methyl-modified nucleotide, and in some embodiments, all of the nucleotides include a 2'-O-methyl modification. In some embodiments, an oligonucleotide comprises modified nucleotides in which the ribose ring comprises a bridge moiety connecting two atoms in the ring, e.g., connecting the 2'-O atom to the 4'-C atom. In some embodiments, the oligonucleotides are "locked," e.g., comprise modified nucleotides in which the ribose ring is "locked" by a methylene bridge connecting the 2'-O atom and the 4'-C atom. Examples of LNAs are described in International Patent Application Publication WO/2008/043753, published on Apr. 17, 2008, and entitled "*RNA Antagonist Compounds For The Modulation Of PCSK9*", the contents of which are incorporated herein by reference in its entirety.

Other modifications that may be used in the oligonucleotides disclosed herein include ethylene-bridged nucleic acids (ENAs). ENAs include, but are not limited to, 2'-0,4'-C-ethylene-bridged nucleic acids. Examples of ENAs are provided in International Patent Publication No. WO 2005/042777, published on May 12, 2005, and entitled "*APP/ENA Antisense*"; Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties.

In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. In some embodiments, the oligonucleotide comprises a modified nucleotide disclosed in one of the following United States patent or patent Application Publications: U.S. Pat. No. 7,399,845, issued on Jul. 15, 2008, and entitled "6-Modified Bicyclic Nucleic Acid Analogs"; U.S. Pat. No. 7,741,457, issued on Jun. 22, 2010, and entitled "6-Modified Bicyclic Nucleic Acid Analogs"; U.S. Pat. No. 8,022,193, issued on Sep. 20, 2011, and entitled "6-*Modified Bicyclic Nucleic Acid Analogs*"; U.S. Pat. No. 7,569,686, issued on Aug. 4, 2009, and entitled "*Compounds And Methods For Synthesis Of Bicyclic Nucleic Acid Analogs*"; U.S. Pat. No. 7,335,765, issued on Feb. 26, 2008, and entitled "*Novel Nucleoside And Oligonucleotide Analogues*"; U.S. Pat. No. 7,314,923, issued on Jan. 1, 2008, and entitled "*Novel Nucleoside And Oligonucleotide Analogues*"; U.S. Pat. No. 7,816,333, issued on Oct. 19, 2010, and entitled "*Oligonucleotide Analogues And Methods Utilizing The Same*" and US Publication Number 2011/0009471 now U.S. Pat. No. 8,957,201, issued on Feb. 17, 2015, and entitled "*Oligonucleotide Analogues And Methods Utilizing The Same*", the entire contents of each of which are incorporated herein by reference for all purposes.

In some embodiments, the oligonucleotide comprises at least one nucleotide modified at the 2' position of the sugar, preferably a 2'-O-alkyl. 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA.

In some embodiments, the oligonucleotide may have at least one modified nucleotide that results in an increase in Tm of the oligonucleotide in a range of ° C., 2° C., 3° C. 4° C., or 5° C. compared with an oligonucleotide that does not have the at least one modified nucleotide. The oligonucleotide may have a plurality of modified nucleotides that result in a total increase in Tm of the oligonucleotide in a range of 2° C., 3° C. 4° C., 5° C., 6° C., 7° C., 8° C., 9° C., 10° C., 15° C., 20° C., 25° C., 30° C., 35° C. 40° C., 45° C. or more compared with an oligonucleotide that does not have the modified nucleotide.

The oligonucleotide may comprise alternating nucleotides of different kinds. For example, an oligonucleotide may comprise alternating deoxyribonucleotides or ribonucleotides and 2'-fluoro-deoxyribonucleotides. An oligonucleotide may comprise alternating deoxyribonucleotides or ribonucleotides and 2'-O-methyl nucleotides. An oligonucleotide may comprise alternating 2'-fluoro nucleotides and 2'-O-methyl nucleotides. An oligonucleotide may comprise alternating bridged nucleotides and 2'-fluoro or 2'-O-methyl nucleotides.

d. Internucleotide Linkages/Backbones

In some embodiments, oligonucleotide may contain a phosphorothioate or other modified internucleotide linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleotide linkages at the first, second, and/or third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177, 196; 5,188,897; 5,264,423; 5,276,019; 5,278,302; 5,286, 717; 5,321,131; 5,399,676; 5,405,939; 5,453,496; 5,455, 233; 5,466,677; 5,476,925; 5,519,126; 5,536,821; 5,541, 306; 5,550,111; 5,563,253; 5,571,799; 5,587,361; and 5,625, 050.

In some embodiments, oligonucleotides may have heteroatom backbones, such as methylene(methylimino) or MMI backbones; amide backbones (see De Mesmaeker et al Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides by adjusted based on the configuration of the chiral phosphorus atoms. In some embodiments, appropriate methods may be used to synthesize P-chiral oligonucleotide analogs in a stereocontrolled manner (e.g., as described in Oka N, Wada T, Stereocontrolled synthesis of oligonucleotide analogs containing chiral internucleotidic phosphorus atoms. Chem Soc Rev. 2011 December; 40(12): 5829-43) In some embodiments, phosphorothioate containing oligonucleotides comprise nucleoside units that are joined together by either substantially all Sp or substantially all Rp phosphorothioate intersugar linkages are provided. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-95%; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, the oligonucleotide is a gapmer. A gapmer oligonucleotide generally has the formula 5'-X—Y—Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., one to six modified nucleotides. Examples of modified nucleotides include, but are not limited to, 2' MOE or 2'OMe or Locked Nucleic Acid bases (LNA). The flanking sequences X and Z may be of one to twenty nucleotides, one to eight nucleotides or one to five nucleotides in length, in some embodiments. The flanking sequences X and Z may be of similar length or of dissimilar lengths. The gap-segment Y may be a nucleotide sequence of five to twenty nucleotides, size to twelve nucleotides or six to ten nucleotides in length, in some embodiments.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170, and PCT publication Nos. WO2008049085 and WO2009090182, each of which is herein incorporated by reference in its entirety.

i. Mixmers

In some embodiments, an oligonucleotide described herein may be a mixmer or comprise a mixmer sequence pattern. In general, mixmers are oligonucleotides that comprise both naturally and non-naturally occurring nucleotides or comprise two different types of non-naturally occurring nucleotides typically in an alternating pattern. Mixmers generally have higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule. Such oligonucleotides that are incapable of recruiting RNAse H have been described, for example, see WO2007/112754 or WO2007/112753.

In some embodiments, the mixmer comprises or consists of a repeating pattern of nucleotide analogues and naturally occurring nucleotides, or one type of nucleotide analogue and a second type of nucleotide analogue. However, a mixmer need not comprise a repeating pattern and may instead comprise any arrangement of modified nucleotides and naturally occurring nucleotides or any arrangement of one type of modified nucleotide and a second type of modified nucleotide. The repeating pattern, may, for instance be every second or every third nucleotide is a modified nucleotide, such as LNA, and the remaining nucleotides are naturally occurring nucleotides, such as DNA, or are a 2' substituted nucleotide analogue such as 2'MOE or 2' fluoro analogues, or any other modified nucleotide described herein. It is recognized that the repeating pattern of modified nucleotide, such as LNA units, may be combined with modified nucleotide at fixed positions—e.g. at the 5' or 3' termini.

In some embodiments, a mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive modified nucleotide, such as at least two consecutive LNAs. In some embodiments, the mixmer comprises at least a region consisting of at least three consecutive modified nucleotide units, such as at least three consecutive LNAs.

In some embodiments, the mixmer does not comprise a region of more than 7, more than 6, more than 5, more than 4, more than 3, or more than 2 consecutive nucleotide analogues, such as LNAs. In some embodiments, LNA units may be replaced with other nucleotide analogues, such as those referred to herein.

Mixmers may be designed to comprise a mixture of affinity enhancing modified nucleotides, such as in non-limiting example LNA nucleotides and 2'-O-methyl nucleotides. In some embodiments, a mixmer comprises modified internucleoside linkages (e.g., phosphorothioate internucleoside linkages or other linkages) between at least two, at least three, at least four, at least five or more nucleotides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, a mixmer comprises one or more morpholino nucleotides. For example, in some embodiments, a mixmer may comprise morpholino nucleotides mixed (e.g., in an alternating manner) with one or more other nucleotides (e.g., DNA, RNA nucleotides) or modified nucleotides (e.g., LNA, 2'-O-Methyl nucleotides).

In some embodiments, mixmers are useful for splice correcting or exon skipping, for example, as reported in Touznik A., et al., *LNA/DNA mixmer-based antisense oligonucleotides correct alternative splicing of the SMN2 gene and restore SMN protein expression in type* 1 *SAM fibroblasts* Scientific Reports, volume 7, Article number: 3672 (2017), Chen S. et al., *Synthesis of a Morpholino Nucleic Acid (MNA)-Uridine Phosphoramidite, and Exon Skipping Using MNA/2'-O-Methyl Mixmer Antisense Oligonucleotide*, Molecules 2016, 21, 1582, the contents of each which are incorporated herein by reference.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule, The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule.

k. MicroRNA (MiRNAs)

In some embodiments, an oligonucleotide may be a microRNA (miRNA). MicroRNAs (referred to as "miR-NAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see. e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual. Cold Spring Harbor Laboratory (Current edition). The ribozyme RNA sequences may be synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs. or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Multimers

In some embodiments, molecular payloads may comprise multimers (e.g., concatemers) of 2 or more oligonucleotides connected by a linker. In this way, in some embodiments, the oligonucleotide loading of a complex can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via a oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide.

Still, in some embodiments, multimers can comprise a branched structure comprising multiple oligonucleotides linked together by a branching linker.

Further examples of multimers that may be used in the complexes provided herein are disclosed, for example, in US patent application Number 2015/0315588 A1, entitled Methods of delivering multiple targeting oligonucleotides to a cell using cleavable linkers, which was published on Nov. 5, 2015; US patent application Number 2015/0247141 A1, entitled Multimeric Oligonucleotide Compounds, which was published on Sep. 3, 2015, US patent application Number US 2011/0158937 A1, entitled Immunostimulatory Oligonucleotide Multimers, which was published on Jun. 30, 2011; and U.S. Pat. No. 5,693,773, entitled Triplex-Forming Antisense Oligonucleotides Having Abasic Linkers Targeting Nucleic Acids Comprising Mixed Sequences Of Purines And Pyrimidines, which issued on Dec. 2, 1997, the contents of each of which are incorporated herein by reference in their entireties.

ii. Small Molecules:

Any suitable small molecule may be used as a molecular payload, as described herein. In some embodiments, the small molecule enhances exon skipping of DMD mutant sequences. In some embodiments, the small molecule is as described in US Patent Application Publication US20140080896A1, published Mar. 20, 2014, entitled "IDENTIFICATION OF SMALL MOLECULES THAT FACILITATE THERAPEUTIC EXON SKIPPING". Further examples of small molecule payloads are provided in U.S. Pat. No. 9,982,260, issued May 29, 2018, entitled "Identification of structurally similar small molecules that enhance therapeutic exon skipping". For example, in some embodiments, the small molecule is an enhancer of exon skipping such as perphenazine, flupentixol, zuclopenthixol or corynanthine. In some embodiments, a small molecule enhancer of exon skipping inhibits the ryanodine receptor or calmodulin. In some embodiments, the small molecule is an H-Ras pathway inhibitor such as manumycin A. In some embodiments, the small molecule is a suppressor of stop codons and desensitizes ribosomes to premature stop codons. In some embodiments, the small molecule is ataluren, as described in McElroy S. P. et al. "A Lack of Premature Termination Codon Read Through Efficacy of PTC124 (Ataluren) in a Diverse Array of Reporter Assays." PLOS Biology, published Jun. 25, 2013. In some embodiments, the small molecule is a corticosteroid, e.g., as described in Manzur, A. Y. et al. "Glucocorticoid corticosteroids for Duchenne muscular dystrophy". Cochrane Database Syst Rev. 2004; (2):CD003725. In some embodiments, the small molecule upregulates the expression and/or activity of genes that can replace the function of dystrophin, such as utrophin. In some embodiments, a utrophin modulator is as described in International Publication No. WO2007091106, published Aug. 16, 2007, entitled "TREATMENT OF DUCHENNE MUSCULAR DYSTROPHY" and/or International Publication No. WO/2017/168151, published Oct. 5, 2017, entitled "COMPOSITION FOR THE TREATMENT OF DUCHENNE MUSCULAR DYSTROPHY".

iii. Peptides/Proteins

Any suitable peptide or protein may be used as a molecular payload, as described herein. In some embodiments, a protein is an enzyme. In some embodiments, peptides or proteins may produced, synthesized, and/or derivatized using several methodologies, e.g. phage displayed peptide libraries, one-bead one-compound peptide libraries, or positional scanning synthetic peptide combinatorial libraries.

Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081; Samoylova, T. I. and Smith, B. F. "Elucidation of muscle-binding peptides by phage display screening." Muscle Nerve, 1999, 22:4. 460-6).

In some embodiments, a peptide may facilitate exon skipping in an mRNA expressed from a mutated DMD allele. In some embodiments, a peptide may promote the expression of functional dystrophin and/or the expression of a protein capable of functioning in place of dystrophin. In some embodiments, payload is a protein that is a functional fragment of dystrophin, e.g. an amino acid segment of a functional dystrophin protein.

In some embodiments, the peptide or protein comprises at least one zinc finger.

In some embodiments, the peptide or protein may comprise about 2-25 amino acids, about 2-20 amino acids, about 2-15 amino acids, about 2-10 amino acids, or about 2-5 amino acids. The peptide or protein may comprise naturally-occurring amino acids, e.g. cysteine, alanine, or non-naturally-occurring or modified amino acids. Non-naturally occurring amino acids include O-amino acids, homo-amino acids, proline derivatives, 3-substituted alanine derivatives, linear core amino acids, N-methyl amino acids, and others known in the art. In some embodiments, the peptide may be linear; in other embodiments, the peptide may be cyclic, e.g. bicyclic.

iv. Nucleic Acid Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "Engineered nucleic acids encoding a modified erythropoietin and their expression". In some embodiments, a mRNA may comprise a 5' methyl cap. In some embodiments, a mRNA may comprise a polyA tail, optionally of up to 160 nucleotides in length. A gene expression construct may encode a sequence of a dystrophin protein, a dystrophin fragment, a mini-dystrophin, a utrophin protein, or any protein that shares a common function with dystrophin. In some embodiments, the gene expression construct may be expressed, e.g., overexpressed, within the nucleus of a muscle cell. In some embodiments, the gene expression constructs encodes a protein that comprises at least one zinc finger. In some embodiments, the gene expression construct encodes a protein that promotes the expression of dystrophin or a protein that shares function with dystrophin, e.g., utrophin. In some embodiments, the gene expression construct encodes a gene editing enzyme. In some embodiments, the gene expression construct is as described in U.S. Patent Application Publication US20170368198A1, published Dec. 28, 2017, entitled "Optimized mini-dystrophin genes and expression cassettes and their use"; Duan D. "Myodys, a full-length dystrophin plasmid vector for Duchenne and Becker muscular dystrophy gene therapy." Curr Opin Mol Ther 2008; 10:86-94; and expression cassettes disclosed in Tang, Y. et al., "AAV-directed muscular dystrophy gene therapy" Expert Opin Biol Ther. 2010 March; 10(3):395-408; the contents of each of which are incorporated herein by reference in their entireties.

C. Linkers

Complexes described herein generally comprise a linker that connects a muscle-targeting agent to a molecular payload. A linker comprises at least one covalent bond. In some embodiments, a linker may be a single bond, e.g., a disulfide bond or disulfide bridge, that connects a muscle-targeting agent to a molecular payload. However, in some embodiments, a linker may connect a muscle-targeting agent to a molecular through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the muscle-targeting agent or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493; Jain, N. et al. "Current ADC Linker Chemistry" Pharm Res. 2015, 32:11, 3526-3540; McCombs, J. R. and Owen, S. C. "Antibody Drug Conjugates: Design and Selection of Linker, Payload and Conjugation Chemistry" AAPS J. 2015, 17:2, 339-351).

A precursor to a linker typically will contain two different reactive species that allow for attachment to both the muscle-targeting agent and a molecular payload. In some embodiments, the two different reactive species may be a nucleophile and/or an electrophile. In some embodiments, a linker is connected to a muscle-targeting agent via conjugation to a lysine residue or a cysteine residue of the muscle-targeting agent. In some embodiments, a linker is connected to a cysteine residue of a muscle-targeting agent via a maleimide-containing linker, wherein optionally the maleimide-containing linker comprises a maleimidocaproyl or maleimidomethyl cyclohexane-1-carboxylate group. In some embodiments, a linker is connected to a cysteine residue of a muscle-targeting agent or thiol functionalized molecular payload via a 3-arylpropionitrile functional group. In some embodiments, a linker is connected to a muscle-targeting agent and/or a molecular payload via an amide bond, a hydrazide, a triazole, a thioether, or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids. Non-naturally occurring amino acids include β-amino acids, homo-amino acids, proline derivatives, 3-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by an disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

azide, a peptide sequence comprising a LPXT sequence, a thioether, a biotin, a biphenyl, repeating units of polyethylene glycol or equivalent compounds, acid esters, acid amides, sulfamides, and/or an alkoxy-amine linker. In some embodiments, sortase-mediated ligation will be utilized to covalently link a muscle-targeting agent comprising a LPXT sequence to a molecular payload comprising a $(G)_n$ sequence (see, e.g. Proft T. Sortase-mediated protein ligation: an emerging biotechnology tool for protein modification and immobilization. Biotechnol Lett. 2010, 32(1):1-10).

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N. O, and S; an optionally substituted hetero-

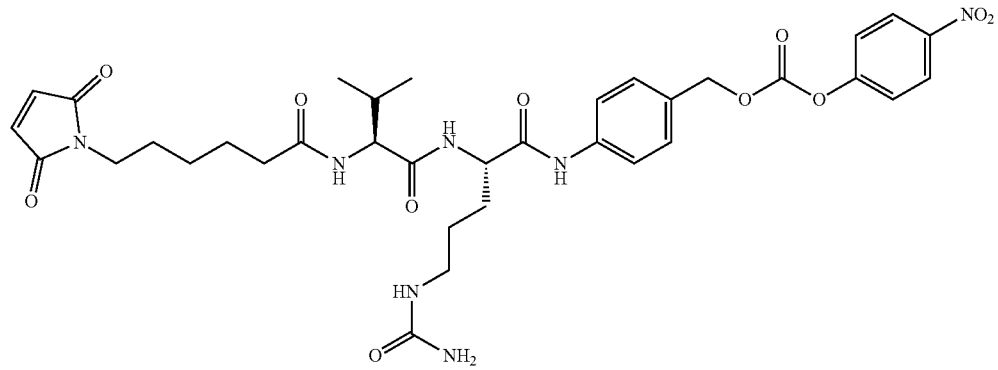 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

In some embodiments, after conjugation, the val-cit linker has a structure of:

cyclylene further comprising at least one heteroatom selected from N, O, and S: an imino, an optionally substi-

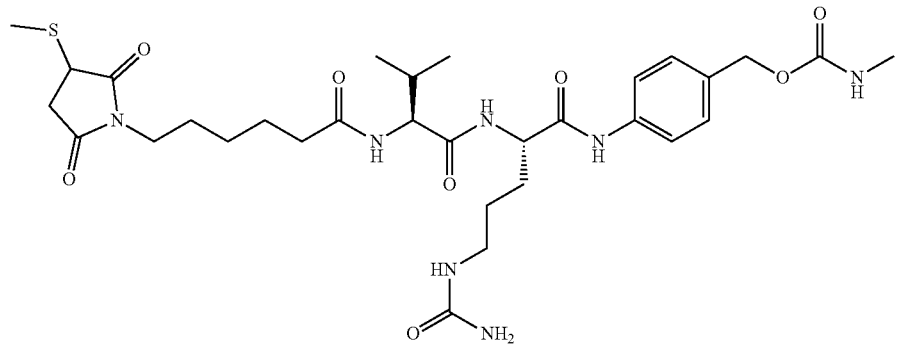

ii. Non-Cleavable Linkers

In some embodiments, non-cleavable linkers may be used. Generally, a non-cleavable linker cannot be readily degraded in a cellular or physiological environment. In some embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkynetuted nitrogen species, an optionally substituted oxygen species O, an optionally substituted sulfur species, or a poly(alkylene oxide), e.g. polyethylene oxide or polypropylene oxide.

iii. Linker Conjugation

In some embodiments, a linker is connected to a muscle-targeting agent and/or molecular payload via a phosphate, thioether, ether, carbon-carbon, or amide bond. In some embodiments, a linker is connected to an oligonucleotide through a phosphate or phosphorothioate group, e.g. a terminal phosphate of an oligonucleotide backbone. In some embodiments, a linker is connected to an muscle-targeting agent, e.g. an antibody, through a lysine or cysteine residue present on the muscle-targeting agent In some embodiments, a linker is connected to a muscle-targeting agent and/or molecular payload by a cycloaddition reaction between an azide and an alkyne to form a triazole, wherein the azide and the alkyne may be located on the muscle-targeting agent, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "*Fused Cyclooctyne Compounds And Their Use In Metal-free Click Reactions*". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "*Process For The Modification Of A Glycoprotein Using A Glycosyltransferase That Is Or Is Derived From A β(1,4)-N-Acetylgalactosaminyltransferases*". In some embodiments, a cycloaddition reaction between an azide and an alkyne to form a triazole, wherein the azide and the alkyne may be located on the muscle-targeting agent, molecular payload, or the linker is as described in International Patent Application Publication WO2014065661, published on May 1, 2014, entitled, "*Modified antibody, antibody-conjugate and process for the preparation thereof*"; or International Patent Application Publication WO2016170186, published on Oct. 27, 2016, entitled, "*Process For The Modification Of A Glycoprotein Using A Glycosyltransferase That Is Or Is Derived From A β(1,4)-N-Acetylgalactosaminyltransferases*".

In some embodiments, a linker further comprises a spacer, e.g., a polyethylene glycol spacer or an acyl/carbamoyl sulfamide spacer, e.g., a HydraSpace™ spacer. In some embodiments, a spacer is as described in Verkade, J. M. M. et al., "*A Polar Sulfamide Spacer Significantly Enhances the Manufacturability. Stability. and Therapeutic Index of Antibody-Drug Conjugates*", Antibodies, 2018, 7, 12.

In some embodiments, a linker is connected to a muscle-targeting agent and/or molecular payload by the Diels-Alder reaction between a dienophile and a diene/hetero-diene, wherein the dienophile and the diene/hetero-diene may be located on the muscle-targeting agent, molecular payload, or the linker. In some embodiments a linker is connected to a muscle-targeting agent and/or molecular payload by other pericyclic reactions, e.g. ene reaction. In some embodiments, a linker is connected to a muscle-targeting agent and/or molecular payload by an amide, thioamide, or sulfonamide bond reaction. In some embodiments, a linker is connected to a muscle-targeting agent and/or molecular payload by a condensation reaction to form an oxime, hydrazone, or semicarbazide group existing between the linker and the muscle-targeting agent and/or molecular payload.

In some embodiments, a linker is connected to a muscle-targeting agent and/or molecular payload by a conjugate addition reactions between a nucleophile, e.g. an amine or a hydroxyl group, and an electrophile, e.g. a carboxylic acid or an aldehyde. In some embodiments, a nucleophile may exist on a linker and an electrophile may exist on a muscle-targeting agent or molecular payload prior to a reaction between a linker and a muscle-targeting agent or molecular payload. In some embodiments, an electrophile may exist on a linker and a nucleophile may exist on a muscle-targeting agent or molecular payload prior to a reaction between a linker and a muscle-targeting agent or molecular payload. In some embodiments, an electrophile may be an azide, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

D. Examples of Antibody-Molecular Payload Complexes

Other aspects of the present disclosure provide complexes comprising any one the muscle targeting agent (e.g., a transferrin receptor antibodies) described herein covalently linked to any of the molecular payloads (e.g., an oligonucleotide) described herein. In some embodiments, the muscle targeting agent (e.g., a transferrin receptor antibody) is covalently linked to a molecular payload (e.g., an oligonucleotide) via a linker. Any of the linkers described herein may be used. In some embodiments, the linker is linked to the 5' end, the 3' end, or internally of the oligonucleotide. In some embodiments, the linker is linked to the antibody via a thiol-reactive linkage (e.g., via a cysteine in the antibody).

An exemplary structure of a complex comprising a transferrin receptor antibody covalently linked to an oligonucleotide via a Val-cit linker is provided below:

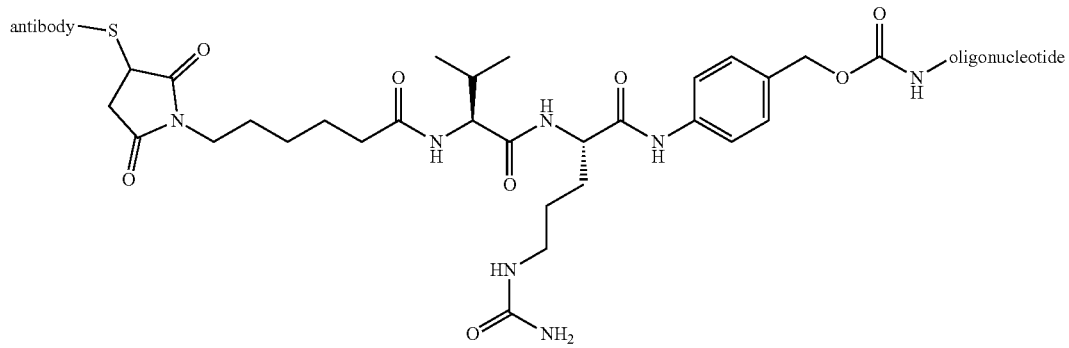

wherein the linker is linked to the 5' end, the 3' end, or internally of the oligonucleotide, and wherein the linker is linked to the antibody via a thiol-reactive linkage (e.g., via a cysteine in the antibody).

It should be appreciated that antibodies can be linked to oligonucleotides with different stoichiometries, a property that may be referred to as a drug to antibody ratios (DAR) with the "drug" being the oligonucleotide. In some embodiments, one oligonucleotide is linked to an antibody (DAR=1). In some embodiments, two oligonucleotides are linked to an antibody (DAR=2). In some embodiments, three oligonucleotides are linked to an antibody (DAR=3). In some embodiments, four oligonucleotides are linked to an antibody (DAR=4). In some embodiments, a mixture of different complexes, each having a different DAR, is provided. In some embodiments, an average DAR of complexes in such a mixture may be in a range of 1 to 3, 1 to 4, 1 to 5 or more. DAR may be increased by conjugating oligonucleotides to different sites on an antibody and/or by conjugating multimers to one or more sites on antibody. For example, a DAR of 2 may be achieved by conjugating a single oligonucleotide to two different sites on an antibody or by conjugating a dimer oligonucleotide to a single site of an antibody.

In some embodiments, the complex described herein comprises a transferrin receptor antibody (e.g., an antibody or any variant thereof as described herein) covalently linked to an oligonucleotide (e.g., an oligonucleotide that is capable of inducing exon skipping of DMD). In some embodiments, the complex described herein comprises a transferrin receptor antibody (e.g., an antibody or any variant thereof as described herein) covalently linked to an oligonucleotide (e.g., an oligonucleotide that is capable of inducing exon skipping of DMD) via a linker (e.g., a Val-cit linker). In some embodiments, the linker (e.g., a Val-cit linker) is linked to the 5' end, the 3' end, or internally of the nucleotide (e.g., an oligonucleotide that is capable of inducing exon skipping of DMD). In some embodiments, the linker (e.g., a Val-cit linker) is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMD targeting oligonucleotide, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to a DMD targeting oligonucleotide, wherein the transferrin receptor antibody comprises a VH having the amino acid sequence of SEQ ID NO: 283 and a VL having the amino acid sequence of SEQ ID NO: 284. In some embodiments, the complex described herein comprises a transferrin receptor antibody covalently linked to a DMD targeting oligonucleotide, wherein the transferrin receptor antibody comprises a VH having the amino acid sequence of SEQ ID NO: 285 and a VL having the amino acid sequence of SEQ ID NO: 286.

In some embodiments, the complex described herein comprises a transferrin receptor antibody covalently linked to a DMD targeting oligonucleotide, wherein the transferrin receptor antibody comprises a heavy chain having the amino acid sequence of SEQ ID NO: 289 and a light chain having the amino acid sequence of SEQ ID NO: 290. In some embodiments, the complex described herein comprises a transferrin receptor antibody covalently linked to a DMD targeting oligonucleotide, wherein the transferrin receptor antibody comprises a heavy chain having the amino acid sequence of SEQ ID NO: 291 and a light chain having the amino acid sequence of SEQ ID NO: 292.

In some embodiments, the complex described herein comprises a transferrin receptor antibody covalently linked to a DMD targeting oligonucleotide via a linker (e.g., a Val-cit linker), wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to a DMD targeting oligonucleotide via a linker (e.g., a Val-cit linker), wherein the transferrin receptor antibody comprises a VH having the amino acid sequence of SEQ ID NO: 283 and a VL having the amino acid sequence of SEQ ID NO: 284. In some embodiments, the complex described herein comprises a transferrin receptor antibody covalently linked to a DMD targeting oligonucleotide via a linker (e.g., a Val-cit linker), wherein the transferrin receptor antibody comprises a VH having the amino acid sequence of SEQ ID NO: 285 and a VL having the amino acid sequence of SEQ ID NO: 286.

In some embodiments, the complex described herein comprises a transferrin receptor antibody covalently linked to a DMD targeting oligonucleotide via a linker (e.g., a Val-cit linker), wherein the transferrin receptor antibody comprises a heavy chain having the amino acid sequence of SEQ ID NO: 289 and a light chain having the amino acid sequence of SEQ ID NO: 290. In some embodiments, the complex described herein comprises a transferrin receptor antibody covalently linked to a DMD targeting oligonucleotide via a linker (e.g., a Val-cit linker), wherein the transferrin receptor antibody comprises a heavy chain having the amino acid sequence of SEQ ID NO: 291 and a light chain having the amino acid sequence of SEQ ID NO: 292.

In some embodiments, the complex described herein comprises a transferrin receptor antibody covalently linked to a DMD targeting oligonucleotide via a Val-cit linker, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1, and wherein the complex comprises the structure of:

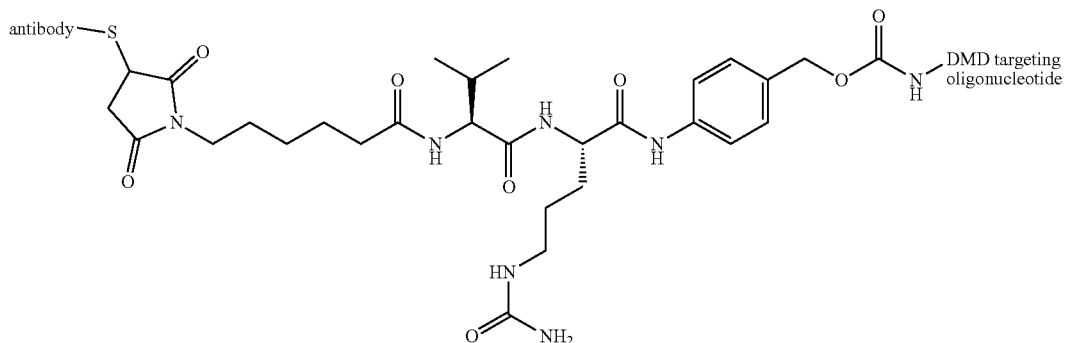

wherein the linker Val-cit linker is linked to the 5' end, the 3' end, or internally of the DMD targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMD targeting oligonucleotide via a Val-cit linker, wherein the transferrin receptor antibody comprises a VH having the amino acid sequence of SEQ ID NO: 283 and a VL having the amino acid sequence of SEQ ID NO: 284, and wherein the complex comprises the structure of:

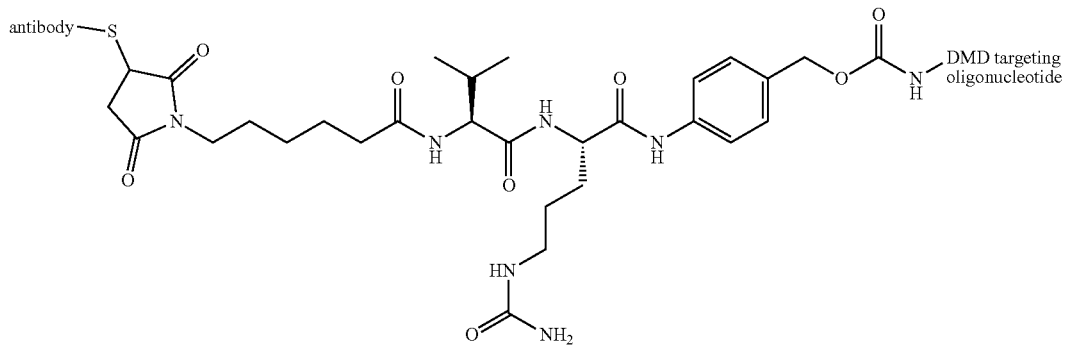

wherein the linker Val-cit linker is linked to the 5' end, the 3' end, or internally of DMD targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMD targeting oligonucleotide via a Val-cit linker, wherein the transferrin receptor antibody comprises a VH having the amino acid sequence of SEQ ID NO: 285 and a VL having the amino acid sequence of SEQ ID NO: 286, and wherein the complex comprises the structure of:

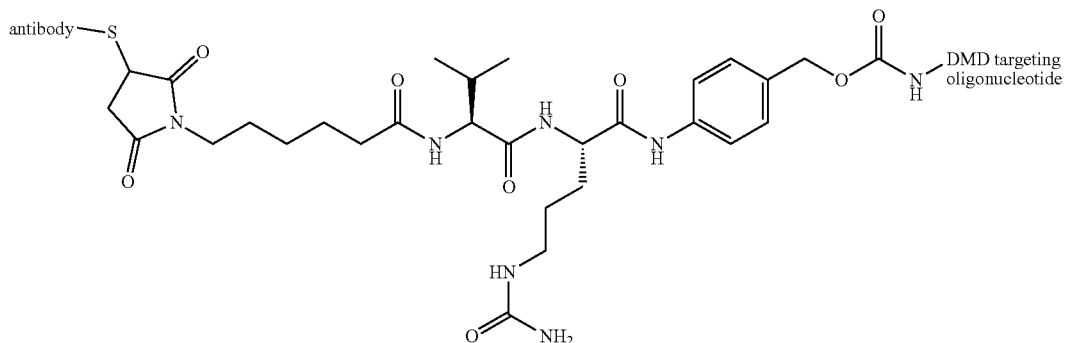

wherein the linker Val-cit linker is linked to the 5' end, the 3' end, or internally of the DMD targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMD targeting oligonucleotide via a Val-cit linker, wherein the transferrin receptor antibody comprises a heavy chain having the amino acid sequence of SEQ ID NO: 289 and a light chain having the amino acid sequence of SEQ ID NO: 290, and wherein the complex comprises the structure of:

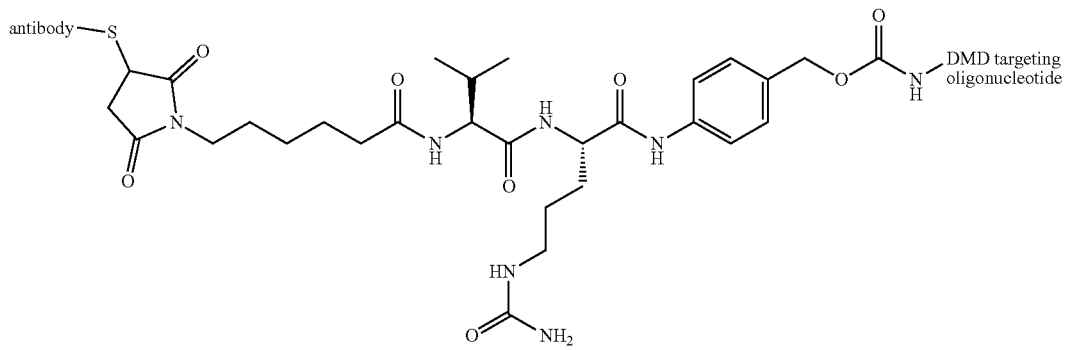

wherein the linker Val-cit linker is linked to the 5' end, the 3' end, or internally of DMD targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMD targeting oligonucleotide via a Val-cit linker, wherein the transferrin receptor antibody comprises a heavy chain having the amino acid sequence of SEQ ID NO: 291 and a light chain having the amino acid sequence of SEQ ID NO: 292, and wherein the complex comprises the structure of:

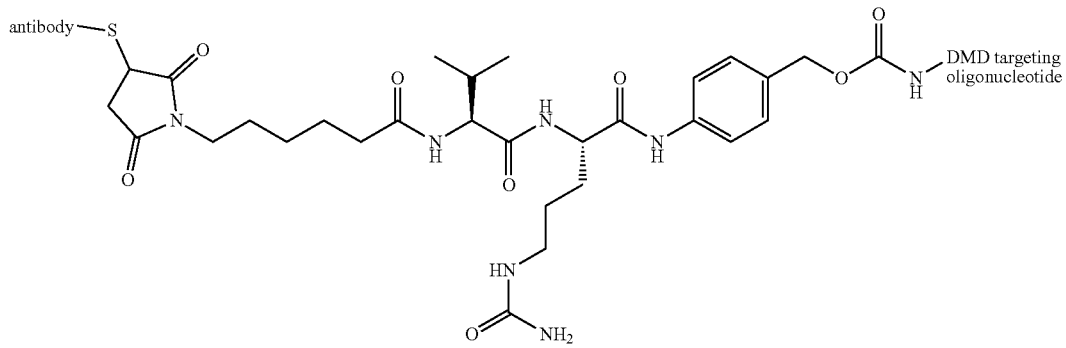

wherein the linker Val-cit linker is linked to the 5' end, the 3' end, or internally of DMD targeting oligonucleotide, and wherein the Val-cit linker is linked to the antibody (e.g., an antibody or any variant thereof as described herein) via a thiol-reactive linkage (e.g., via a cysteine in the antibody).

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the a complexes in a required amount in a selected solvent with one or a combination of ingredients enumerated above, as required, followed by filtered sterilization.

In some embodiments, a composition may contain at least about 0.1% of the a complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently to a molecular payload as described herein are effective in treating a subject having a dystrophinopathy. e.g., duchenne muscular dystrophy. In some embodiments, complexes comprise a molecular payload that is an oligonucleotide, e.g., an antisense oligonucleotide that facilitates exon skipping of an mRNA expressed from a mutated DMD allele.

In some embodiments, a subject may be a human subject, a non-human primate subject, a rodent subject, or any suitable mammalian subject. In some embodiments, a subject may have duchenne muscular dystrophy or other dystrophinopathy. In some embodiments, a subject has a mutated DMD allele, which may optionally comprise at least one mutation in a DMD exon that causes a frameshift mutation and leads to improper RNA splicing/processing. In some embodiments, a subject is suffering from symptoms of a severe dystrophinopathy, e.g. muscle atrophy or muscle loss. In some embodiments, a subject has an asymptomatic increase in serum concentration of creatine phosphokinase (CK) and/or muscle cramps with myoglobinuria. In some embodiments, a subject has a progressive muscle disease, such as Duchenne or Becker muscular dystrophy or DMD-associated dilated cardiomyopathy (DCM). In some embodiments, a subject is not suffering from symptoms of a dystrophinopathy.

An aspect of the disclosure includes a methods involving administering to a subject an effective amount of a complex as described herein. In some embodiments, an effective amount of a pharmaceutical composition that comprises a complex comprising a muscle-targeting agent covalently to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethyllactamide, dimethylformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations. e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment The efficacy of treatment may be assessed using any suitable methods. In some embodiments, the efficacy of treatment may be assessed by evaluation of observation of symptoms associated with a dystrophinopathy, e.g. muscle atrophy or muscle weakness, through measures of a subject's self-reported outcomes, e.g. mobility, self-care, usual activities, pain/discomfort, and anxiety/depression, or by quality-of-life indicators, e.g. lifespan.

In some embodiments, a pharmaceutical composition that comprises a complex comprising a muscle-targeting agent covalently to a molecular payload described herein is administered to a subject at an effective concentration sufficient to modulate activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

In some embodiments, a single dose or administration of a pharmaceutical composition that comprises a complex comprising a muscle-targeting agent covalently to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, 6, 7, 8, 9, 10, 11, or 12 weeks. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, or 6 months.

In some embodiments, a pharmaceutical composition may comprise more than one complex comprising a muscle-targeting agent covalently to a molecular payload. In some embodiments, a pharmaceutical composition may further comprise any other suitable therapeutic agent for treatment of a subject, e.g. a human subject having a dystrophinopathy. In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting HPRT with Transfected Antisense Oligonucleotides

A siRNA that targets hypoxanthine phosphoribosyltransferase (HPRT) was tested in vitro for its ability to reduce expression levels of HPRT in an immortalized cell line. Briefly, Hepa 1-6 cells were transfected with either a control siRNA (siCTRL; 100 nM) or the siRNA that targets HPRT (siHPRT; 100 nM), formulated with lipofectamine 2000. HPRT expression levels were evaluated 48 hours following transfection. A control experiment was also performed in which vehicle (phosphate-buffered saline) was delivered to Hepa 1-6 cells in culture and the cells were maintained for 48 hours. As shown in FIG. 1, it was found that the HPRT siRNA reduced HPRT expression levels by ~90% compared with controls.

TABLE 3

Sequences of siHPRT and siCTRL

| | Sequence |
|---|---|
| siHPRT sense strand | 5'-UcCuAuGaCuGuAgAuUuUaU-(CH$_2$)$_6$NH$_2$-3' |
| siHPRT antisense strand | 5'-paUaAaAuCuAcAgUcAuAgGasAsu-3' |
| siCTRL sense strand | 5'-UgUaAuAaCcAuAuCuAcCuU-(CH$_2$)$_6$NH$_2$-3' |
| siCTRL antisense strand | 5'-aAgGuAgAuAuGgUuAuUaCasAsa-3' |

*Lower case-2'Ome ribose; Capital letter-2'Fluoro ribose; p-phosphate linkage; s-phosphorothioate linkage

Example 2: Targeting HPRT with a Muscle-Targeting Complex

A muscle-targeting complex was generated comprising the HPRT siRNA used in Example 1 (siHPRT) covalently linked, via a non-cleavable N-gamma-maleimidobutyryl-oxysuccinimide ester (GMBS) linker, to DTX-A-002, an anti-transferrin receptor antibody.

Briefly, the GMBS linker was dissolved in dry DMSO and coupled to the 3' end of the sense strand of siHPRT through amide bond formation under aqueous conditions. Completion of the reaction was verified by Kaiser test. Excess linker and organic solvents were removed by gel permeation chromatography. The purified, maleimide functionalized sense strand of siHPRT was then coupled to DTX-A-002 antibody using a Michael addition reaction.

The product of the antibody coupling reaction was then subjected to hydrophobic interaction chromatography (HIC-HPLC). antiTfR-siHPRT complexes comprising one or two siHPRT molecules covalently attached to DTX-A-002 antibody were purified. Densitometry confirmed that the purified sample of complexes had an average siHPRT to antibody ratio of 1.46. SDS-PAGE analysis demonstrated that >90% of the purified sample of complexes comprised DTX-A-002 linked to either one or two siHPRT molecules.

Using the same methods as described above, a control IgG2a-siHPRT complex was generated comprising the HPRT siRNA used in Example 1 (siHPRT) covalently linked via the GMBS linker to an IgG2a (Fab) antibody (DTX-A-003). Densitometry confirmed that DTX-C-001 had an average siHPRT to antibody ratio of 1.46 and SDS-PAGE demonstrated that >90% of the purified sample of control complexes comprised DTX-A-003 linked to either one or two siHPRT molecules.

Figure 2:
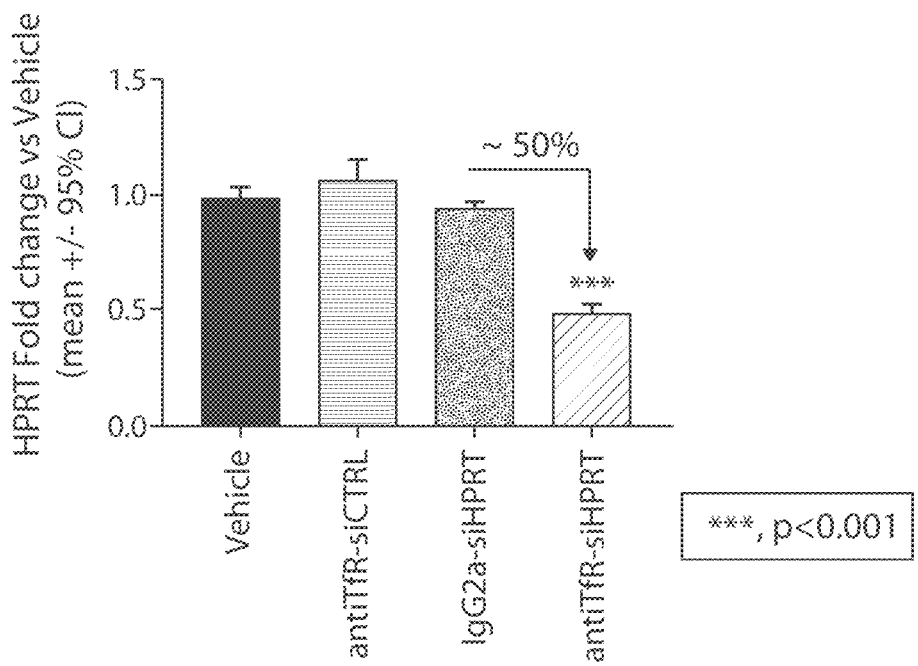
FIG. 2 depicts a non-limiting schematic showing the activity of a muscle targeting complex comprising an siRNA.

The antiTfR-siHPRT complex was then tested for cellular internalization and inhibition of HPRT in cellulo. Hepa 1-6 cells, which have relatively high expression levels of transferrin receptor, were incubated in the presence of vehicle (phosphate-buffered saline), IgG2a-siHPRT (100 nM), antiTfR-siCTRL (100 nM), or antiTfR-siHPRT (100 nM), for 72 hours. After the 72 hour incubation, the cells were isolated and assayed for expression levels of HPRT (FIG. 2). Cells treated with the antiTfR-siHPRT demonstrated a reduction in HPRT expression by ~50% relative to the cells treated with the vehicle control. Meanwhile, cells treated with either of the IgG2a-siHPRT or antiTfR-siCTRL had HPRT expression levels comparable to the vehicle control (no reduction in HPRT expression). These data indicate that the anti-transferrin receptor antibody of the antiTfR-siHPRT enabled cellular internalization of the complex, thereby allowing the siHPRT to inhibit expression of HPRT.

Example 3: Targeting HPRT in Mouse Muscle Tissues with a Muscle-Targeting Complex The muscle-targeting complex described in Example 2, antiTfR-siHPRT, was tested for inhibition of HPRT in mouse tissues. C57BL/6 wild-type mice were intravenously injected with a single dose of a vehicle control (phosphate-buffered saline); siHPRT (2 mg/kg of RNA); IgG2a-siHPRT (2 mg/kg of RNA, corresponding to 9 mg/kg antibody complex); or antiTfR-siHPRT (2 mg/kg of RNA, corresponding to 9 mg/kg antibody complex. Each experimental condition was replicated in four individual C57BL/6 wild-type mice. Following a three-day period after injection, the mice were euthanized and segmented into isolated tissue types. Individual tissue samples were subsequently assayed for expression levels of HPRT (FIGS. 3A-3B and 4A-4E).

Figure 3A:
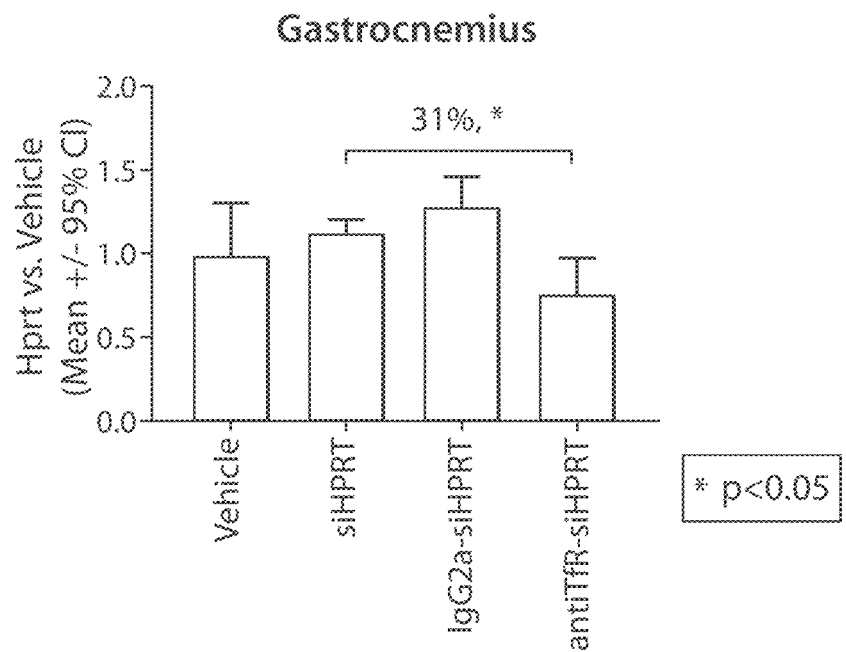
FIGS. 3A-3B depict non-limiting schematics showing the activity of a muscle targeting complex comprising an siRNA in mouse muscle tissues (gastrocnemius and heart) in vivo, relative to control experiments. (N=4 C57BL/6 WT mice)
Figure 3B:
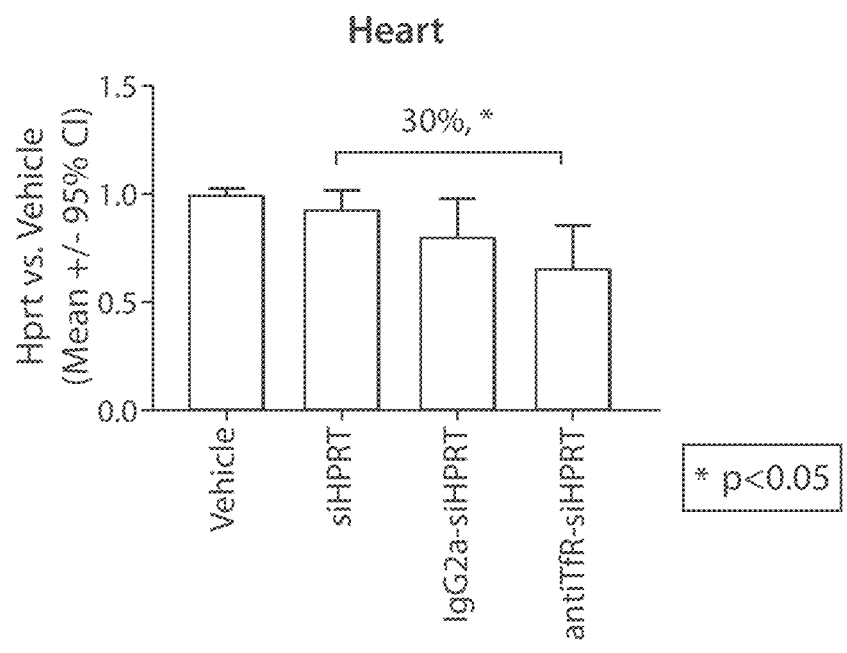
Figure 4A:
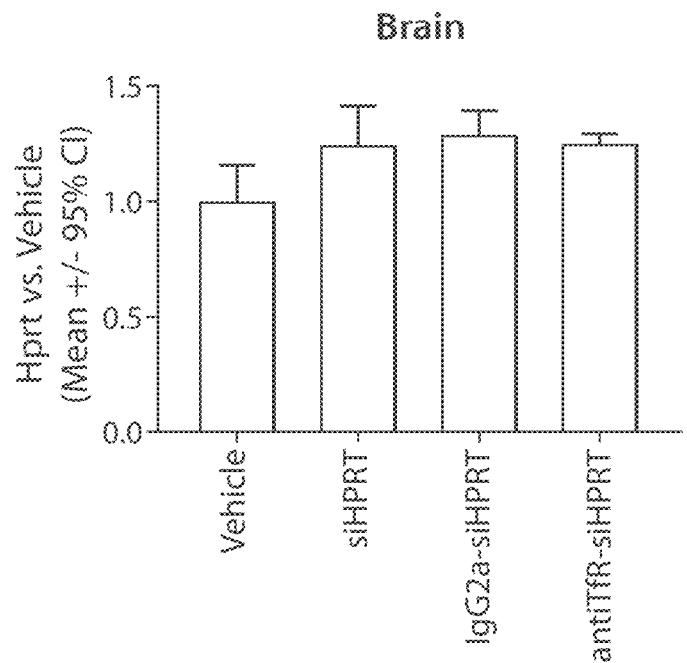
FIGS. 4A-4E depict non-limiting schematics showing the tissue selectivity of a muscle targeting complex comprising an siRNA.
Figure 4B:
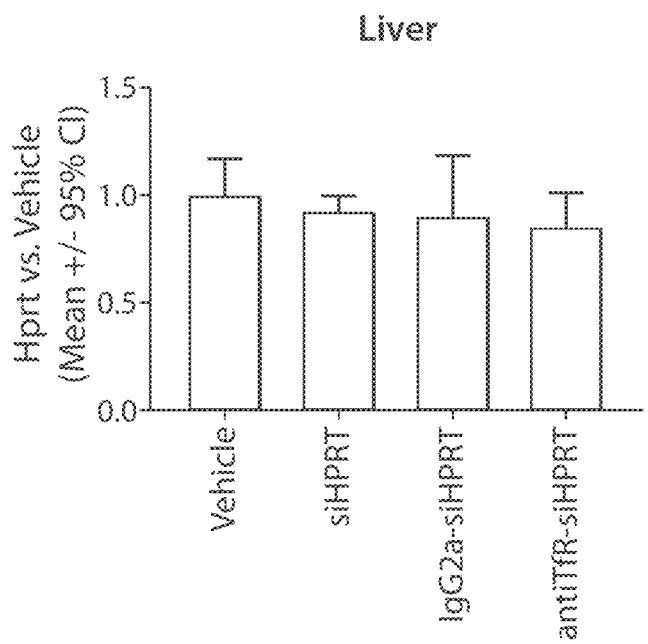
Figure 4C:
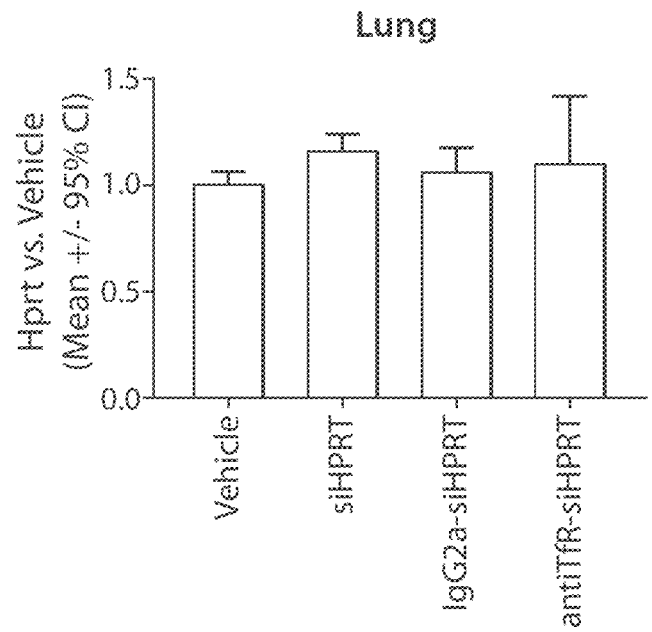
Figure 4D:
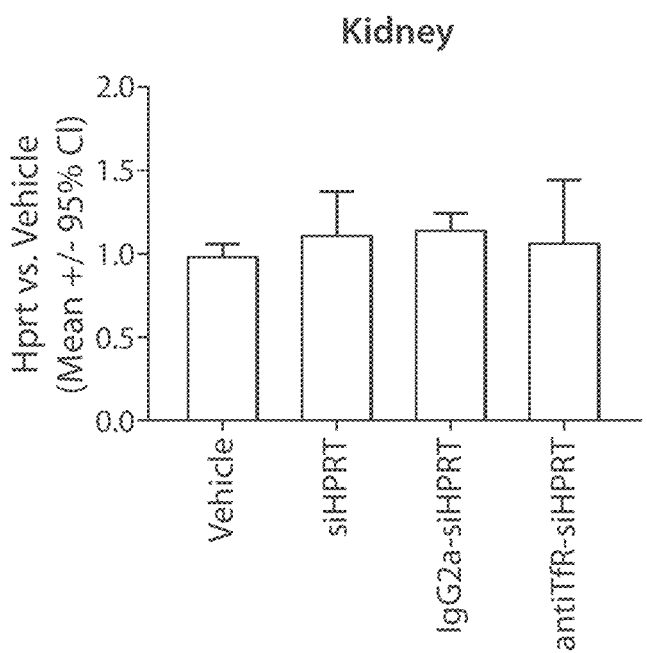
Figure 4E:
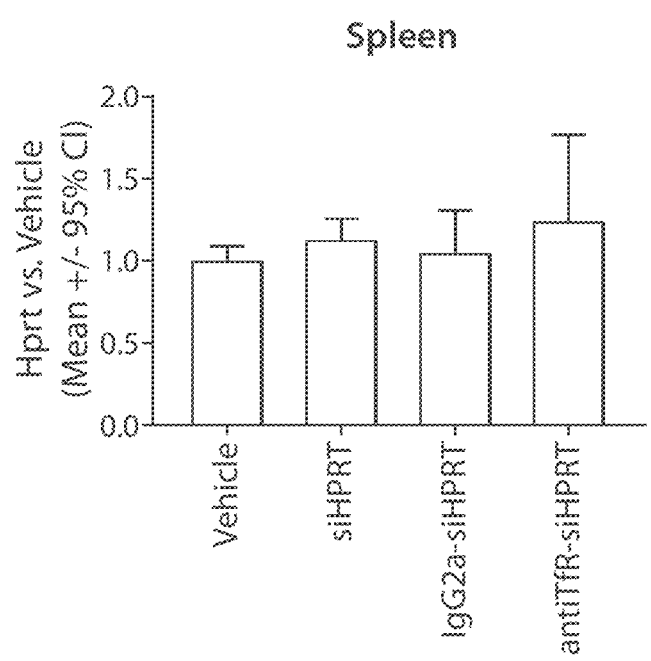

Mice treated with the antiTfR-siHPRT complex demonstrated a reduction in HPRT expression in gastrocnemius (31% reduction; p<0.05) and heart (30% reduction; p<0.05), relative to the mice treated with the siHPRT control (FIGS. 3A-3B). Meanwhile, mice treated with the IgG2a-siHPRT complex had HPRT expression levels comparable to the siHPRT control (little or no reduction in HPRT expression) for all assayed muscle tissue types.

Mice treated with the antiTfR-siHPRT complex demonstrated no change in HPRT expression in non-muscle tissues such as brain, liver, lung, kidney, and spleen tissues (FIGS. 4A-4E). These data indicate that the anti-transferrin receptor antibody of the antiTfR-siHPRT complex enabled cellular internalization of the complex into muscle-specific tissues in an in vivo mouse model, thereby allowing the siHPRT to inhibit expression of HPRT. These data further demonstrate that the antiTfR-oligonucleotide complexes of the current disclosure are capable of specifically targeting muscle tissues.

Example 4: Targeting DMD with a Muscle-Targeting Complex

A muscle-targeting complex is generated comprising an antisense oligonucleotide that targets a mutant allele of DMD (DMD ASO), for exon skipping. e.g., an oligonucleotide having a sequence as disclosed in Table 2, covalently linked, via a cathepsin cleavable linker, to DTX-A-002 (RI7 217 (Fab)), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule is coupled to $NH_2-C_6$-DMD ASO using an amide coupling reaction. Excess linker and organic solvents are removed by gel permeation chromatography. The purified Val-Cit-linker-DMD ASO is then coupled to a thiol-reactive anti-transferrin receptor antibody (DTX-A-002).

The product of the antibody coupling reaction is then subjected to hydrophobic interaction chromatography (HIC-HPLC) to purify the muscle-targeting complex. Densitometry and SDS-PAGE analysis of the purified complex allow for determination of the average ratio of ASO-to-antibody and total purity, respectively.

Using the same methods as described above, a control complex is generated comprising DMD ASO covalently linked via a Val-Cit linker to an IgG2a (Fab) antibody. The purified muscle-targeting complex comprising DTX-A-002 covalently linked to DMD ASO is then tested for cellular internalization and modulation of DMD exon skipping. Disease-relevant muscle cells that have relatively high expression levels of transferrin receptor, are incubated in the presence of vehicle control (saline), muscle-targeting complex (100 nM), or control complex (100 nM) for 72 hours. After the 72 hour incubation, the cells are isolated and assayed for expression levels of DMD.

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to.") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A complex comprising an anti-transferrin receptor antibody covalently linked to an exon-skipping oligonucleotide,
  wherein the anti-transferrin receptor antibody comprises a heavy chain variable region and a light chain variable region, wherein the heavy chain variable region and the light chain variable region comprise human or humanized framework regions; wherein the anti-transferrin receptor antibody binds in the range of C89 to F760 of human transferrin receptor protein 1 (TfR1) having an amino acid sequence as set forth in SEQ ID NO: 1;
  wherein the oligonucleotide of the complex is 30 nucleotides in length and comprises a region of complementarity of 25, 26, 27, 28, 29, or 30 nucleotides in length, wherein the region of complementarity is complementary to the annealing site of an oligonucleotide consisting of the sequence of SEQ ID NO: 195, wherein the oligonucleotide of the complex is a phosphorodiamidate morpholino oligomer (PMO); and
  wherein the oligonucleotide of the complex is covalently linked at the 5' end to a lysine residue of the anti-transferrin receptor antibody via a cleavable linker comprising a valine-citrulline sequence.

2. The complex of claim 1, wherein the anti-transferrin receptor antibody is in the form of a Fab fragment.

3. The complex of claim 2, wherein the region of complementarity is 30 nucleotides in length.

4. The complex of claim 3, wherein the oligonucleotide of the complex comprises 28, 29, or 30 contiguous nucleotides of the sequence of CTCCAACATCAAGGAAGATGGCATTTCTAG (SEQ ID NO: 296).

5. The complex of claim 4, wherein the cleavable linker comprises a triazole covalently linked to the valine-citrulline sequence and further covalently linked to a lysine residue of the anti-transferrin receptor antibody,
  wherein the triazole is obtained by a cycloaddition reaction between an azide and an alkyne to form the triazole, and
  wherein prior to the cycloaddition reaction, the azide is covalently linked to the valine-citrulline sequence of the cleavable linker that is covalently linked to the 5' end of the oligonucleotide of the complex, and the alkyne is provided in a bicyclononyne moiety.

6. The complex of claim 5, wherein the anti-transferrin receptor antibody is not glycosylated.

7. The complex of claim 1, wherein the nucleobases of the region of complementarity are selected from adenosine, thymidine, guanosine, and cytosine.

8. A composition comprising the complex of claim 1 and a pharmaceutically acceptable carrier, wherein the composition is formulated for intravenous administration.

9. A complex comprising an anti-transferrin receptor antibody covalently linked to an exon-skipping oligonucleotide,
  wherein the anti-transferrin receptor antibody comprises a heavy chain variable region and a light chain variable region, wherein the heavy chain variable region and the light chain variable region comprise human or humanized framework regions; wherein the anti-transferrin receptor antibody binds in the range of C89 to F760 of human transferrin receptor protein 1 (TfR1) having an amino acid sequence as set forth in SEQ ID NO: 1;
  wherein the oligonucleotide is 30 nucleotides in length, wherein the oligonucleotide is a phosphorodiamidate morpholino oligomer (PMO) comprising the sequence of CTCCAACATCAAGGAAGATGGCATTTCTAG (SEQ ID NO: 296); and
  wherein the oligonucleotide is covalently linked at the 5' end to a lysine residue of the anti-transferrin receptor antibody via a cleavable linker comprising a valine-citrulline sequence.

10. The complex of claim 9, wherein the anti-transferrin receptor antibody is in the form of a Fab fragment.

11. The complex of claim 10, wherein the cleavable linker comprises a triazole covalently linked to the valine-citrulline sequence and further covalently linked to a lysine residue of the anti-transferrin receptor antibody,
  wherein the triazole is obtained by a cycloaddition reaction between an azide and an alkyne to form the triazole, and
  wherein prior to the cycloaddition reaction, the azide is covalently linked to the valine-citrulline sequence of the cleavable linker that is covalently linked to the 5' end of the oligonucleotide and the alkyne is provided in a bicyclononyne moiety.

12. The complex of claim 11, wherein the anti-transferrin receptor antibody is not glycosylated.

13. A composition comprising the complex of claim 9 and a pharmaceutically acceptable carrier, wherein the composition is formulated for intravenous administration.

14. A method of inducing skipping of exon 51 of a DMD pre-mRNA in a muscle cell of a subject, the method comprising administering to the subject the complex of claim 1.

15. A method of treating Duchenne muscular dystrophy in a subject in need thereof, the method comprising administering to the subject a complex comprising an anti-transferrin receptor antibody covalently linked to an exon-skipping oligonucleotide,
    wherein the anti-transferrin receptor antibody comprises a heavy chain variable region and a light chain variable region, wherein the heavy chain variable region and the light chain variable region comprise human or humanized framework regions; wherein the anti-transferrin receptor antibody binds in the range of C89 to F760 of human transferrin receptor protein 1 (TfR1) having an amino acid sequence as set forth in SEQ ID NO: 1;
    wherein the oligonucleotide of the complex is 30 nucleotides in length and comprises a region of complementarity of 25, 26, 27, 28, 29, or 30 nucleotides in length, wherein the region of complementarity is complementary to the annealing site of an oligonucleotide consisting of the sequence of SEQ ID NO: 195, wherein the oligonucleotide is a phosphorodiamidate morpholino oligomer (PMO); and
    wherein the oligonucleotide of the complex is covalently linked at the 5' end to a lysine residue of the anti-transferrin receptor antibody via a cleavable linker comprising a valine-citrulline sequence.

16. The method of claim 15, wherein the oligonucleotide of the complex comprises the sequence of CTCCAACATCAAGGAAGATGGCATTTCTAG (SEQ ID NO: 296), and wherein the anti-transferrin receptor antibody is in the form of a Fab fragment.

17. The method of claim 16, wherein the cleavable linker comprises a triazole covalently linked to the valine-citrulline sequence and further covalently linked to a lysine residue of the anti-transferrin receptor antibody,
    wherein the triazole is obtained by a cycloaddition reaction between an azide and an alkyne to form the triazole, and
    wherein prior to the cycloaddition reaction, the azide is covalently linked to the valine-citrulline sequence of the cleavable linker that is covalently linked to the 5' end of the oligonucleotide of the complex, and the alkyne is provided in a bicyclononyne moiety.

18. The method of claim 15, wherein the oligonucleotide of the complex promotes the expression or activity of a functional dystrophin protein in a muscle cell of the subject.

19. The method of claim 18, wherein the muscle cell is a skeletal muscle cell or a cardiac muscle cell.

20. The method of claim 15, wherein the nucleobases of the region of complementarity are selected from adenosine, thymidine, guanosine, and cytosine.

21. The method of claim 15, wherein the subject is human.

22. The method of claim 15, wherein the complex is administered to the subject intravenously.

23. A method of inducing skipping of exon 51 of a DMD pre-mRNA in a muscle cell of a subject, the method comprising administering to the subject the complex of claim 9.

24. A method of treating Duchenne muscular dystrophy in a subject in need thereof, the method comprising administering to the subject a complex comprising an anti-transferrin receptor antibody covalently linked to an exon-skipping oligonucleotide,
    wherein the anti-transferrin receptor antibody comprises a heavy chain variable region and a light chain variable region, wherein the heavy chain variable region and the light chain variable region comprise human or humanized framework regions; wherein the anti-transferrin receptor antibody binds in the range of C89 to F760 of human transferrin receptor protein 1 (TfR1) having an amino acid sequence as set forth in SEQ ID NO: 1;
    wherein the oligonucleotide is 30 nucleotides in length, wherein the oligonucleotide is a phosphorodiamidate morpholino oligomer (PMO) comprising the sequence of CTCCAACATCAAGGAAGATGGCATTTCTAG (SEQ ID NO: 296); and
    wherein the oligonucleotide is covalently linked at the 5' end to a lysine residue of the anti-transferrin receptor antibody via a cleavable linker comprising a valine-citrulline sequence.

25. The method of claim 24, wherein the cleavable linker comprises a triazole covalently linked to the valine-citrulline sequence and further covalently linked to a lysine residue of the anti-transferrin receptor antibody,
    wherein the triazole is obtained by a cycloaddition reaction between an azide and an alkyne to form the triazole, and
    wherein prior to the cycloaddition reaction, the azide is covalently linked to the valine-citrulline sequence of the cleavable linker that is covalently linked to the 5' end of the oligonucleotide and the alkyne is provided in a bicyclononyne moiety.

26. The method of claim 25, wherein the anti-transferrin receptor antibody is not glycosylated.

27. The method of claim 24, wherein the oligonucleotide promotes the expression or activity of a functional dystrophin protein in a muscle cell of the subject.

28. The method of claim 27, wherein the muscle cell is a skeletal muscle cell or a cardiac muscle cell.

29. The method of claim 24, wherein the subject is human.

30. The method of claim 24, wherein the complex is administered to the subject intravenously.

* * * * *